US012799112B2

(12) United States Patent
Sintim et al.

(10) Patent No.: US 12,799,112 B2
(45) Date of Patent: Nov. 17, 2026

(54) TETRAHYDRO-3H-PYRAZOLO QUINOLONE AND TETRAHYDRO-3H-PYRROLO[3,2-F] QUINOLINE-CONTAINING COMPOUNDS AND USES THEREOF

(71) Applicant: Purdue Research Foundation, West Lafayette, IN (US)

(72) Inventors: Herman O. Sintim, Westfield, IN (US); Neetu Dayal, Agra (IN)

(73) Assignee: Purdue Research Foundation, West Lafayette, IN (US)

( * ) Notice: Subject to any disclaimer, the term of this patent is extended or adjusted under 35 U.S.C. 154(b) by 806 days.

(21) Appl. No.: 18/012,564

(22) PCT Filed: Jul. 1, 2021

(86) PCT No.: PCT/US2021/040034
§ 371 (c)(1),
(2) Date: Dec. 22, 2022

(87) PCT Pub. No.: WO2022/006365
PCT Pub. Date: Jan. 6, 2022

(65) Prior Publication Data
US 2023/0312562 A1 Oct. 5, 2023

Related U.S. Application Data

(60) Provisional application No. 63/047,281, filed on Jul. 2, 2020.

(51) Int. Cl.
*C07D 471/04* (2006.01)
*C07D 519/00* (2006.01)

(52) U.S. Cl.
CPC ......... *C07D 471/04* (2013.01); *C07D 519/00* (2013.01)

(58) Field of Classification Search
CPC ............................ C07D 471/04; C07D 519/00
USPC ........................................................ 514/279
See application file for complete search history.

(56) References Cited

U.S. PATENT DOCUMENTS

| | | | | |
|---|---|---|---|---|
| 7,915,416 | B2 | 3/2011 | Schiemann et al. | |
| 8,580,811 | B2 | 11/2013 | Pedram et al. | |
| 11,040,973 | B2 * | 6/2021 | Sintim | C07D 221/12 |
| 11,891,391 | B2 * | 2/2024 | Sintim | C07D 221/12 |
| 12,384,782 | B2 * | 8/2025 | Sintim | C07D 498/04 |

FOREIGN PATENT DOCUMENTS

| | | |
|---|---|---|
| WO | 94/04533 | 3/1994 |
| WO | 2020023323 | 1/2020 |

OTHER PUBLICATIONS

Pubchem SID 128042753 (i.e., Deposit Date: Dec. 4, 2011). (Year: 2011).*
Plewes et al., "Luteinizing Hormone Regulates The Phosphorylation And Localization Of The Mitochondrial Effector Dynamin-Related Protein-1 (DRP1) And Steroidogenesis In The Bovine Corpus Luteum", The FASEB Journal. 2020;34:5299-5316. (Year: 2020).*
International Search Report & Written Opinion for International Application No. PCT/US2021/040034, dated Dec. 17, 2021, (5 pages).
Pubchem-SID: 128042753; Deposit Date: Dec. 4, 2011, (7 pages).

* cited by examiner

*Primary Examiner* — Kortney L. Klinkel
*Assistant Examiner* — Grace Ching Hsu
(74) *Attorney, Agent, or Firm* — Purdue Research Foundation

(57) ABSTRACT

The present invention generally relates to tetrahydro-3H-pyrazolo-[4,3-f]-quinolone and tetrahydro-3H-pyrrolo-[3,2-f]quinoline-containing compounds as a tubulin polymerization inhibitor for the treatment of various cancers, and methods of uses thereof. Pharmaceutical compositions and the methods for treating those kinase related diseases are within the scope of this invention.

19 Claims, 9 Drawing Sheets

FIG. 1A
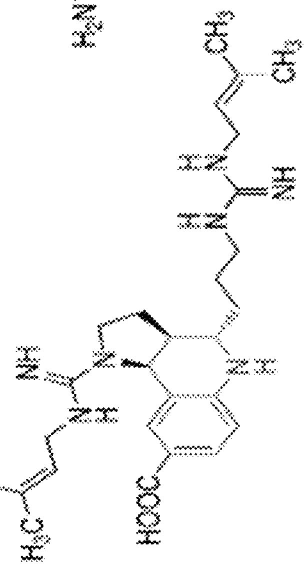
Martinellic acid
(Bradykinin Receptor Antagonist)
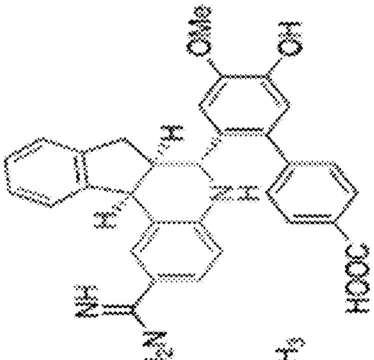
BMS-593214
(FVIIa inhibitor)
Anticoagulant
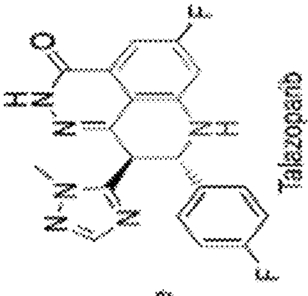
Talazoparib
(Parp inhibitor)
Anticancer
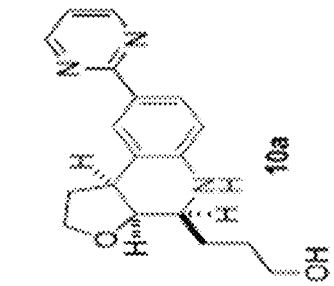
10a
FIG. 1B
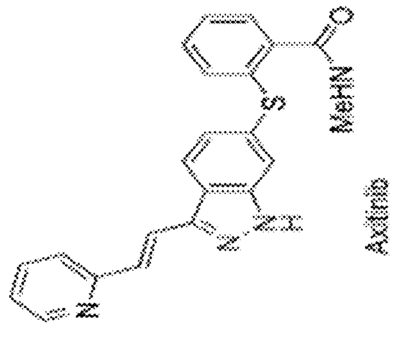
Axitinib
(VEGFR1-3 kinase inhibitor)
anticancer
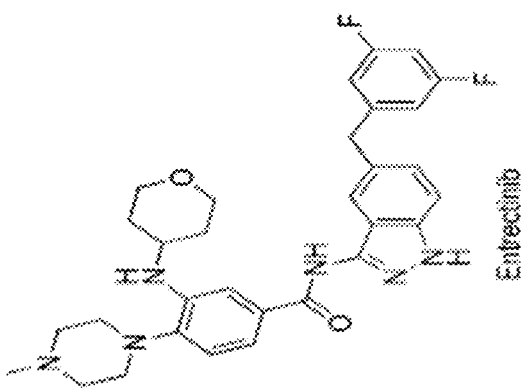
Entrectinib
(TrkA/B/C kinase inhibitor)
Anticancer
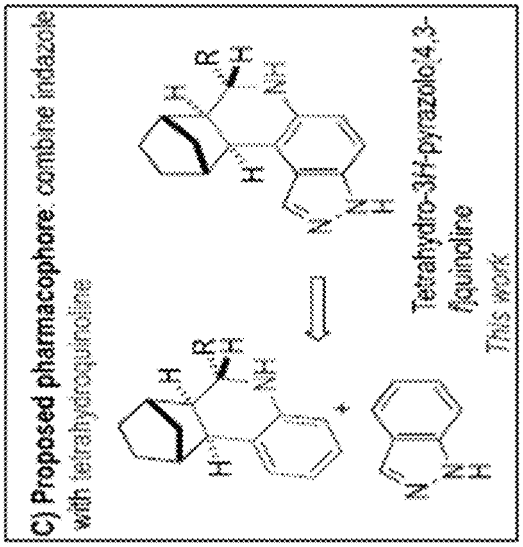
FIG. 1C Compound 1(*exo-exo*)

Encorafenib

Binimetinib

Bictegravir

Lasmiditan

HSD1787

$X_1$=NH, $X_2$=$X_3$=N (18)
$X_1$=NH, $X_2$=CH, $X_3$=N (19)

$R_1$ = Me (20)
$R_1$ = F (21)

$R_2$ = F; W = H (22)
$R_2$ = F; W = F (23)
$R_2$ = Cl; W = H (24)
$R_2$ = Br; W = H (25)
$R_2$ = OMe; W = H (26)
$R_2$ = H; W = F (27)

28

29

30

31

32

33

TETRAHYDRO-3H-PYRAZOLO QUINOLONE AND TETRAHYDRO-3H-PYRROLO[3,2-F]QUINOLINE-CONTAINING COMPOUNDS AND USES THEREOF

CROSS-REFERENCE TO RELATED APPLICATIONS

The present U.S. patent application is a national stage entry under 35 U.S.C. § 371(b) of International Application No. PCT/US2021/040034, filed on Jul. 1, 2021, which is related to and claims the priority benefit of U.S. Provisional Patent Application Ser. No. 63/047,281, filed Jul. 2, 2020, the contents of which are hereby incorporated by reference in their entirety into the present disclosure.

TECHNICAL FIELD

The present invention generally relates to tetrahydro-3H-pyrazolo[4,3-f]quinolone and tetrahydro-3H-pyrrolo[3,2-f]quinoline-containing compounds as a tubulin polymerization inhibitor and methods of uses thereof.

BACKGROUND

This section introduces aspects that may help facilitate a better understanding of the disclosure. Accordingly, these statements are to be read in this light and are not to be understood as admissions about what is or is not prior art.

The Povarov reaction, a multicomponent reaction between aromatic amines, aldehydes or ketones and alkenes, is a powerful methodology that can be used to quickly assemble complex molecular architectures. The Povarov reaction has been used to prepare 6,7,8,9-tetrahydro-3H-pyrazolo[4,3-f]quinolone-containing or tetrahydro-3H-pyrrolo[3,2-f]quinoline-containing compounds as a tubulin polymerization inhibitor that offers as a potential treatment for various cancers.

BRIEF DESCRIPTION OF DRAWINGS

FIG. 1A shows the structures of biologically active tetrahydroquinoline core containing compounds, synthesized using Povarov reaction; FIG. 1B shows the current indazole-containing drugs; FIG. 1C depicts combing the privileged indazole with tetrahydroquinoline to afford tetrahydro-3H-pyrazolo[4,3-f]quinoline.

FIG. 7A: compound HSD1787; FIG. 7B: compound 22; FIG. 7C: compound 23; FIG. 7D: 27. *Poor dose response so accurate GI50 could not be determined but at 10 μM, percent inhibition is less than 50%

DETAILED DESCRIPTION

Figure 2:
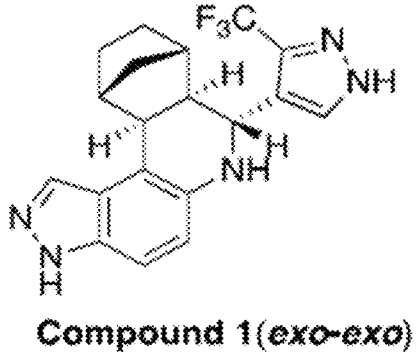
FIG. 2 depicts the ORTEP Diagram showing molecular structure of compound 1. Disorder omitted for clarity.
Figure 2:
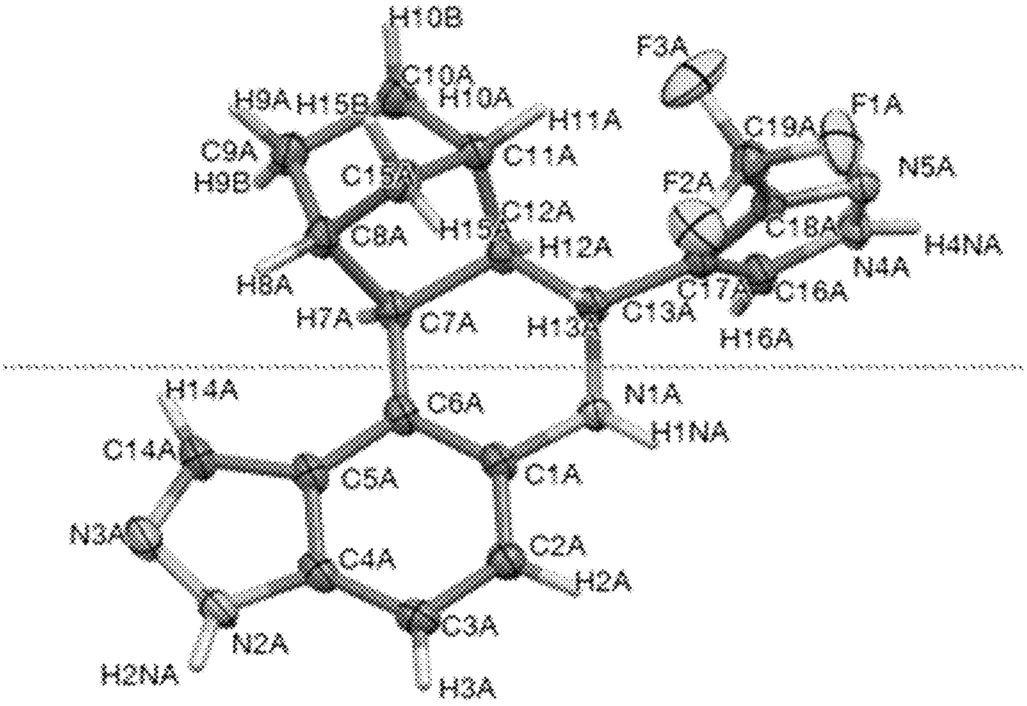

While the concepts of the present disclosure are illustrated and described in detail in the description herein, results in the their description are to be considered as exemplary and not restrictive in character; it being understood that only the illustrative embodiments are shown and described and that all changes and modifications that come within the spirit of the disclosure are desired to be protected.

The present invention generally relates to compounds useful for the treatment of an infection diseases. Pharmaceutical compositions and methods for treating those diseases are within the scope of this invention.

As used herein, the following terms and phrases shall have the meanings set forth below. Unless defined otherwise, all technical and scientific terms used herein have the same meaning as commonly understood to one of ordinary skill in the art.

In the present disclosure the term "about" can allow for a degree of variability in a value or range, for example, within 10%, within 5%, or within 1% of a stated value or of a stated limit of a range. In the present disclosure the term "substantially" can allow for a degree of variability in a value or range, for example, within 90%, within 95%, 99%, 99.5%, 99.9%, 99.99%, or at least about 99.999% or more of a stated value or of a stated limit of a range.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

The term "substituted" as used herein refers to a functional group in which one or more hydrogen atoms contained therein are replaced by one or more non-hydrogen atoms. The term "functional group" or "substituent" as used herein refers to a group that can be or is substituted onto a molecule. Examples of substituents or functional groups include, but are not limited to, a halogen (e.g., F, Cl, Br, and I); an oxygen atom in groups such as hydroxyl groups, alkoxy groups, aryloxy groups, aralkyloxy groups, oxo (carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, azides, hydroxylamines, cyano, nitro groups, N-oxides, hydrazides, and enamines; and other heteroatoms in various other groups.

The term "alkyl" as used herein refers to substituted or unsubstituted straight chain and branched alkyl groups and cycloalkyl groups having from 1 to about 20 carbon atoms ($C_1$-$C_{20}$), 1 to 12 carbons ($C_1$-$C_{12}$), 1 to 8 carbon atoms ($C_1$-$C_6$), or, in some embodiments, from 1 to 6 carbon atoms ($C_1$-$C_6$). Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neo-pentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to substituted or unsubstituted straight chain and branched divalent alkenyl and cycloalkenyl groups having from 2 to 20 carbon atoms ($C_2$-$C_{20}$), 2 to 12 carbons ($C_2$-$C_{12}$), 2 to 8 carbon atoms ($C_2$-$C_8$) or, in some embodiments, from 2 to 4 carbon atoms ($C_2$-$C_4$) and at least one carbon-carbon double bond. Examples of straight chain alkenyl groups include those with from 2 to 8 carbon atoms such as —CH═CH—, —CH═$CHCH_2$—, and the like. Examples of branched alkenyl groups include, but are not limited to, —CH═C($CH_3$)— and the like.

An alkynyl group is the fragment, containing an open point of attachment on a carbon atom that would form if a hydrogen atom bonded to a triply bonded carbon is removed from the molecule of an alkyne. The term "hydroxyalkyl" as used herein refers to alkyl groups as defined herein substituted with at least one hydroxyl (—OH) group.

The term "cycloalkyl" as used herein refers to substituted or unsubstituted cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. In some embodiments, cycloalkyl groups can have 3 to 6 carbon atoms ($C_3$-$C_6$). Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like.

The term "acyl" as used herein refers to a group containing a carbonyl moiety wherein the group is bonded via the carbonyl carbon atom. The carbonyl carbon atom is also bonded to another carbon atom, which can be part of a substituted or unsubstituted alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-40, 6-10, 1-5 or 2-5 additional carbon atoms bonded to the carbonyl group. An acryloyl group is an example of an acyl group. An acyl group can also include heteroatoms within the meaning here. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "aryl" as used herein refers to substituted or unsubstituted cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons ($C_6$-$C_{14}$) or from 6 to 10 carbon atoms ($C_6$-$C_{10}$) in the ring portions of the groups. Aryl groups can be unsubstituted or substituted, as defined herein. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed herein.

The term "aralkyl" and "arylalkyl" as used herein refers to alkyl groups as defined herein in which a hydrogen or carbon bond of an alkyl group is replaced with a bond to an aryl group as defined herein. Representative aralkyl groups include benzyl and phenylethyl groups and fused (cycloalkylaryl)alkyl groups such as 4-ethyl-indanyl. Aralkenyl groups are alkenyl groups as defined herein in which a hydrogen or carbon bond of an alkyl group is replaced with a bond to an aryl group as defined herein.

The term "heterocyclyl" as used herein refers to substituted or unsubstituted aromatic and non-aromatic ring compounds containing 3 or more ring members, of which, one or more is a heteroatom such as, but not limited to, B, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. In some embodiments, heterocyclyl groups include heterocyclyl groups that include 3 to 8 carbon atoms ($C_3$-$C_8$), 3 to 6 carbon atoms ($C_3$-$C_6$) or 6 to 8 carbon atoms ($C_6$-$C_8$).

A heteroaryl ring is an embodiment of a heterocyclyl group. The phrase "heterocyclyl group" includes fused ring species including those that include fused aromatic and non-aromatic groups. Representative heterocyclyl groups include, but are not limited to pyrrolidinyl, azetidinyl, piperidynyl, piperazinyl, morpholinyl, chromanyl, indolinonyl, isoindolinonyl, furanyl, pyrrolidinyl, pyridinyl, pyrazinyl, pyrimidinyl, triazinyl, thiophenyl, tetrahydrofuranyl, pyrrolyl, oxazolyl, oxadiazolyl, imidazolyl, triazyolyl, tetrazolyl, benzoxazolinyl, benzthiazolinyl, and benzimidazolinyl groups.

The term "heterocyclylalkyl" as used herein refers to alkyl groups as defined herein in which a hydrogen or carbon bond of an alkyl group as defined herein is replaced with a bond to a heterocyclyl group as defined herein. Representative heterocyclylalkyl groups include, but are not limited to, furan-2-yl methyl, furan-3-yl methyl, pyridine-3-yl methyl, tetrahydrofuran-2-yl methyl, and indol-2-yl propyl.

The term "heteroarylalkyl" as used herein refers to alkyl groups as defined herein in which a hydrogen or carbon bond of an alkyl group is replaced with a bond to a heteroaryl group as defined herein.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structure are substituted therewith.

The term "amine" as used herein refers to primary, secondary, and tertiary amines having, e.g., the formula $N(group)_3$ wherein each group can independently be H or non-H, such as alkyl, aryl, and the like. Amines include but are not limited to $R—NH_2$, for example, alkylamines, arylamines, alkylarylamines; $R_2NH$ wherein each R is independently selected, such as dialkylamines, diarylamines, aralkylamines, heterocyclylamines and the like; and $R_3N$ wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form $—NH_2$, —NHR, $—NR_2$, $—NR_3^+$, wherein each R is independently selected, and protonated forms of each, except for $—NR_3^+$, which cannot be protonated. Accordingly, any compound substituted with an amino group can be viewed as an amine. An "amino group" within the meaning herein can be a primary, secondary, tertiary, or quaternary amino group. An "alkylamino" group includes a monoalkylamino, dialkylamino, and trialkylamino group.

The terms "halo," "halogen," or "halide" group, as used herein, by themselves or as part of another substituent, mean, unless otherwise stated, a fluorine, chlorine, bromine, or iodine atom.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, $—CF(CH_3)_2$ and the like.

The term "optionally substituted," or "optional substituents," as used herein, means that the groups in question are either unsubstituted or substituted with one or more of the substituents specified. When the groups in question are substituted with more than one substituent, the substituents may be the same or different. When using the terms "independently," "independently are," and "independently selected from" mean that the groups in question may be the same or different. Certain of the herein defined terms may occur more than once in the structure, and upon such occurrence each term shall be defined independently of the other.

The compounds described herein may contain one or more chiral centers, or may otherwise be capable of existing as multiple stereoisomers. It is to be understood that in one embodiment, the invention described herein is not limited to any particular stereochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may include geometric centers, such as cis, trans, E, and Z double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

As used herein, the term "salts" and "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

Pharmaceutically acceptable salts can be synthesized from the parent compound which contains a basic or acidic moiety by conventional chemical methods. In some instances, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, the disclosure of which is hereby incorporated by reference.

The term "solvate" means a compound, or a salt thereof, that further includes a stoichiometric or non-stoichiometric amount of solvent bound by non-covalent intermolecular forces. Where the solvent is water, the solvate is a hydrate.

The term "prodrug" means a derivative of a compound that can hydrolyze, oxidize, or otherwise react under biological conditions (in vitro or in vivo) to provide an active compound, particularly a compound of the invention. Examples of prodrugs include, but are not limited to, derivatives and metabolites of a compound of the invention that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Specific prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers GmbH).

Further, in each of the foregoing and following embodiments, it is to be understood that the formulae include and represent not only all pharmaceutically acceptable salts of the compounds, but also include any and all hydrates and/or solvates of the compound formulae or salts thereof. It is to be appreciated that certain functional groups, such as the hydroxy, amino, and like groups form complexes and/or coordination compounds with water and/or various solvents, in the various physical forms of the compounds. Accordingly, the above formulae are to be understood to include and represent those various hydrates and/or solvates. In each of the foregoing and following embodiments, it is also to be understood that the formulae include and represent each possible isomer, such as stereoisomers and geometric isomers, both individually and in any and all possible mixtures. In each of the foregoing and following embodiments, it is also to be understood that the formulae include and represent any and all crystalline forms, partially crystalline forms, and non-crystalline and/or amorphous forms of the compounds.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As used herein, the term "administering" includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically acceptable carriers, adjuvants, and vehicles.

Illustrative formats for oral administration include tablets, capsules, elixirs, syrups, and the like. Illustrative routes for parenteral administration include intravenous, intraarterial, intraperitoneal, epidural, intraurethral, intrasternal, intramuscular and subcutaneous, as well as any other art recognized route of parenteral administration.

Illustrative means of parenteral administration include needle (including microneedle) injectors, needle-free injectors and infusion techniques, as well as any other means of parenteral administration recognized in the art. Parenteral formulations are typically aqueous solutions which may contain excipients such as salts, carbohydrates and buffering agents (preferably at a pH in the range from about 3 to about 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art. Parenteral administration of a compound is illustratively performed in the form of saline solutions or with the compound incorporated into liposomes. In cases where the compound in itself is not sufficiently soluble to be dissolved, a solubilizer such as ethanol can be applied.

The dosage of each compound of the claimed combinations depends on several factors, including: the administration method, the condition to be treated, the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect the dosage used.

It is to be understood that in the methods described herein, the individual components of a co-administration, or combination can be administered by any suitable means, contemporaneously, simultaneously, sequentially, separately or in a single pharmaceutical formulation. Where the co-administered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

Depending upon the route of administration, a wide range of permissible dosages are contemplated herein, including doses falling in the range from about 1 μg/kg to about 1 g/kg. The dosages may be single or divided, and may administered according to a wide variety of protocols, including q.d. (once a day), b.i.d. (twice a day), t.i.d. (three times a day), or even every other day, once a week, once a month, once a quarter, and the like. In each of these cases it is understood that the therapeutically effective amounts described herein correspond to the instance of administration, or alternatively to the total daily, weekly, month, or quarterly dose, as determined by the dosing protocol.

In addition to the illustrative dosages and dosing protocols described herein, it is to be understood that an effective amount of any one or a mixture of the compounds described herein can be determined by the attending diagnostician or physician by the use of known techniques and/or by observing results obtained under analogous circumstances. In determining the effective amount or dose, a number of factors are considered by the attending diagnostician or physician, including, but not limited to the species of mammal, including human, its size, age, and general health, the specific disease or disorder involved, the degree of or involvement or the severity of the disease or disorder, the response of the individual patient, the particular compound administered, the mode of administration, the bioavailability characteristics of the preparation administered, the dose regimen selected, the use of concomitant medication, and other relevant circumstances.

The term "patient" includes human and non-human animals such as companion animals (dogs and cats and the like) and livestock animals. Livestock animals are animals raised for food production. The patient to be treated is preferably a mammal, in particular a human being.

In some illustrative embodiments, this present disclosure relates to a compound having the formula (I)

(I)

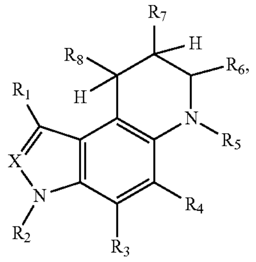

or a pharmaceutically acceptable salt thereof, wherein X is CH or N; $R_1$, $R_2$, $R_3$, $R_4$, $R_5$, $R_6$, $R_7$, and $R_8$ are, independently, an alkyl, aryl, heteroalkyl, heteroaryl, halogen, CN, amide, urea, carbamate, sulfonamide, alkoxy, —$OCF_3$, —$OCHF_2$, H, D, deuterated alkyl, deuterated aryl, deuterated heteroalkyl, and deuterated heteroaryl.

In some illustrative embodiments, this present disclosure relates to a compound having the formula (II)

(II)

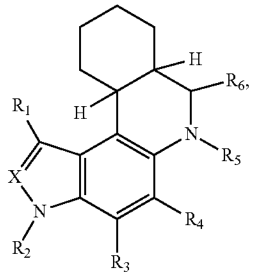

or a pharmaceutically acceptable salt thereof, wherein X is CH or N; and $R_1$, $R_2$, $R_3$, $R_4$, $R_5$, and $R_6$ are, independently, an alkyl, aryl, heteroalkyl, heteroaryl, halogen, CN, amide, urea, carbamate, sulfonamide, alkoxy, —$OCF_3$, —$OCHF_2$, H, D, deuterated alkyl, deuterated aryl, deuterated heteroalkyl, and deuterated heteroaryl.

In some illustrative embodiments, this present disclosure relates to a compound having the formula (III)

(III)

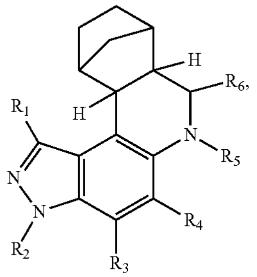

or a pharmaceutically acceptable salt thereof, wherein $R_1$, $R_2$, $R_3$, $R_4$, $R_5$, and $R_6$ are, independently, an alkyl, aryl, heteroalkyl, heteroaryl, halogen, CN, amide, urea, carbamate, sulfonamide, alkoxy, —$OCF_3$, —$OCHF_2$, H, D, deuterated alkyl, deuterated aryl, deuterated heteroalkyl, and deuterated heteroaryl.

In some illustrative embodiments, this present disclosure relates to a compound having the formula (III), wherein said compound comprises

1

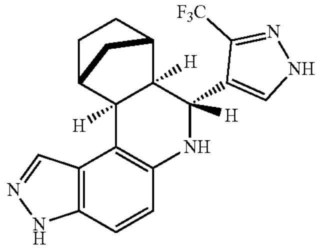

2

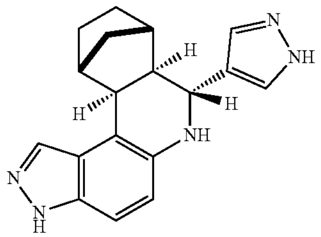

3

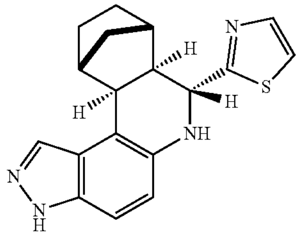

-continued
4
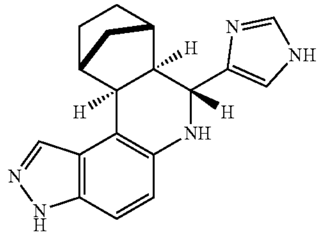
5
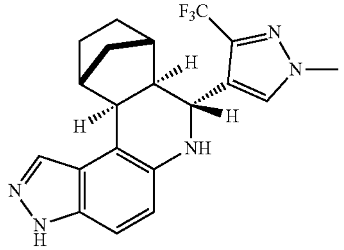
6
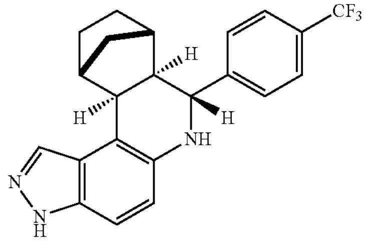
7
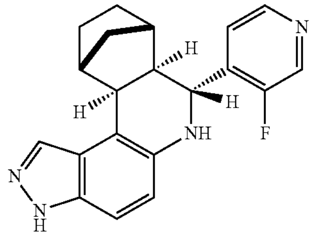
8
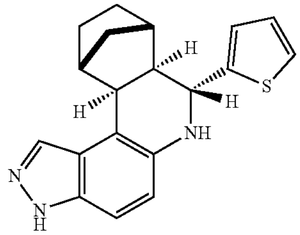
HSDF1
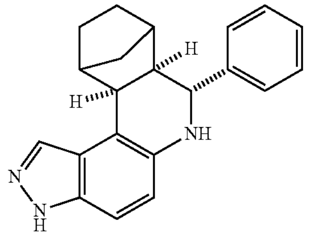
-continued
HSDF2
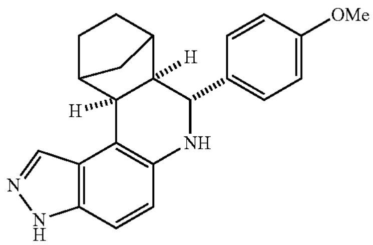
HSDF3
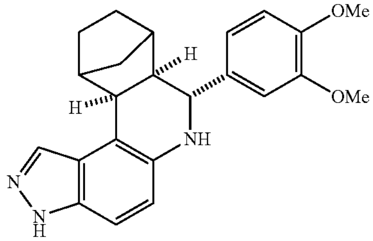
HSDF4
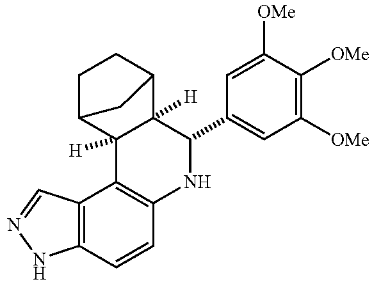
9
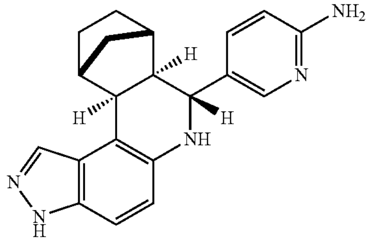
10
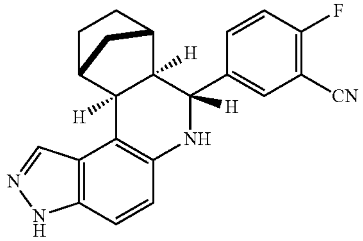
11
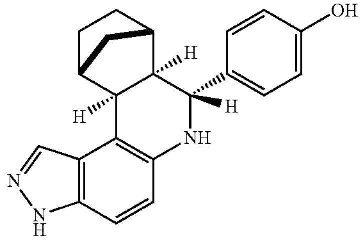

-continued
12
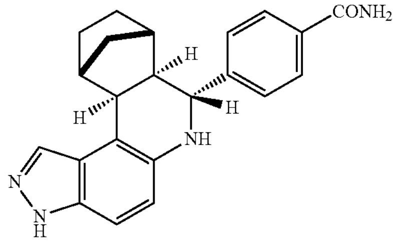
13
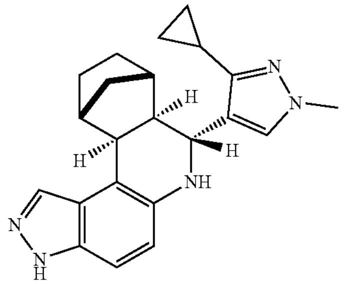
14
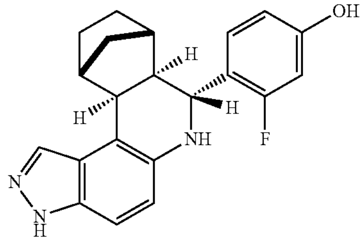
15
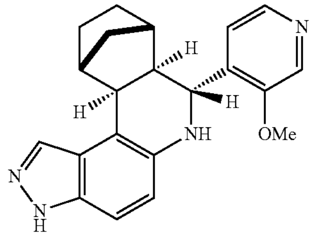
HSD1845
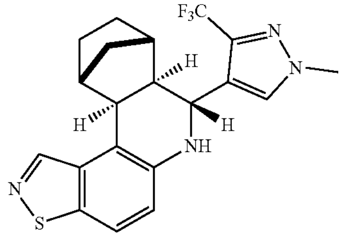
HSD4029
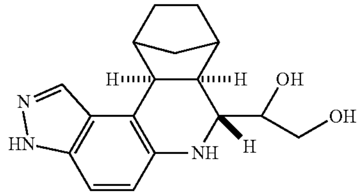
-continued
HSD4030
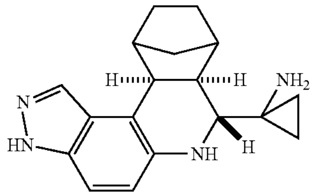
HSD4031
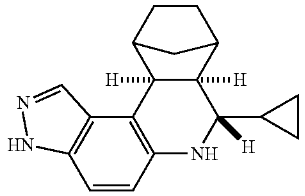
HSD4032
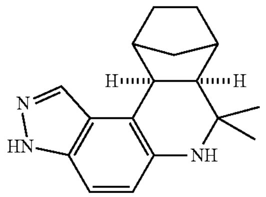
HSD1817
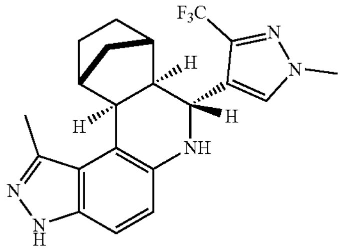
HSD4011
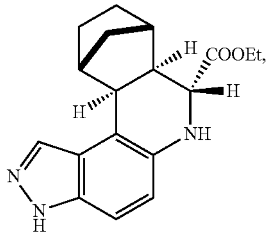
and
HSDF5
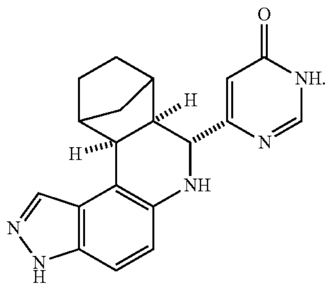
In some illustrative embodiments, this present disclosure relates to a compound having the formula (IV)

(IV)

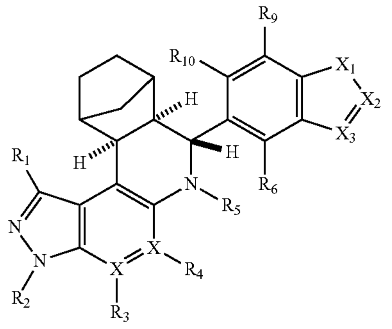

X = CH, N or a pharmaceutically acceptable salt thereof, wherein X, $X_1$, $X_2$, and $X_3$ are, independently, CH or N; and $R_1$, $R_2$, $R_3$, $R_4$, $R_5$, $R_6$, $R_7$, $R_8$, $R_9$, and $R_{10}$ are, independently, an alkyl, aryl, heteroalkyl, heteroaryl, halogen, CN, amide, urea, carbamate, sulfonamide, alkoxy, —$OCF_3$, —$OCHF_2$, H, D, deuterated alkyl, deuterated aryl, deuterated heteroalkyl, and deuterated heteroaryl.

In some illustrative embodiments, this present disclosure relates to a compound having the formula (IV), wherein said compound comprises HSD1901b

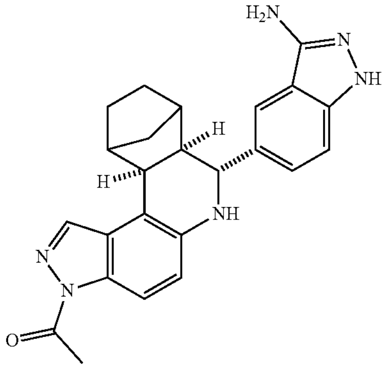

HSD1901c

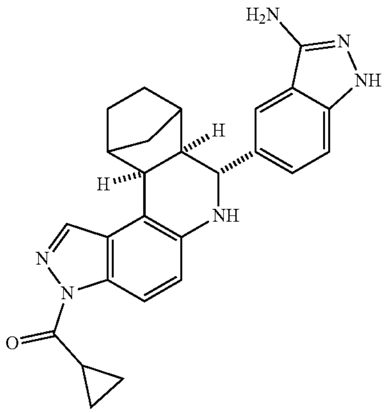

-continued

HSD1901d

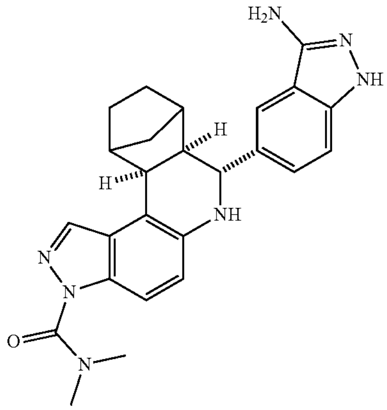

HSD1901e

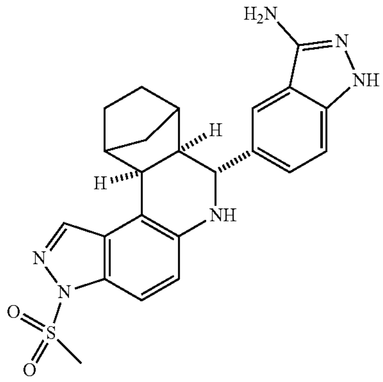

HSD1901f

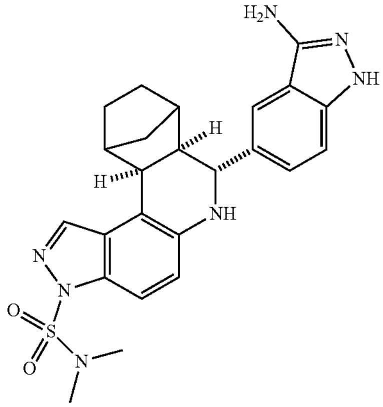

HSD1901g

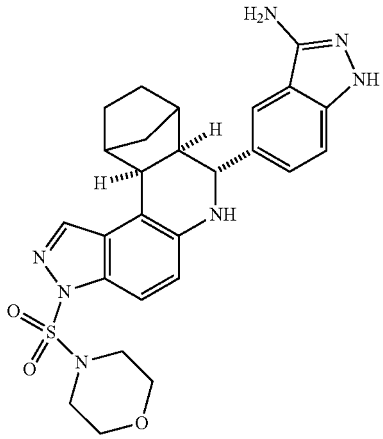

-continued
HSD1901h
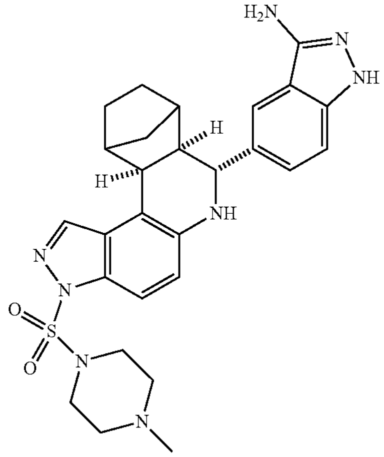
HSD1901i
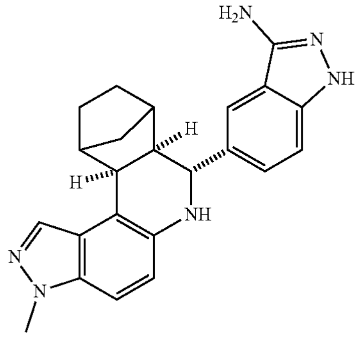
HSD1901j
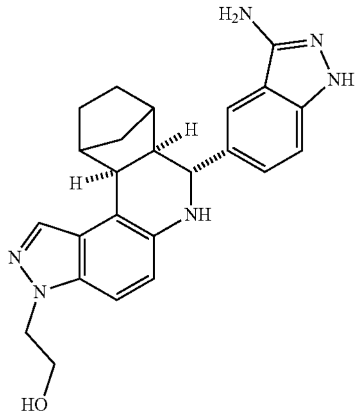
HSD1901k
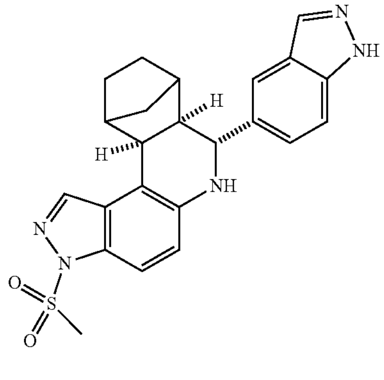
-continued
HSD5005b
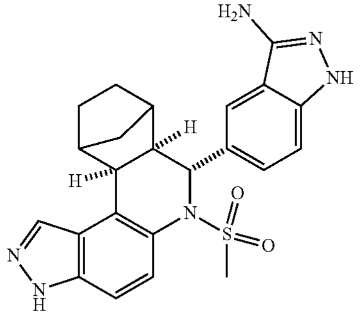
HSD5005c
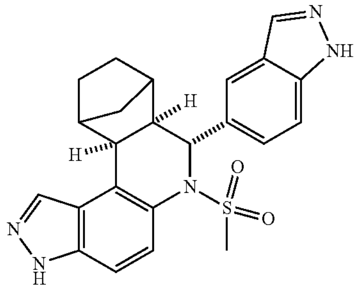
HSD5005d
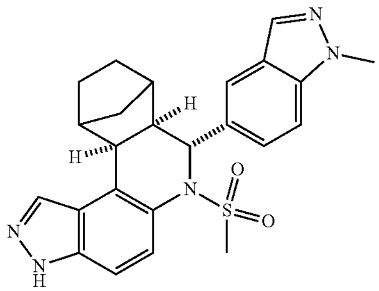
HSD5005e
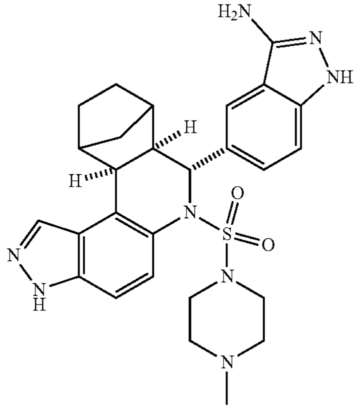

-continued
HSD5005f
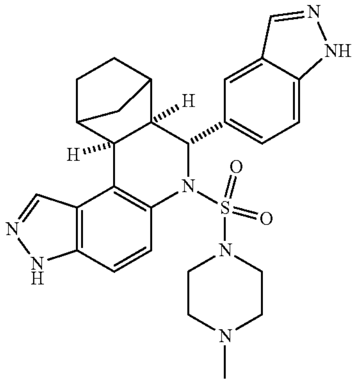
HSD5005g
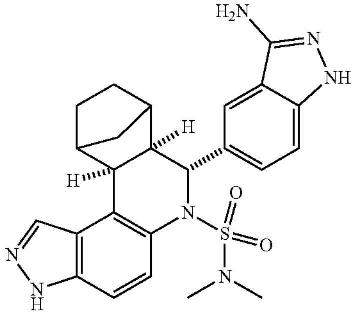
HSD5005h
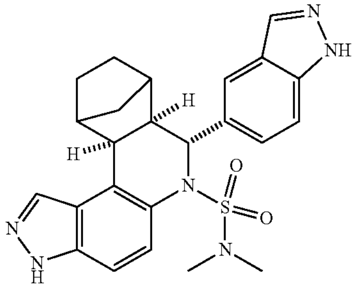
HSD5005i
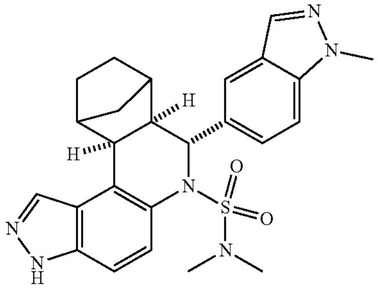
HSD5005j
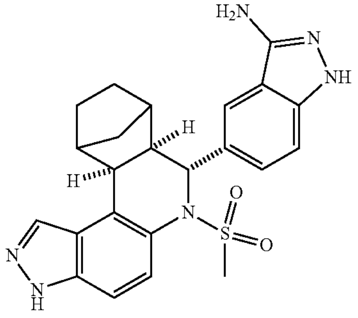
-continued
HSD5005k
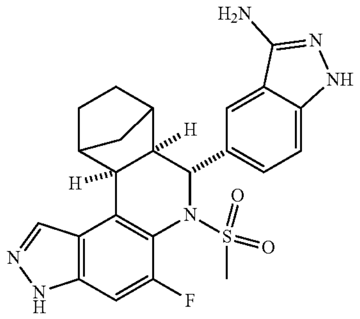
HSD5005l
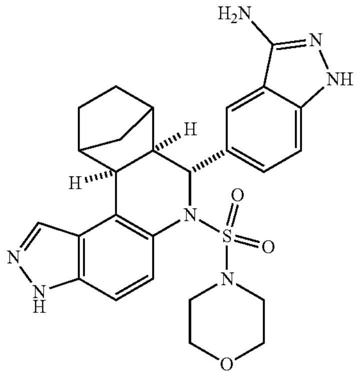
HSD5005m
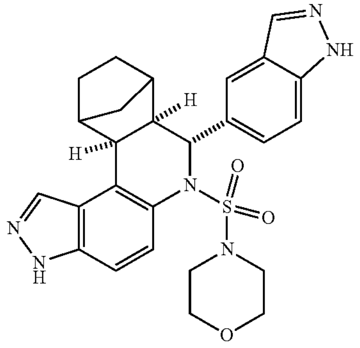
HSD5005n
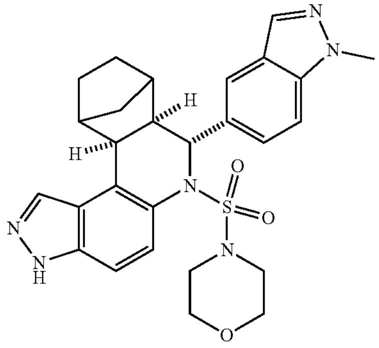

-continued
HSD5005o
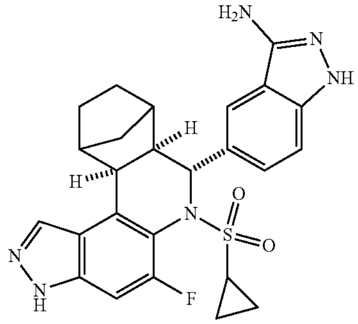
HSD5005p
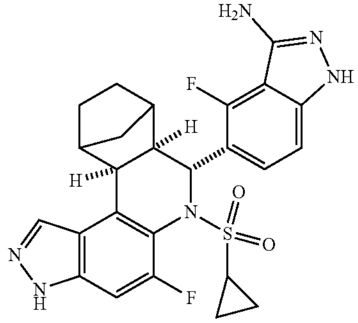
HSD1832
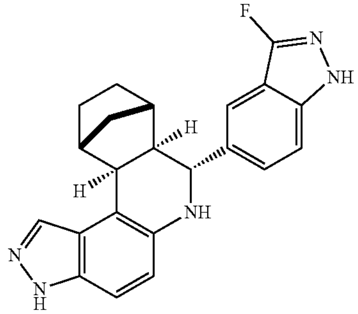
HSD1897
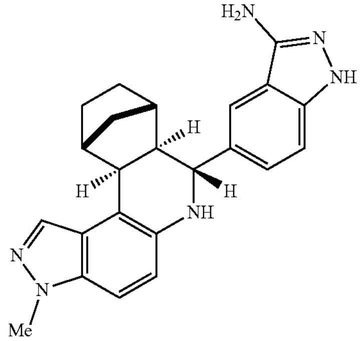
HSD5000
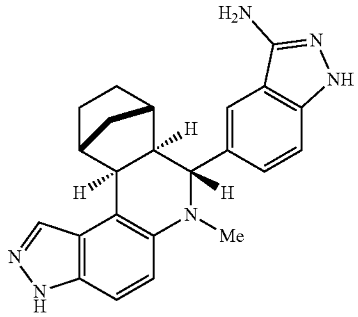
-continued
HSD1931
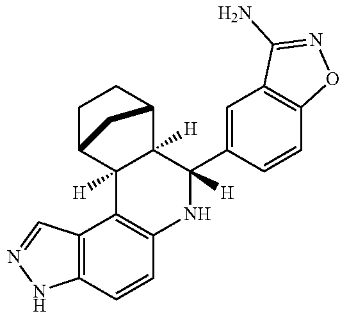
HSD5001
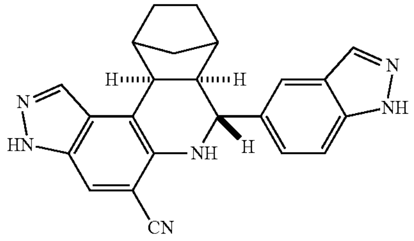
HSD5002
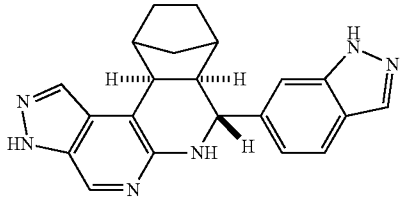
HSD5003
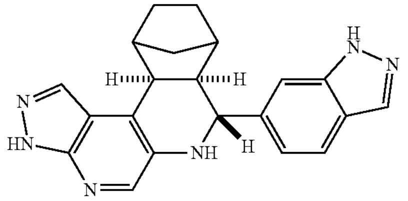
HSD5024
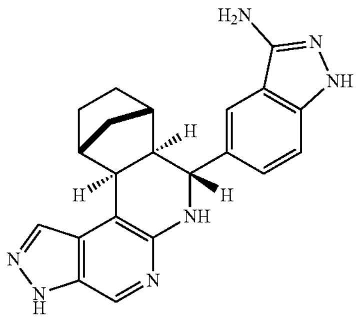

-continued

HSD1901

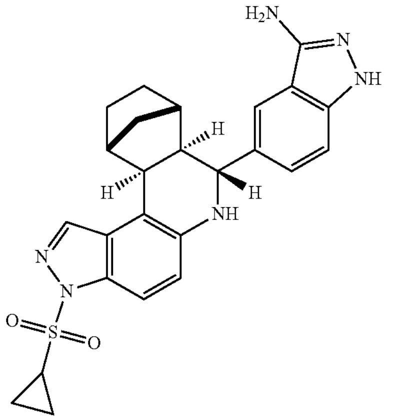

HSD5004

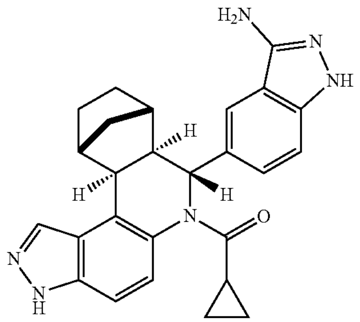

HSD5005

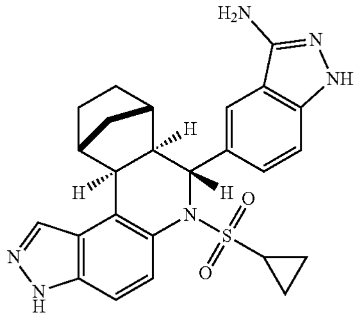

HSD1945

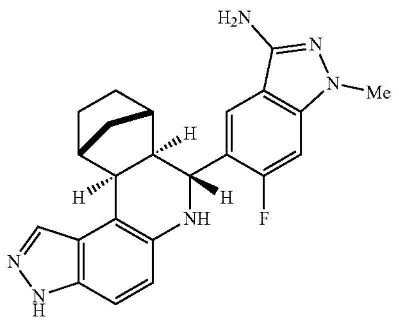

-continued

HSD5025

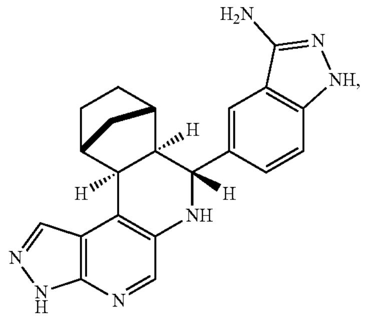

and

HSD5026

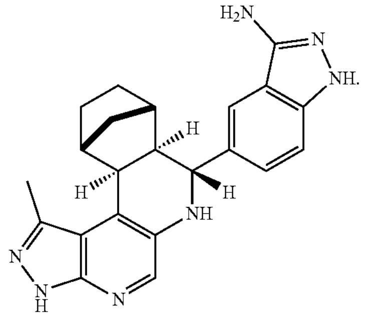

In some illustrative embodiments, this present disclosure relates to a compound having the formula (V)

(V)

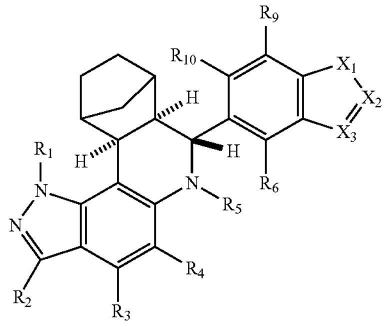

or a pharmaceutically acceptable salt thereof, wherein X, $X_1$, $X_2$, and $X_3$ are, independently, CH or N; and $R_1$, $R_2$, $R_3$, $R_4$, $R_5$, $R_6$, $R_7$, $R_8$, $R_9$, and $R_{10}$ are, independently, an alkyl, aryl, heteroalkyl, heteroaryl, halogen, CN, amide, urea, carbamate, sulfonamide, alkoxy, —$OCF_3$, —$OCHF_2$, H, D, deuterated alkyl, deuterated aryl, deuterated heteroalkyl, and deuterated heteroaryl.

In some illustrative embodiments, this present disclosure relates to a compound having the formula (V), wherein said compound comprises

S-12

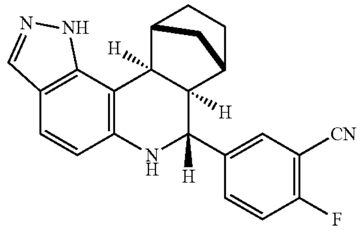

31

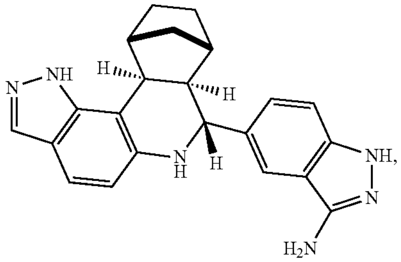

and

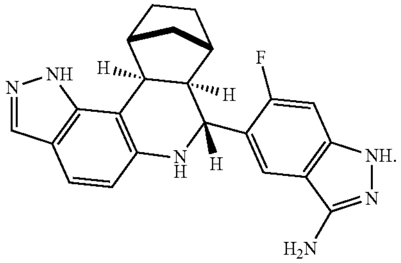

HSD4051

In some illustrative embodiments, this present disclosure relates to a compound having the formula (VI)

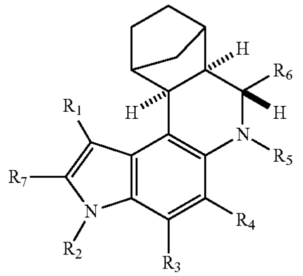

or (VII)

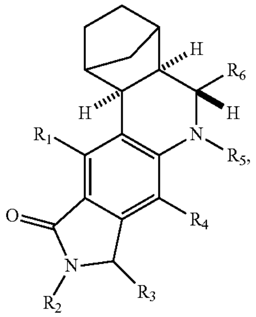

or a pharmaceutically acceptable salt thereof, wherein $R_1$, $R_2$, $R_3$, $R_4$, $R_5$, $R_6$, and $R_7$ are, independently, an alkyl, aryl, heteroalkyl, heteroaryl, halogen, CN, amide, urea, carbamate, sulfonamide, alkoxy, $-OCF_3$, $-OCHF_2$, H, D, deuterated alkyl, deuterated aryl, deuterated heteroalkyl, and deuterated heteroaryl.

In some illustrative embodiments, this present disclosure relates to a compound having the formula (VI) or (VII), wherein said compound comprises

HSD2030

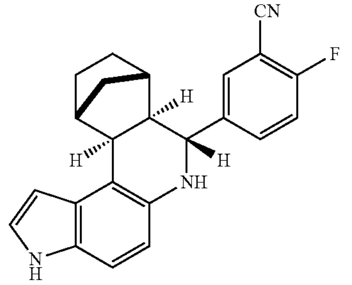

HSD4017

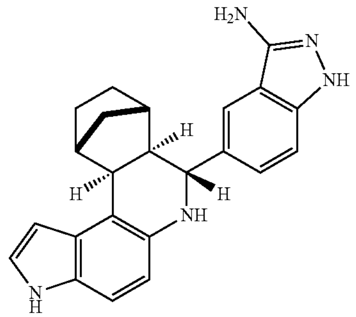

HSD5006

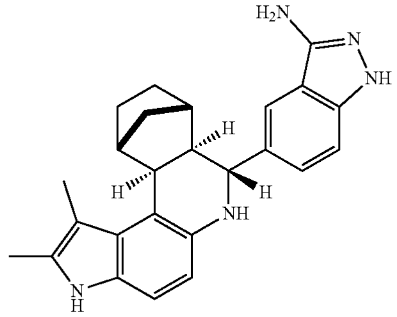

HSD5007

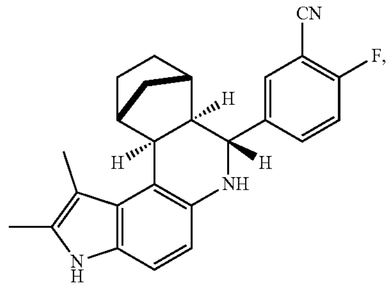

HSD5008

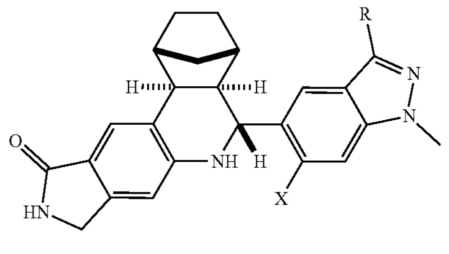

-continued

HSD5009

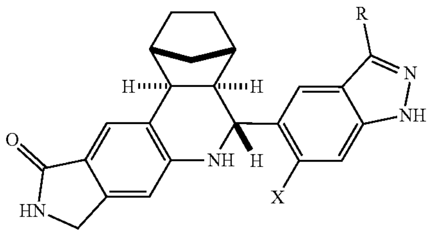

HSD5010

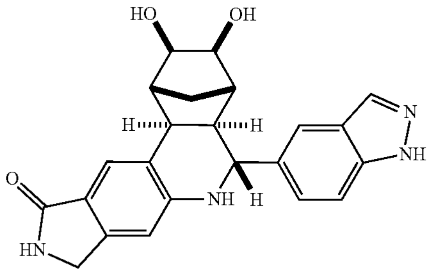

HSD1910

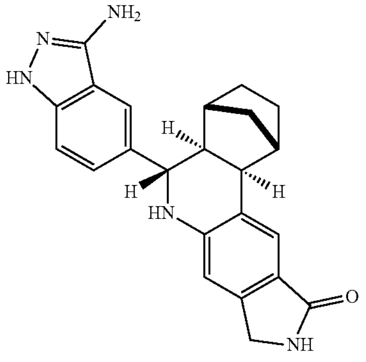

HSD1911

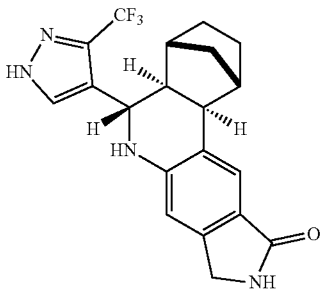

HSD1909

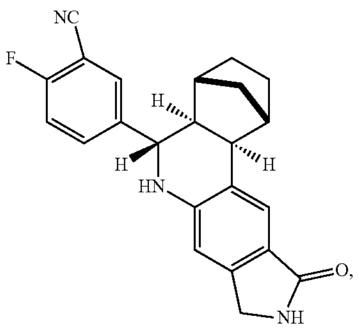

and

-continued

HSD1818

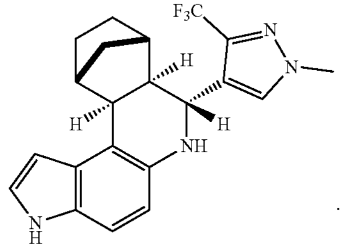

.

In some illustrative embodiments, this present disclosure relates to a compound having the formula (VIII)

(VIII)

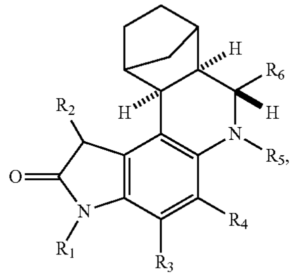

or a pharmaceutically acceptable salt thereof, wherein $R_1$, $R_2$, $R_3$, $R_4$, $R_5$, and $R_6$ are, independently, an alkyl, aryl, heteroalkyl, heteroaryl, halogen, CN, amide, urea, carbamate, sulfonamide, alkoxy, —$OCF_3$, —$OCHF_2$, H, D, deuterated alkyl, deuterated aryl, deuterated heteroalkyl, and deuterated heteroaryl.

In some illustrative embodiments, this present disclosure relates to a compound having the formula (VIII), wherein said compound comprises

HSD1927

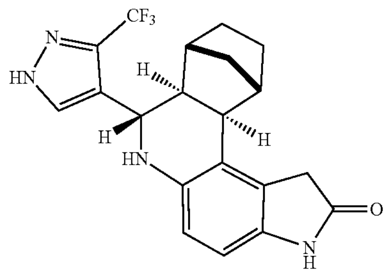

HSD1929

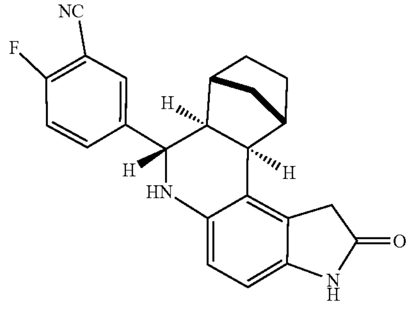

-continued

HSD1930

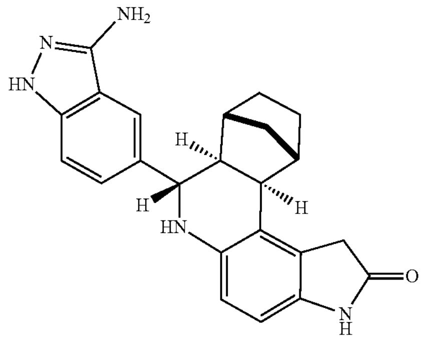

HSD5011

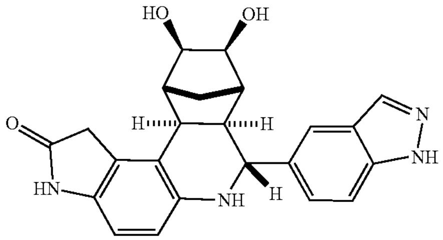

HSD5012

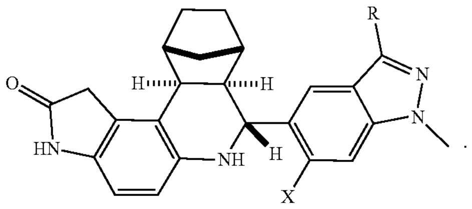

In some illustrative embodiments, this present disclosure relates to a compound having the formula (IX) or (X)

(IX)

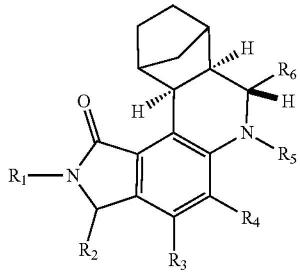

or (X)

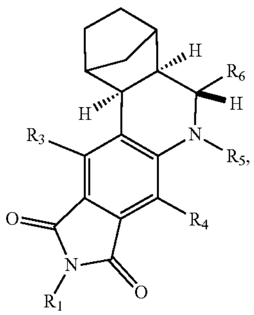

or a pharmaceutically acceptable salt thereof, wherein $R_1$, $R_2$, $R_3$, $R_4$, $R_5$, and $R_6$ are, independently, an alkyl, aryl, heteroalkyl, heteroaryl, halogen, CN, amide, urea, carbamate, sulfonamide, alkoxy, —$OCF_3$, —$OCHF_2$, H, D, deuterated alkyl, deuterated aryl, deuterated heteroalkyl, and deuterated heteroaryl.

In some illustrative embodiments, this present disclosure relates to a compound having the formula (IX) or (X), wherein said comprises

HSD1949

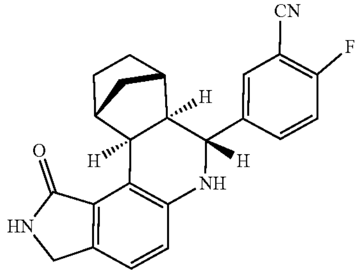

HSD1950

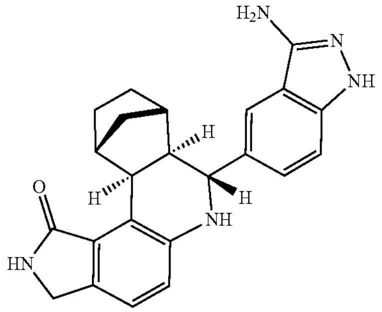

HSD1943

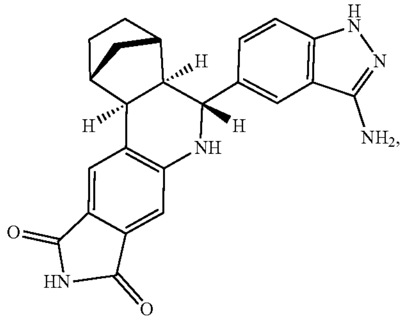

HSD1944

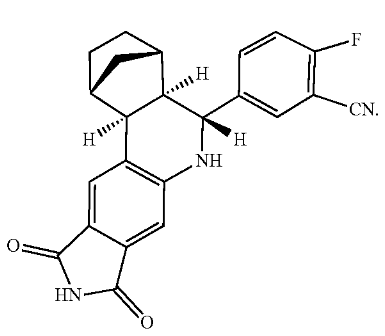

In some illustrative embodiments, this present disclosure relates to a compound having the formula (XI)

(XI)

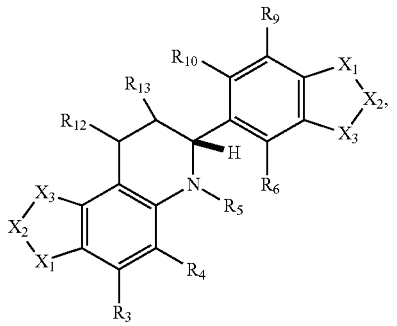

or a pharmaceutically acceptable salt thereof, wherein $X_1$, $X_2$, and $X_3$ are, independently, CH or N; and $R_1$, $R_2$, $R_3$, $R_4$, $R_5$, $R_6$, $R_7$, $R_8$, $R_9$, and $R_{10}$ are, independently, an alkyl, aryl, heteroalkyl, heteroaryl, halogen, CN, amide, urea, carbamate, sulfonamide, alkoxy, —$OCF_3$, —$OCHF_2$, H, D, deuterated alkyl, deuterated aryl, deuterated heteroalkyl, and deuterated heteroaryl.

In some illustrative embodiments, this present disclosure relates to a compound having the formula (XI), wherein said compound comprises

33

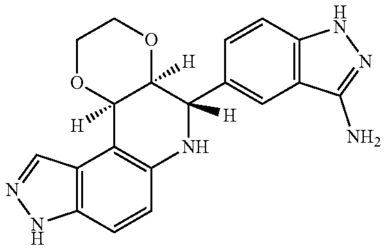

HSD2015

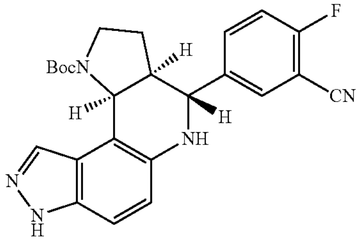

HSD2038

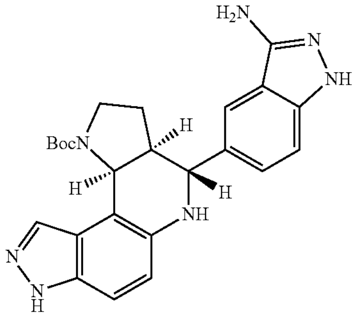

-continued

HSD2039

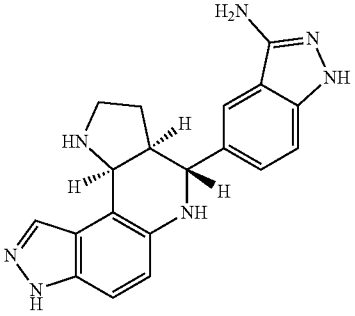

HSD1880

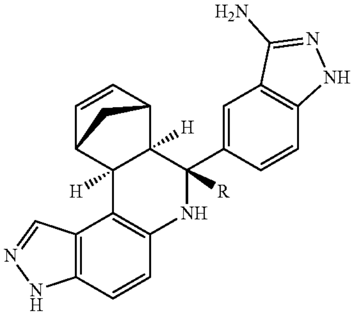

HSD1792

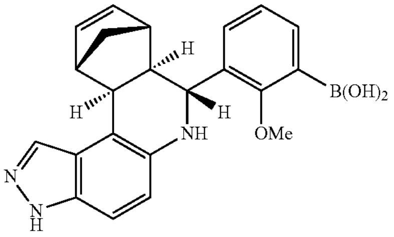

HSD1799

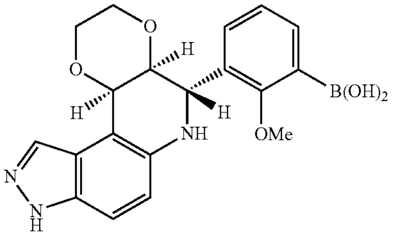

HSD2024

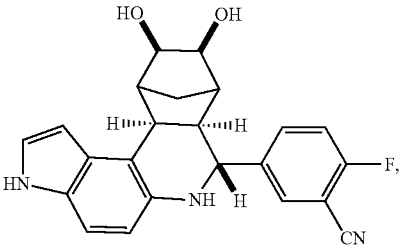

and

-continued

HSD5013

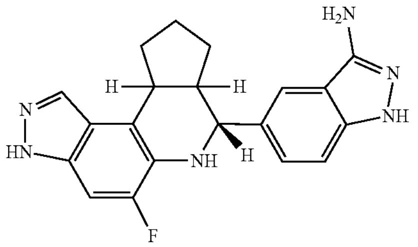

HSD5014

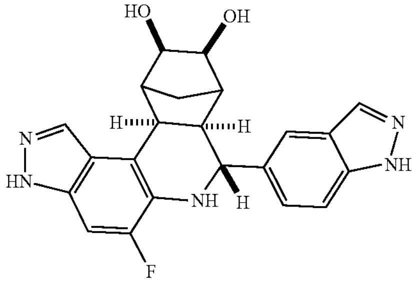

HSD5015

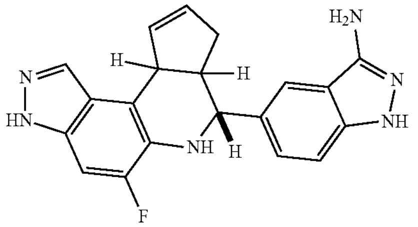

HSD5016

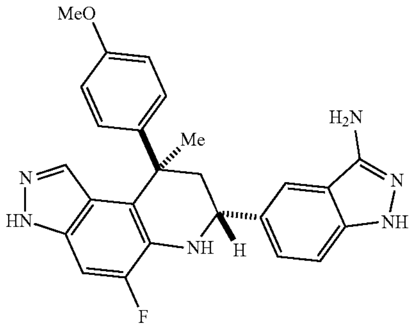

HSD5017

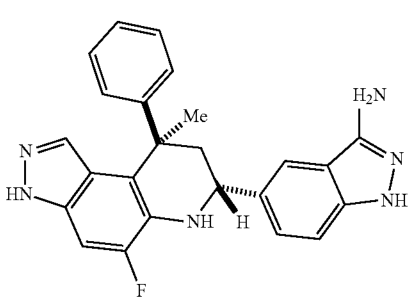

-continued

HSD5018

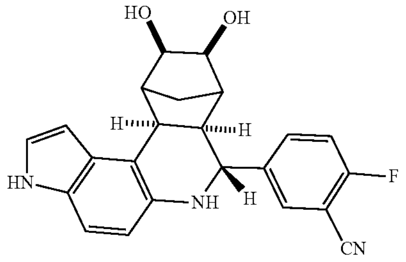

HSD1831

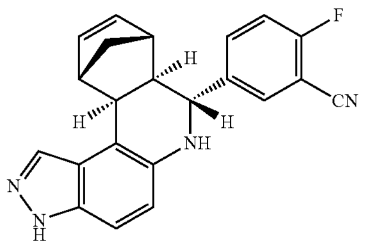

HSD5019

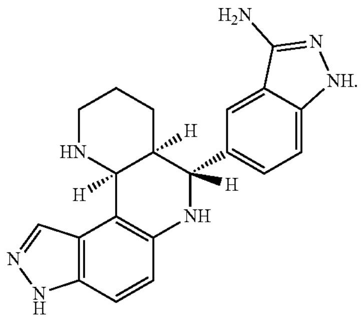

In some illustrative embodiments, this present disclosure relates to a compound having the formula (XII)

(XII)

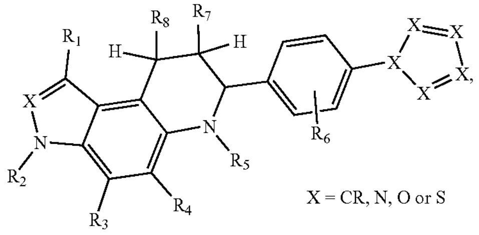

or a pharmaceutically acceptable salt thereof, wherein X is CR, N, O, or S; and R, $R_1$, $R_2$, $R_3$, $R_4$, $R_5$, $R_6$, $R_7$, and $R_8$ are, independently, an alkyl, aryl, heteroalkyl, heteroaryl, halogen, CN, amide, urea, carbamate, sulfonamide, alkoxy, —$OCF_3$, —$OCHF_2$, H, D, deuterated alkyl, deuterated aryl, deuterated heteroalkyl, and deuterated heteroaryl.

HSDB1
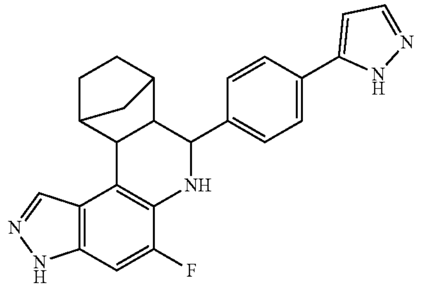
HSDB2
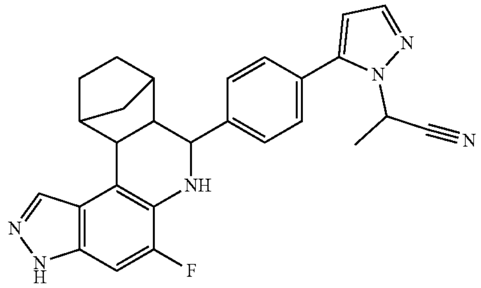
HSDB3
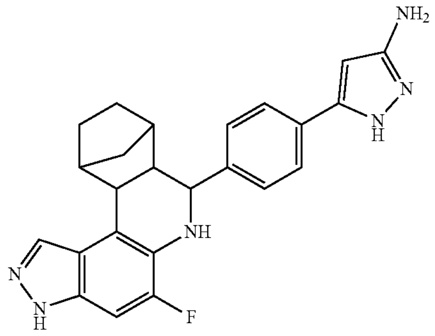
HSDB4
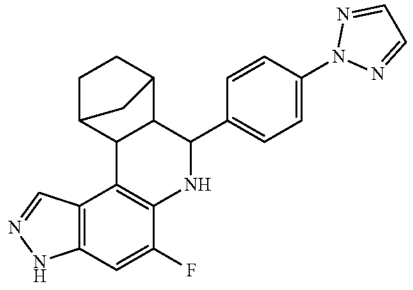
HSDB5
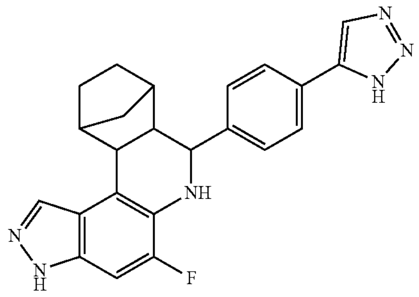
-continued
HSDB6
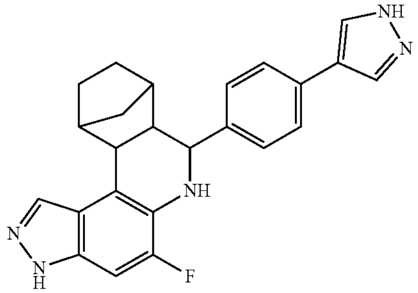
HSDB7
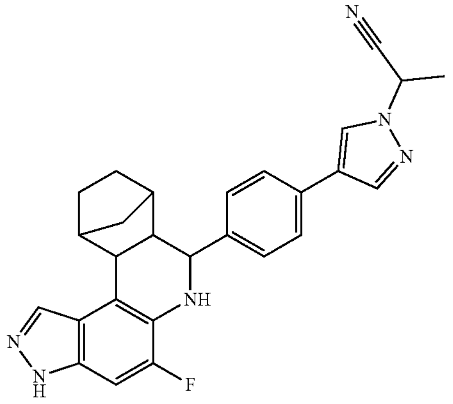
HSDB8
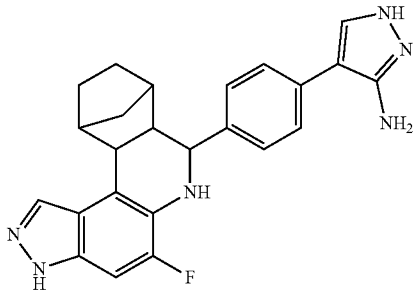
HSDB9
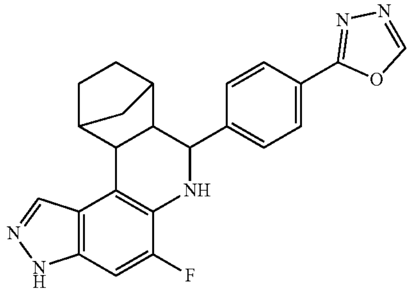
HSDB10
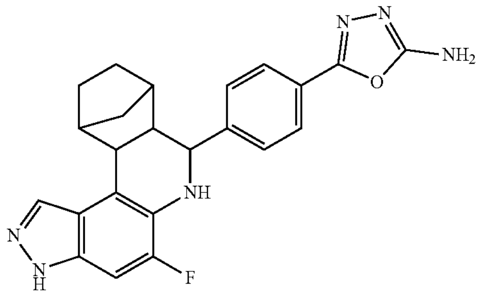

In some illustrative embodiments, this present disclosure relates to a compound having the formula (XII), wherein said compound comprises
HSDC1m
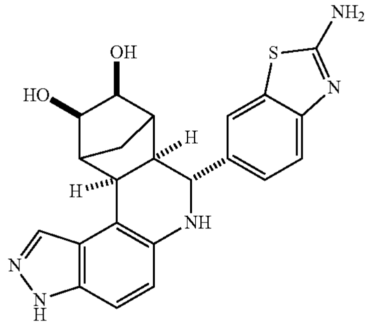
HSDC1n
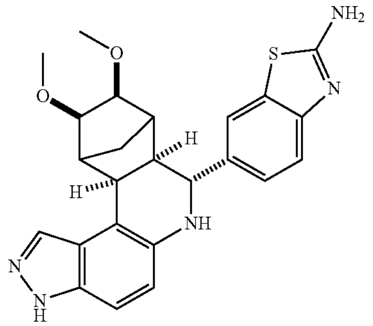
HSDC1o
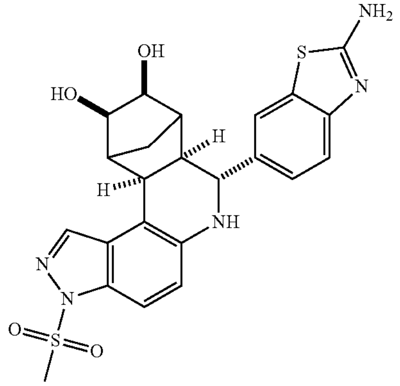
HSDC1p
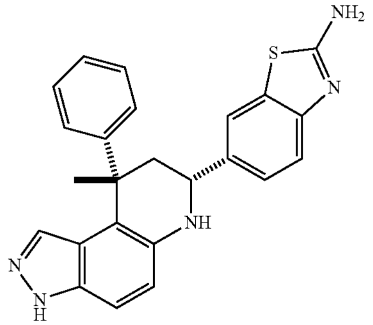
-continued
HSDC1q
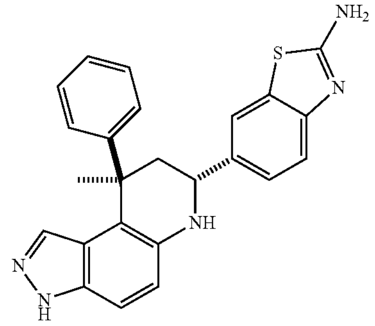
HSDC1
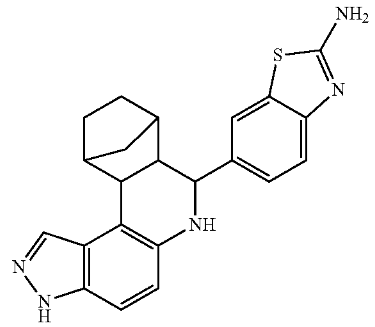
HSDC2
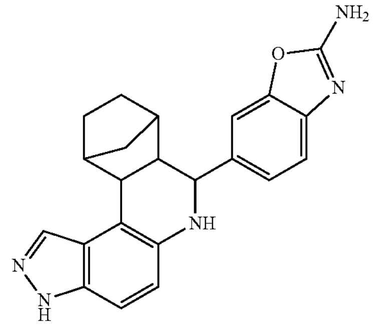
HSDC3
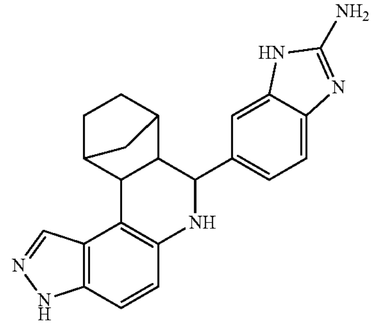
HSDC4
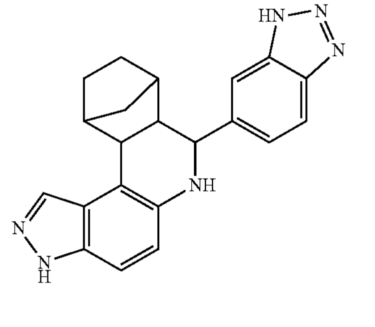

-continued
HSDC5
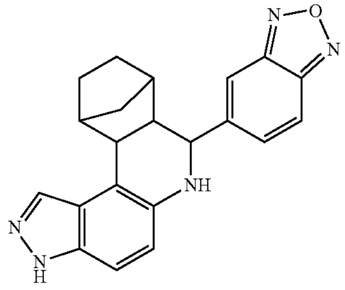
HSDC6
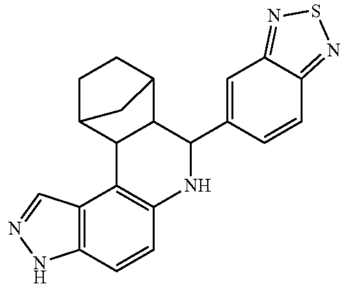
HSDC7
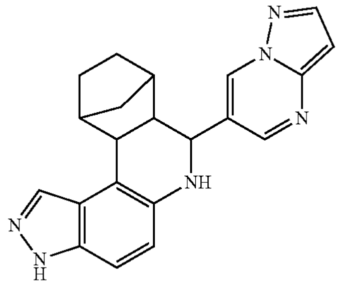
HSDC8
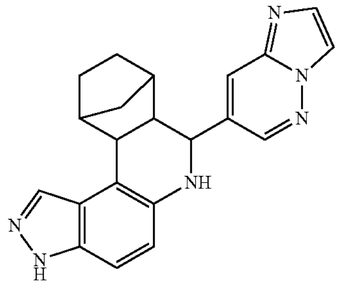
HSDC9
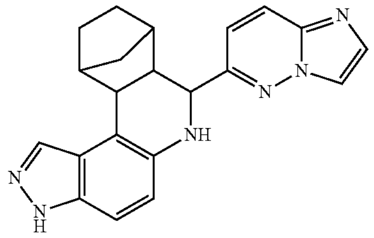
-continued
HSDC10
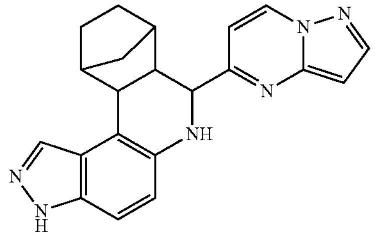
HSDC11
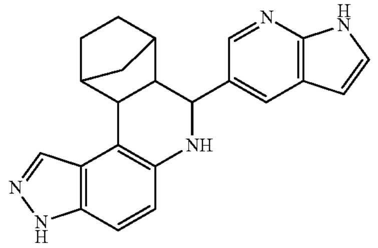
HSDC12
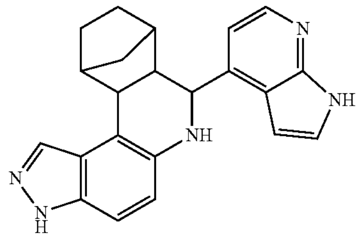
HSDC13
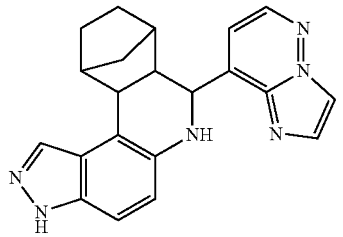
HSDC14
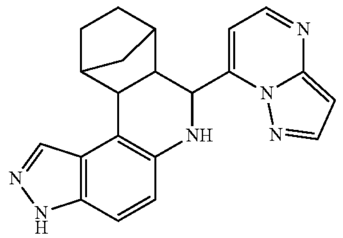
HSDC15
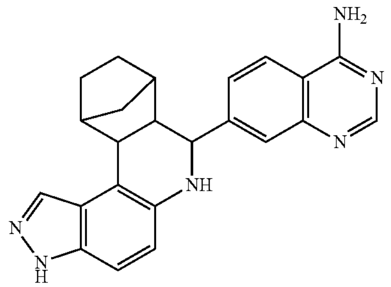

-continued
HSDC16
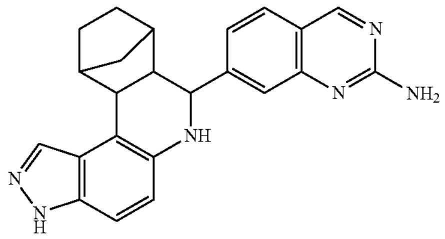
HSDC1b
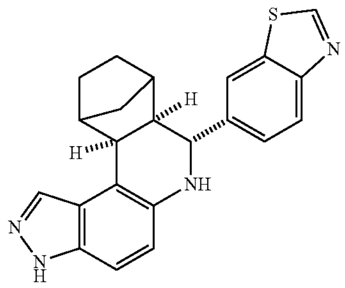
HSDC1c
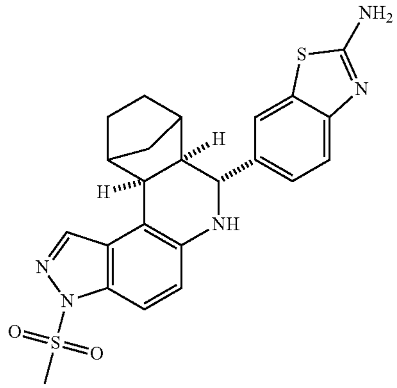
HSDC1d
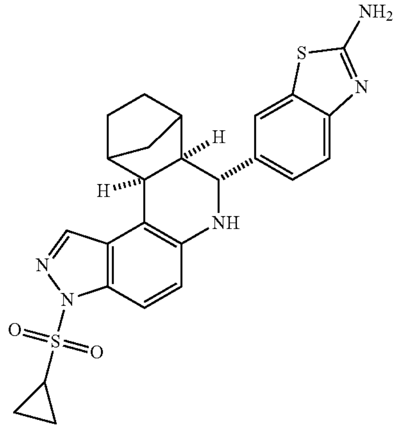
-continued
HSDC1e
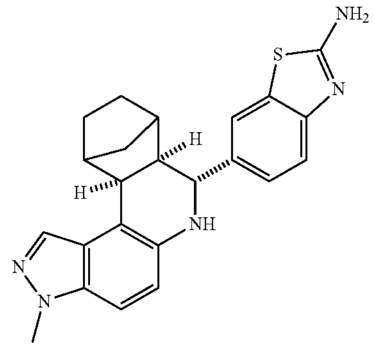
HSDC1f
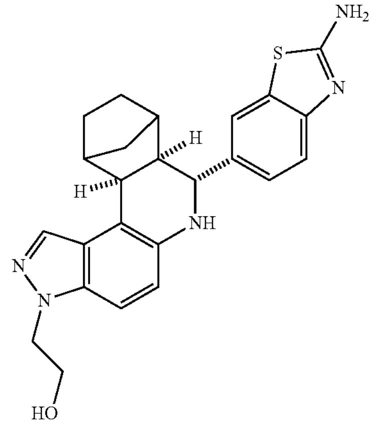
HSDC1g
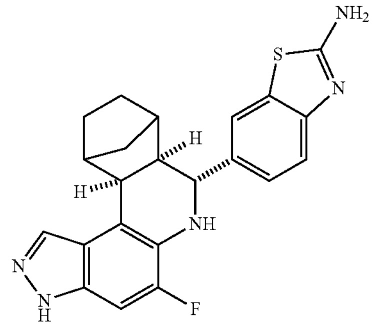
HSDC1h
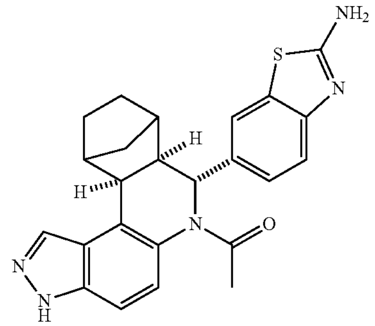

-continued
HSDC1i
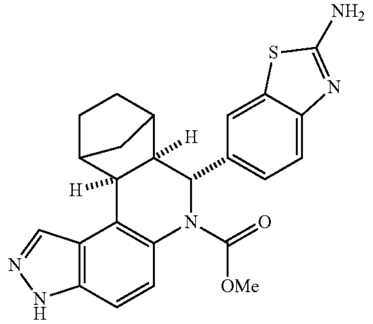
HSDC1j
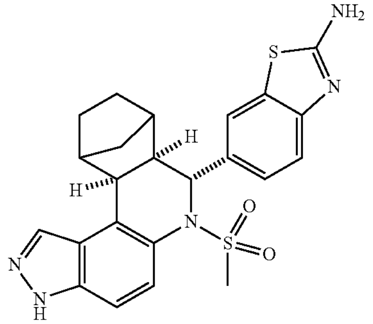
HSDC1k
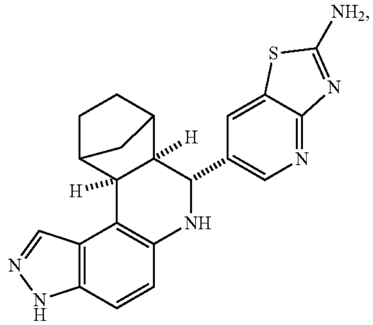
and
HSDC1r
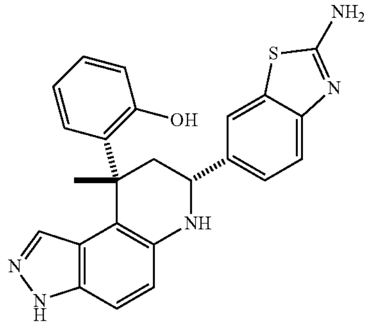
HSDC1s
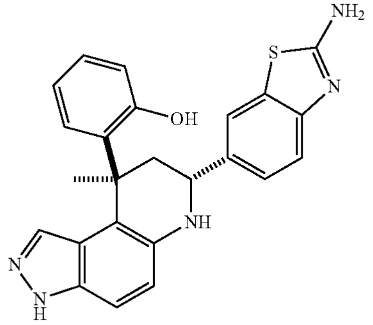
-continued
HSDC1t
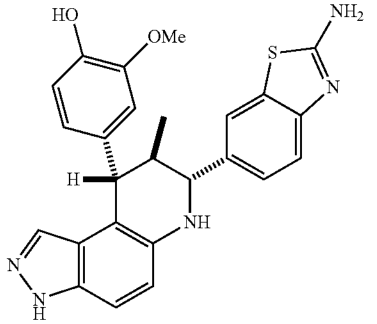
HSDC1u
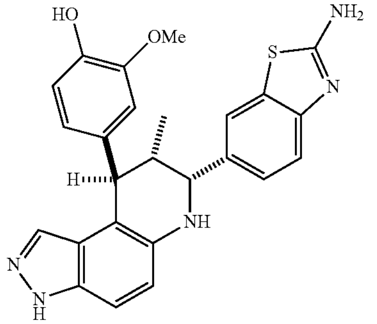
HSDC1v
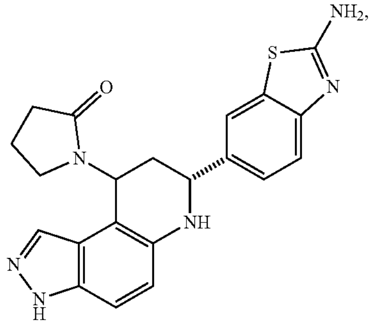
,
HSDD1
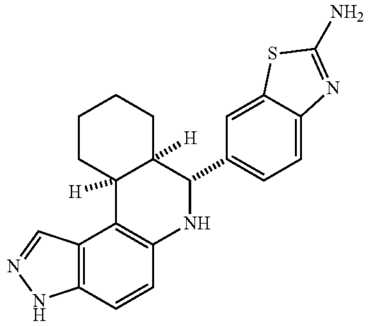
HSDD2
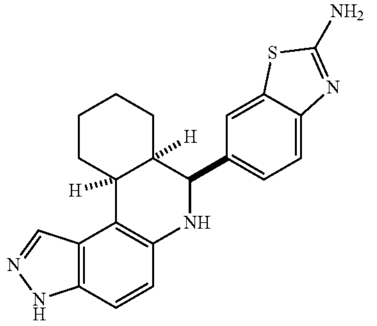

-continued
HSDD3
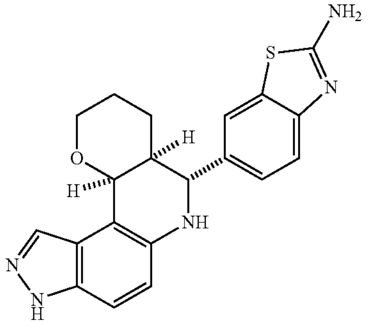
HSDD4
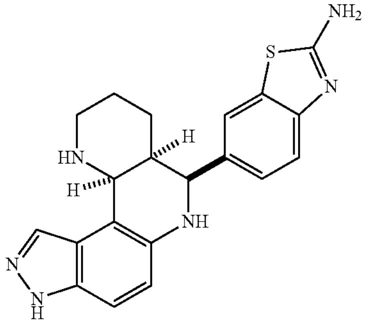
HSDD5
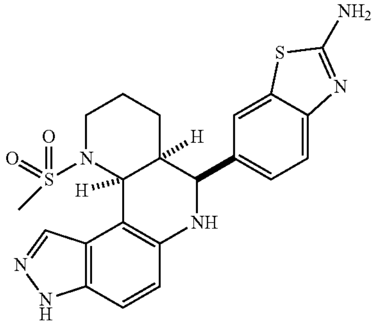
HSDD6
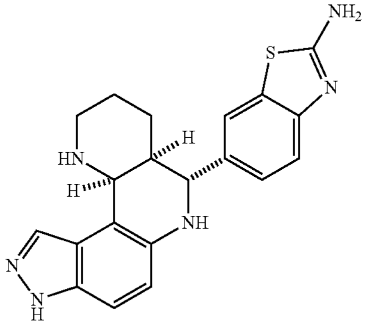
HSDD7
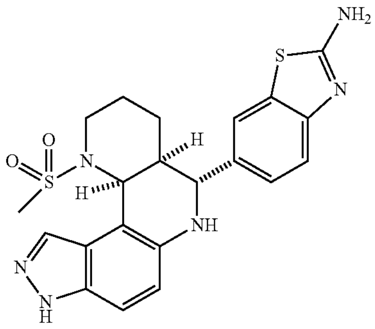
-continued
HSDD8
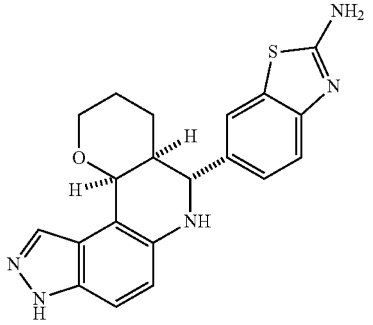
HSDD9
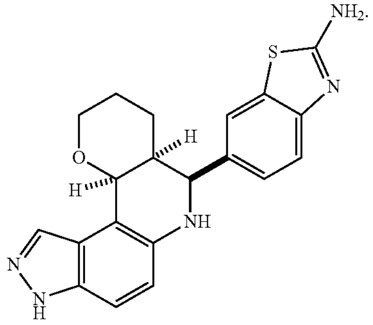
In some illustrative embodiments, this present disclosure relates to a compound as disclosed herein, wherein said compound is a prodrug comprising
HSD5021c
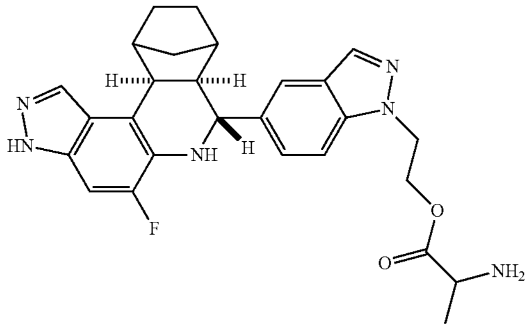
HSD5021d
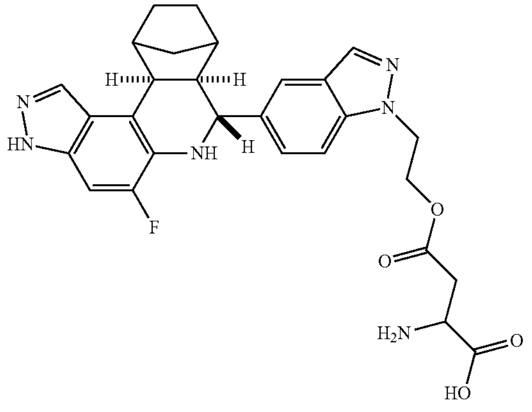

-continued
HSD5021e
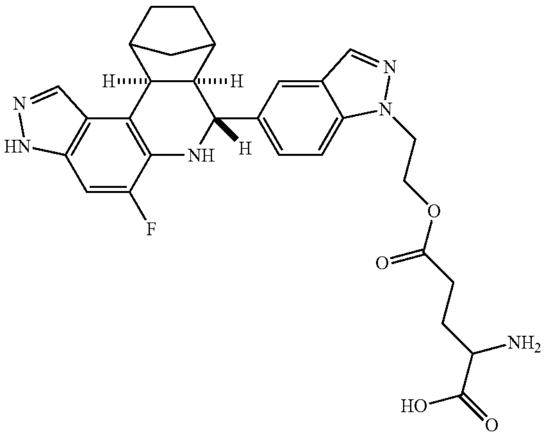
HSD5021f
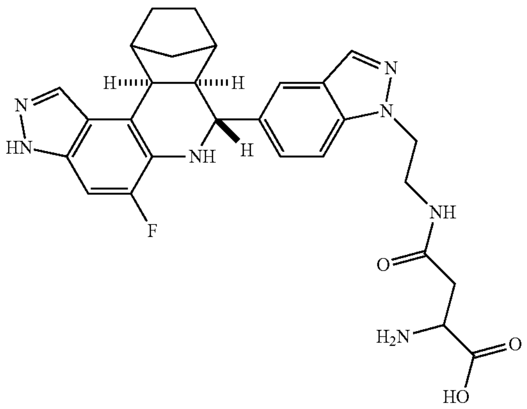
HSD5021g
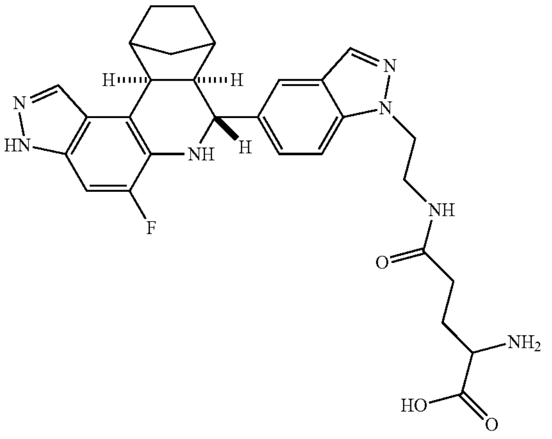
HSD5021h
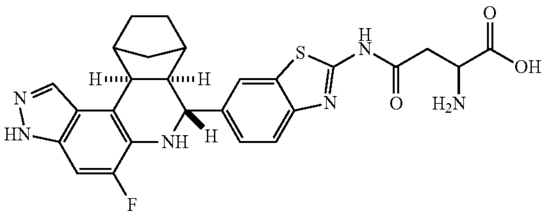
-continued
HSD5021i
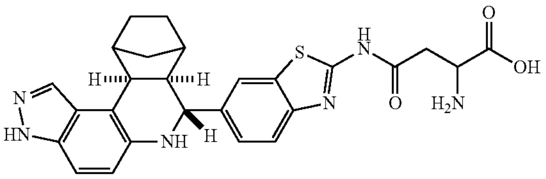
HSD5021j
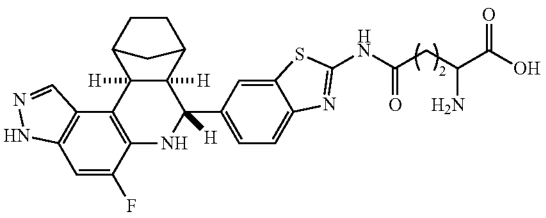
HSD5021k
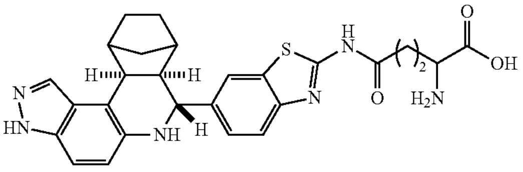
and
HSD5020
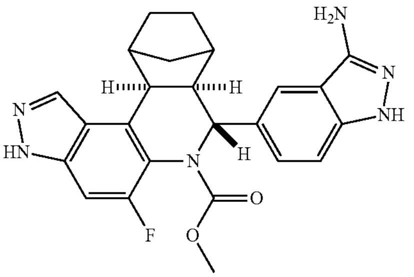
HSD5021
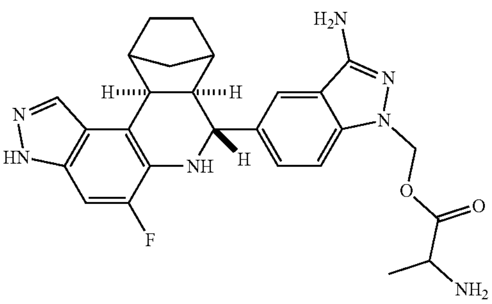

-continued

HSD5022

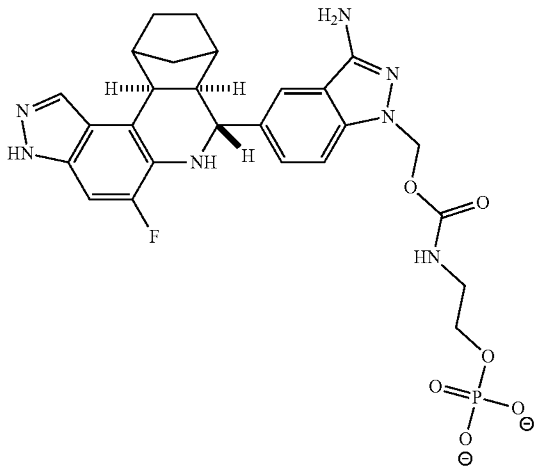

HSD5023

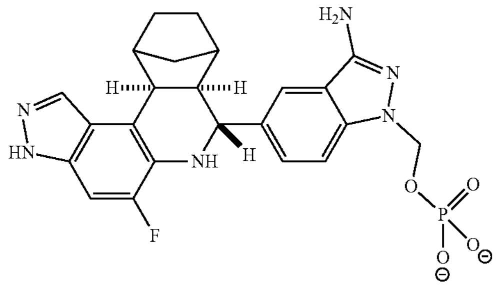

HSD5020b

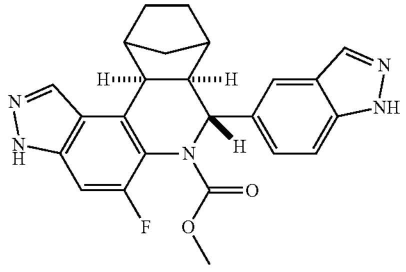

HSD5021b

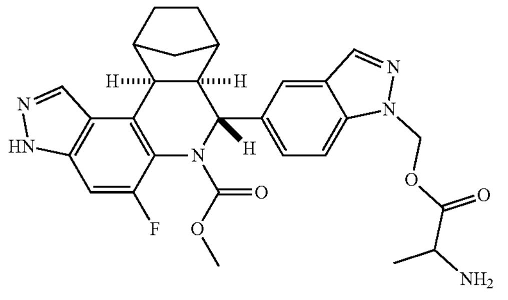

-continued

HSD5022b

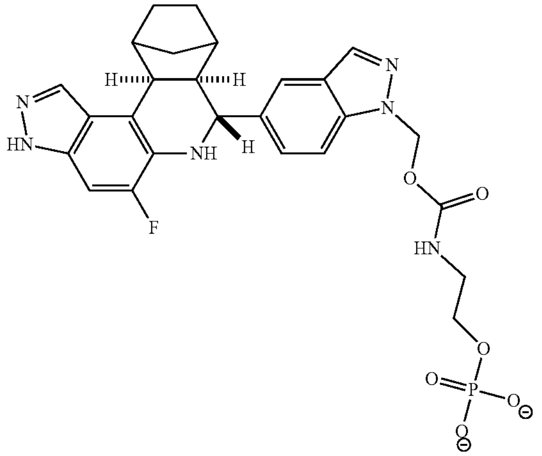

HSD5023b

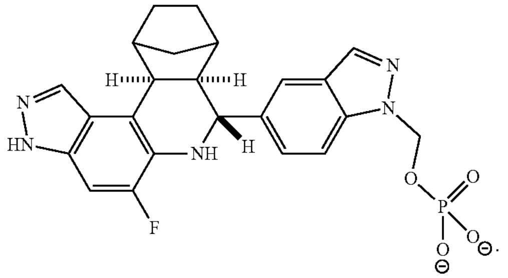

In some illustrative embodiments, this present disclosure relates to a pharmaceutical composition comprising one or more compounds as disclosed herein, or a pharmaceutically acceptable salt, N-oxide, hydrate, solvent, tautomer, or optical isomer thereof, and a pharmaceutically acceptable carrier or diluent.

In some illustrative embodiments, this present disclosure relates to a pharmaceutical composition comprising one or more compounds as disclosed herein, being conjugated to a targeting group, including amino acids, or a group that aids the degradation of a binding protein target, such as PROTAC.

In some other illustrative embodiments, this present disclosure relates to a method of treating, inhibiting, suppressing, or reducing the severity of cancer in a subject in need thereof, wherein the method comprises administering to the subject a therapeutically effective amount of one or more compounds as disclosed herein, or a pharmaceutically acceptable salt, N-oxide, hydrate, solvate, tautomer, or optical isomer thereof, or a pharmaceutical composition containing one or more compounds as described herein.

In some other illustrative embodiments, this present disclosure relates to a method of treating, inhibiting, suppressing, or reducing the severity of cancer in a subject in need thereof, wherein said cancer is selected from the group consisting of acute myeloid leukemia, chronic myeloid leukemia, ovarian cancer, cervical cancer, pancreatic cancer, breast cancer, brain cancer, skin cancer, lung cancer, prostate cancer, lymphoma, leukemia, colon cancer, head cancer, neck cancer, thyroid cancer, kidney cancer, liver cancer, and stomach cancer.

In some other illustrative embodiments, this present disclosure relates to a treatment delivery apparatus comprising a delivery mechanism selected from the group consisting of:

capsules, polypills, tablets, transdermal patches, dietary supplements, or a combination thereof; and at least one dosage of a composition contained in the delivery mechanism, wherein the composition is a therapeutically effective amount of a compound or a combination of compounds as disclosed herein, or a pharmaceutically acceptable salt, N-oxide, hydrate, solvate, tautomer, or optical isomer thereof, or a pharmaceutical composition thereof.

In some other illustrative embodiments, this present disclosure relates to a method of treating, inhibiting, suppressing, or reducing the severity of a disease or a disorder associated with protein kinase in a subject in need thereof, wherein the method comprises administering to the subject a therapeutically effective amount of a compound disclosed herein, or a pharmaceutically acceptable salt, N-oxide, hydrate, solvate, tautomer, or optical isomer thereof, or a pharmaceutical composition thereof.

In some other illustrative embodiments, this present disclosure relates to a pharmaceutical composition comprising one or more of the claimed compounds, or a pharmaceutically acceptable salt thereof, together with one or more carriers, excipients, or diluents.

Multi-component reaction (MCR) is often used to rapidly assemble complex compounds for drug screening. Recently we used the Doebner MCR to make a library of 3H-pyrazolo[4,3-f]quinoline compounds and showed that these compounds potently inhibited various cancer cells via the inhibition of kinases. In an effort to escape from flatland, we used the analogous Povarov MCR to prepare a new library containing tetrahydro-3H-pyrazolo[4,3-f]quinoline core, which has higher relative fraction of sp3-bonded carbon (Fsp3) and first tested the library against MDA-MB-231 (a triple negative breast cancer, TNBC, cell line). Some of the tetrahydro-3H-pyrazolo[4,3-f]quinoline-containing compounds, bearing 3-aminoindazolyl group, potently inhibited MDA-MB-231. Some of these compounds were evaluated against NCI60 cell lines and some, such as 22, 23 and 27 (which were substituted with fluorine) inhibited melanoma, renal, breast, ovarian and leukemia cancer cell lines with GI50 values as low as 30 nM. The tetrahydro-3H-pyrazolo[4,3-f]quinoline core is therefore a new scaffold that could be developed into potent anticancer therapeutics against difficult-to-treat cancers.

TABLE 1

Synthesis of first series analogs.

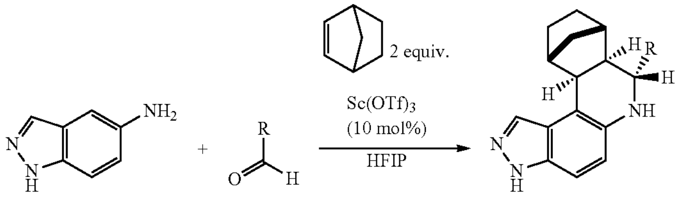

1 mmol 1 mmol exo-exo

| Compound | R | % Inhibition MDA-MB-231 | Yield (%) |
|---|---|---|---|
| 1 | 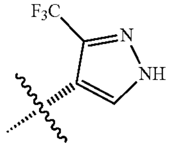 | 5 | 45 |
| 2 | 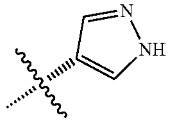 | 12 | 52 |
| 3 | 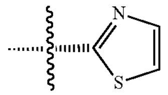 | 13 | 36 |
| 4 | 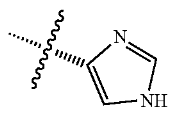 | 14 | 49 |
| 5 | 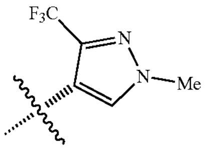 | 70 | 37 |

TABLE 1-continued
Synthesis of first series analogs.
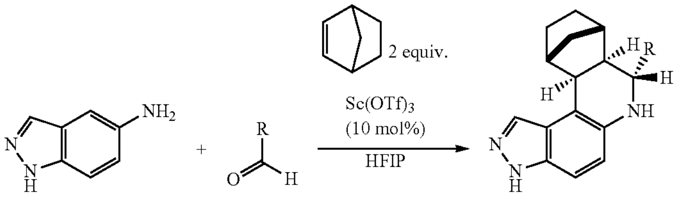
1 mmol 1 mmol exo-exo
| Compound | R | % Inhibition MDA-MB-231 | Yield (%) |
| --- | --- | --- | --- |
| 6 | 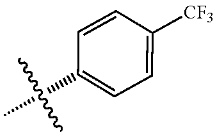 | 21 | 42 |
| 7 | 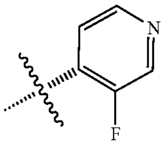 | 11 | 53 |
| 8 | 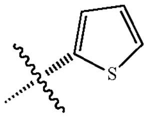 | 13 | 47 |
| 9 | 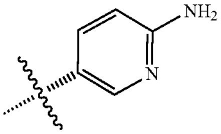 | 18 | 53 |
| 10 | 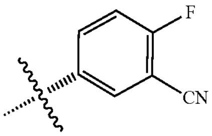 | 3 | 43 |
| 11 | 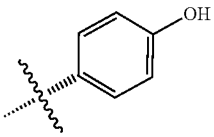 | 0 | 45 |
| 12 | 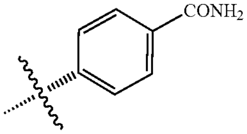 | 17 | 34 |
| 13 | 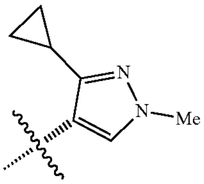 | 0 | 46 |

TABLE 1-continued
Synthesis of first series analogs.
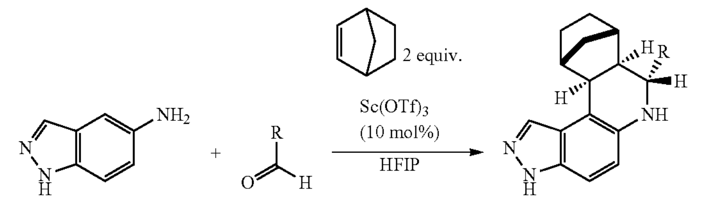
1 mmol 1 mmol exo-exo
| Compound | R | % Inhibition MDA-MB-231 | Yield (%) |
|---|---|---|---|
| 14 | 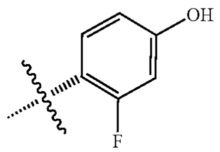 | 11 | 66 |
| 15 | 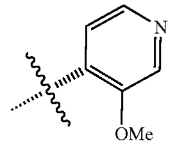 | 12 | 47 |
| 16 | 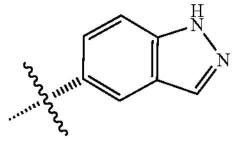 | 78 | 33 |
| 17 | 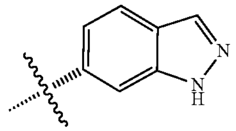 | 91 | 37 |
Scheme 1. Three-component Povarov reaction of 5-aminoindazole, aldehyde and norbornene.
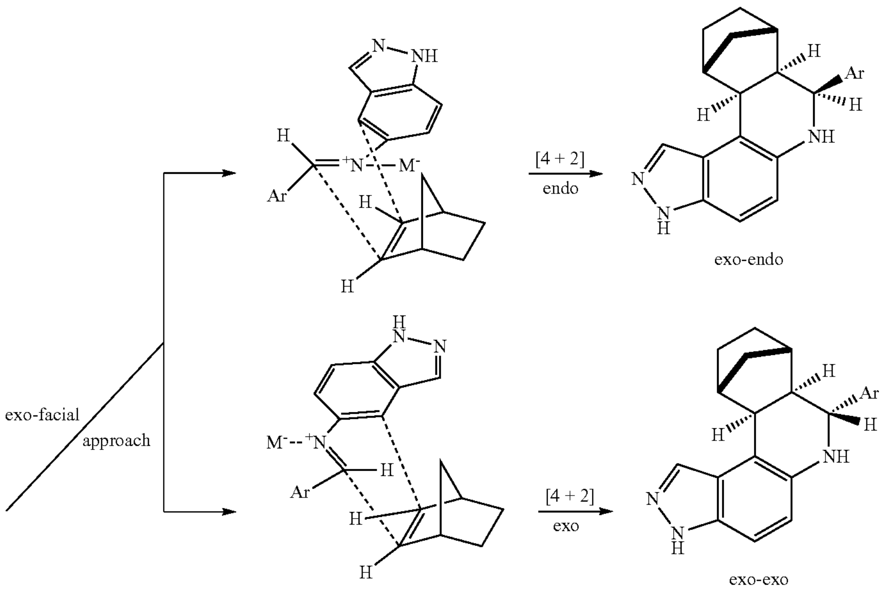

-continued

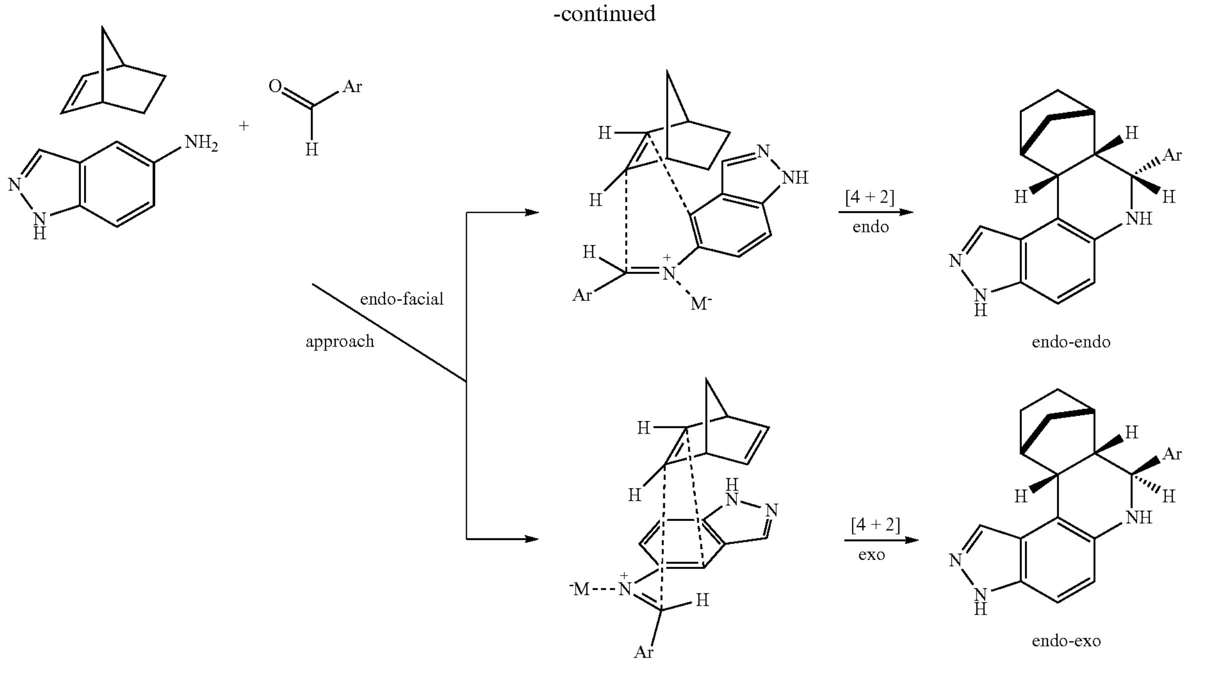

Multi-component reactions (MCRs), such as Ugi,[6] Gewald,[7] Groebke-Blackburn-Bienaymé,[4] Hantzsch,[8] Biginelli,[9] Passerini[10] etc. have been routinely used to make diverse libraries for biological screening and many compounds with anticancer, antibiotics, antiviral etc. properties have been discovered from such libraries.[1-5] In addition to facilitating compound library synthesis, MCRs have also been used to streamline drug synthesis, highlighted by classic synthesis of the blockbuster drug nifedipine via a Hantzsch three component reaction (3CR).[11]

Other pertinent examples are the syntheses of HIV protease inhibitors crixivan and telaprevir, which can be synthesized on scale utilizing Ugi reactions.[12] The Groebke-Blackburn-Bienayé,[4] a relatively newer MCR, was used for the synthesis of GLPG1690, an autotaxin inhibitor that is in clinical development for the treatment of IPF (idiopathic pulmonary fibrosis). [13]The Povarov reaction is another robust multicomponent reaction, which produces tetrahydroquinoline core (a common scaffold found in many biologically active compounds or drugs, see FIG. 1).[14-24] For example, the FDA approved drug Talazoparib (Talzenna, Pfizer Inc), a poly-(ADP-ribose) polymerase-1/2 (PARP-1/2) oral inhibitor contains a tetrahydroquinoline core (see FIG. 1A). Talazoparib is used for the treatment of germline BRCA-mutated HER2-negative locally advanced and metastatic breast cancer.[25] BMS-593214, another compound that contains the tetrahydroquinoline core (FIG. 1A) is a factor V11a inhibitor and an anticoagulant compound. Others have used the Povarov reaction to make compounds with various biological properties. For example Jiang and co-workers reported that the furano[3,2-c]tetrahydroquinoline 10a, with an all cis stereochemistries across the tetrahydroquinoline stereogenic centers (FIG. 1A), inhibited various cancer cell lines with IC50 values of 2.5 μM to 50 μM.[26] Almansa and co-workers also reported novel hexahydro-2H-pyrano[3,2-c]quinolones, synthesized via Povarov, which are selective $\sigma_1$ receptor ligands with potential application as analgesics.[27]

We decided to make a novel library for anticancer activity screening by combing the privileged indazole (see FIG. 1B for FDA-approved drugs containing indazole core) with tetrahydroquinoline to afford tetrahydro-3H-pyrazolo[4,3-f]quinoline, which we rationalized could be readily synthesized via Povarov reaction. The first series of compounds were initially screened for growth inhibition of MDA-MB-231 (a triple negative breast cancer, TNBC, cell line). We selected TNBC cell for initial screening because TNBC patients (who comprise ~11% of all breast cancer patients) have worst prognosis.[28] For metastatic TNBC, the median survival is only 13 months[29] and therefore we were motivated to find lead compounds for this indication.

For the synthesis of the Povarov library, we modified the typical previously protocols, which used dichloromethane and acetonitrile solvents,[30,31] and instead used hexafluroisopropanol (HFIP) as solvent and 10 mol % scandium triflate as Lewis catalyst. The switch to HFIP was needed because our starting amine, 5-aminoindazole and its intermediate, imine, had limited solubility in the traditional solvents dichloromethane and acetonitrile. Treating 5-aminoindazole and corresponding aldehydes and bicyclo[2.2.1]hept-2-ene (norbornene) as an activated alkene source afforded tetrahydroquinoline-containing compounds in 33-66% yields after 8 to 12 h of stirring at room temperature. Excitingly, only one diastereomer (see FIG. 2) was obtained in the Povarov reactions after column chromatography (up to 66% yield) and single crystal X-ray diffraction analysis of one of the compounds, 1, indicated that the H7A and H12A protons are trans to H13A proton in the major diastereomer, which has exo-exo relative sterochemistry (see FIG. 2). Out of four possible diasteroisomer products in the Povarov reaction of 5-aminoindazole with 1-norbornene, exo-exo diastereomer was observed as major product probably because of favorable exo-facial approach of cyclization (see Scheme 1). This result is in agreement with literature precedent, which also utilized norbornene in Povarov reactions,[30]

Figure 3:
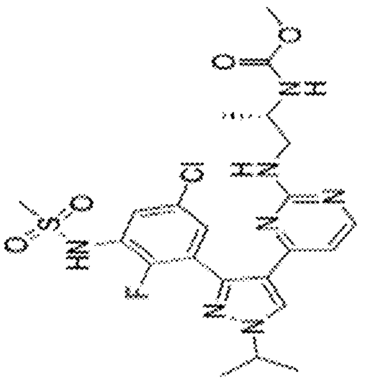
FIG. 3 shows the current pharmaceutical drugs containing fluorines.
Figure 3:
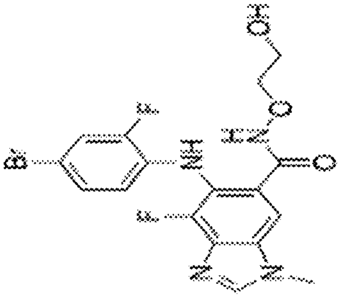
Figure 3:
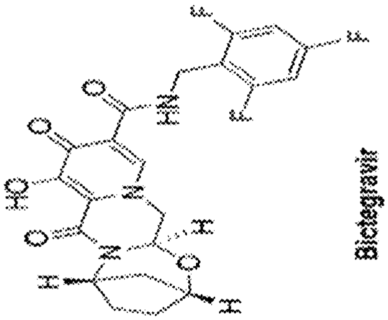
Figure 3:
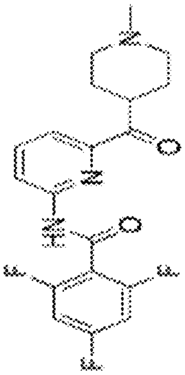

The first series of seventeen compounds was obtained by reaction 5-aminoindazole and norbornene with seventeen different aldehydes (see Table 1). The inhibitions of MDA-MB-231 viability by the compounds at 1 μM concentration were evaluated by first treating the cancer cell line with compounds and incubating for 72 hours and using the MTT assay to evaluate growth inhibition.[31] The anticancer properties of the compounds depended heavily on the nature of the starting aldehyde used for the synthesis. Compounds 16 and 17, bearing 5-indazolyl and 6-indazolyl groups respectively, at the C13A position were the most potent inhibitors (percent growth inhibition at 1 μM of 78% and 91% for 16 and 17 respectively). The aminoindazole analog of compound 17, HSD1787 (see FIG. 4), inhibited MDA-MB-231 at 95% at 1 μM concentration and we proceeded to make analogs of HSD1787 for an in depth SAR studies. Specifically, next we made analogs to evaluate effect of substitution on various ring A, B, C, D, E and F of HSD1787 (see FIG. 4 for ring nomenclature and analogs that were made). In designing the analogs, we also decided to decorate HSD1787 with various substituents that are over represented in FDA-approved drugs. For example, many of the recently approved drugs contain halogens (mainly fluorine and to some limited extent chlorine). For example, encorafenib (a BRAf kinase inhibitor) is decorated with both F and Cl, see FIG. 3. Dacomitinib, a second-generation EGFR inhibitor for the treatment of non-small cell lung cancer also contains F and Cl substituents. A few drugs also contain bromine (such as the tuberculosis drug bedaquiline and arbidol, an antiviral drugs).

Figure 4:
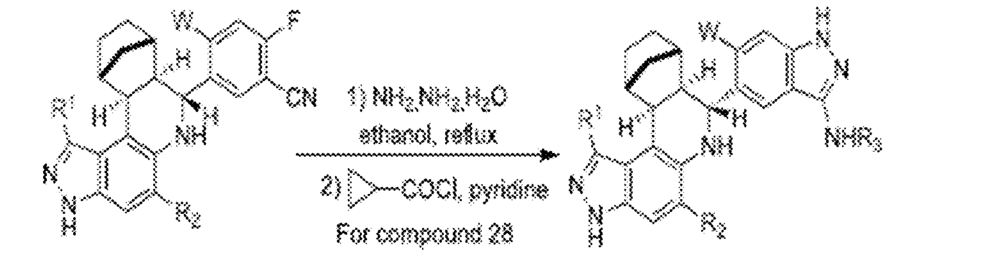
FIG. 4 shows compound 17 analogs that were synthesized and tested for growth inhibition of MDA-MB-231.
Figure 4:
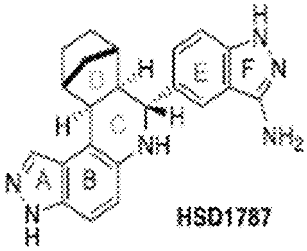
Figure 4:
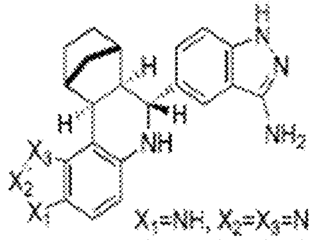
Figure 4:
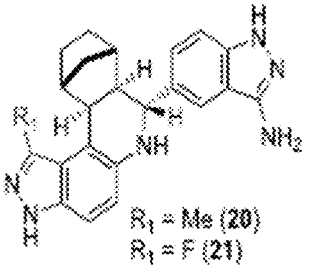
Figure 4:
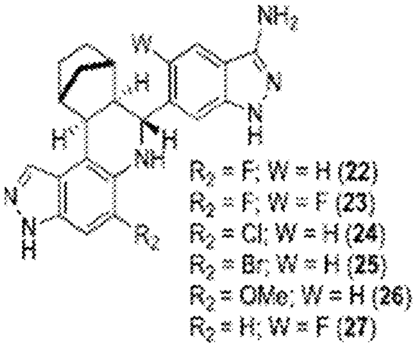
Figure 4:
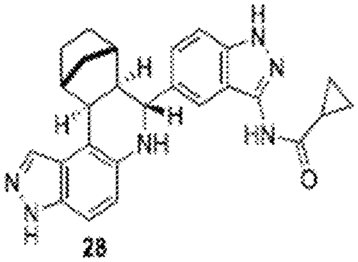
Figure 4:
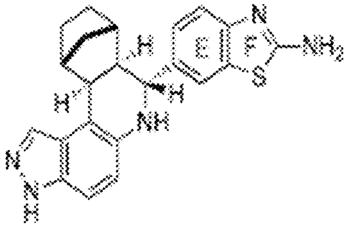
Figure 4:
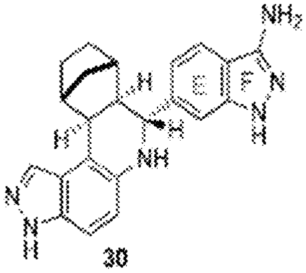
Figure 4:
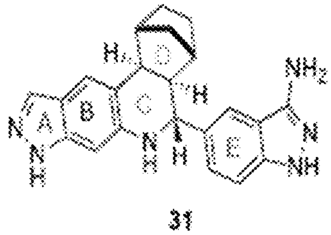

Regarding halogen substituents of drugs, there is now an increasing trend to include more than one fluorine substituent. This is due to the increased lipophilicity as well as metabolic stability that fluorine impacts to drugs. For example, drugs such as binimetinib, talazoparib, baloxavir, larotrectinib, entrectinib, lemborexant are examples of recently approved drugs that contain two fluorines on aromatic moieties in the drug.[32] At the extreme, some drugs contain three fluorines (such as bictegravir, lasmiditan and ivosidenib) and even six fluorine substituents, in this case two $CF_3$ groups (such as selinexor and fosnetupitant). The methoxy group is also over-represented in FDA-approved drugs [for example fostamatinib (SYK kinase inhibitor), naproxen (nonsteroidal anti-inflammatory drugs), oxypertine (an antipsychotic drug), pravadoline (an analgesic) amongst others]. Based on these drug precedents (whereby halogens are used to increase potency and/or metabolic stability), we synthesized halogen-containing analogs of HSD1787 to investigated the effects of halogen substitution on HSD1787 (see FIG. 4, compound 22, 23, 24, 25, 26 and 27). Compound 28 was synthesized to compare a free amine and amide on the indazole ring. Compound 29 contained another privileged moiety, benzothiazole, which is found in many bioactive compounds and drugs such as riluzole, lubeluzole and bentaluron.[33] Regioisomers of HSD1787, compounds 30 and 31, were also synthesized (FIG. 4).

Figure 5:
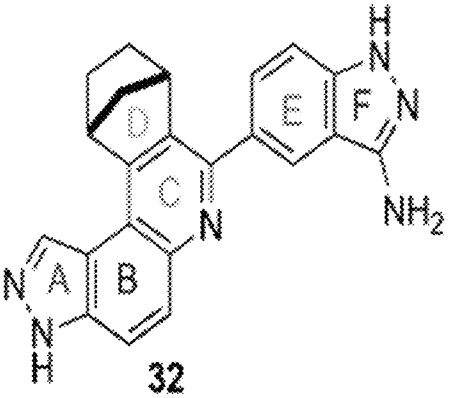
FIG. 5 depicts more the structures of the HSD1787 analogs, which were synthesized and tested for growth inhibition of MDA-MB-231.
Figure 5:
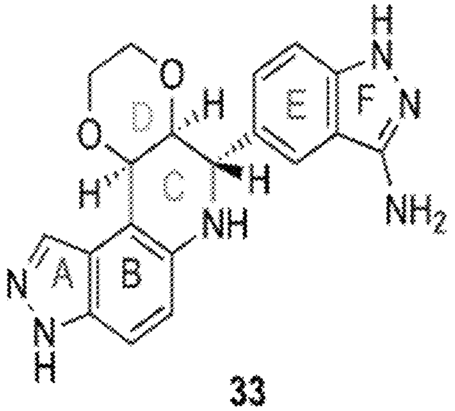

Drugs that contain high fraction $sp^3$ are generally considered as more drug-like than analogs that contain higher degree of polycyclic aromatic moieties.[36-40] Therefore we also designed a compound to investigate how the fraction $sp^3$ of the compound (compare HSD1787, FIG. 4, and compound 32, FIG. 5) affected anticancer activities. Also we designed compound 33, which did not contain the bicyclo [2.2.1]heptan-2-yl moiety in ring D but instead contained 2,3-dihydro-1,4-dioxine[41], to investigate if the bridged bicyclic, bicyclo[2.2.1]heptan-2-yl group found in HSD1787 and analogs is critical for anticancer activities.

Figure 6:
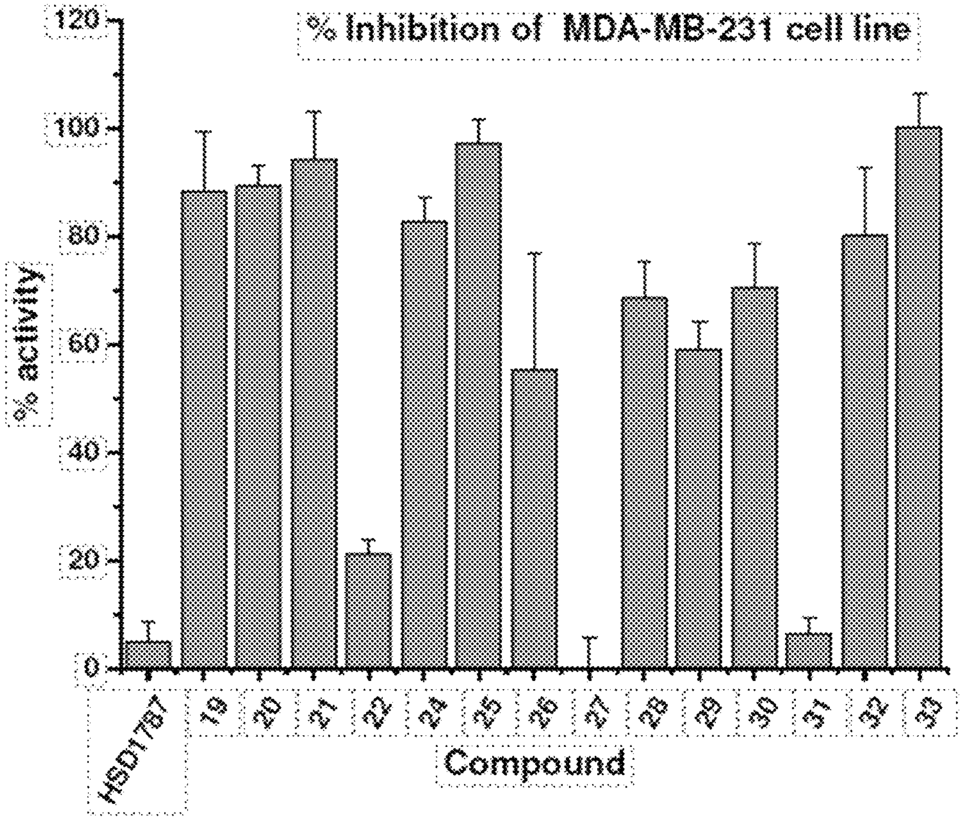
FIG. 6 demonstrates the inhibition of MDA-MB-231 by compounds. MDA-MB-231 cell line was treated with 1 μM of compounds and growth inhibition was assayed after 72 h incubation. Three biological replicates were done.
Figure 7A:
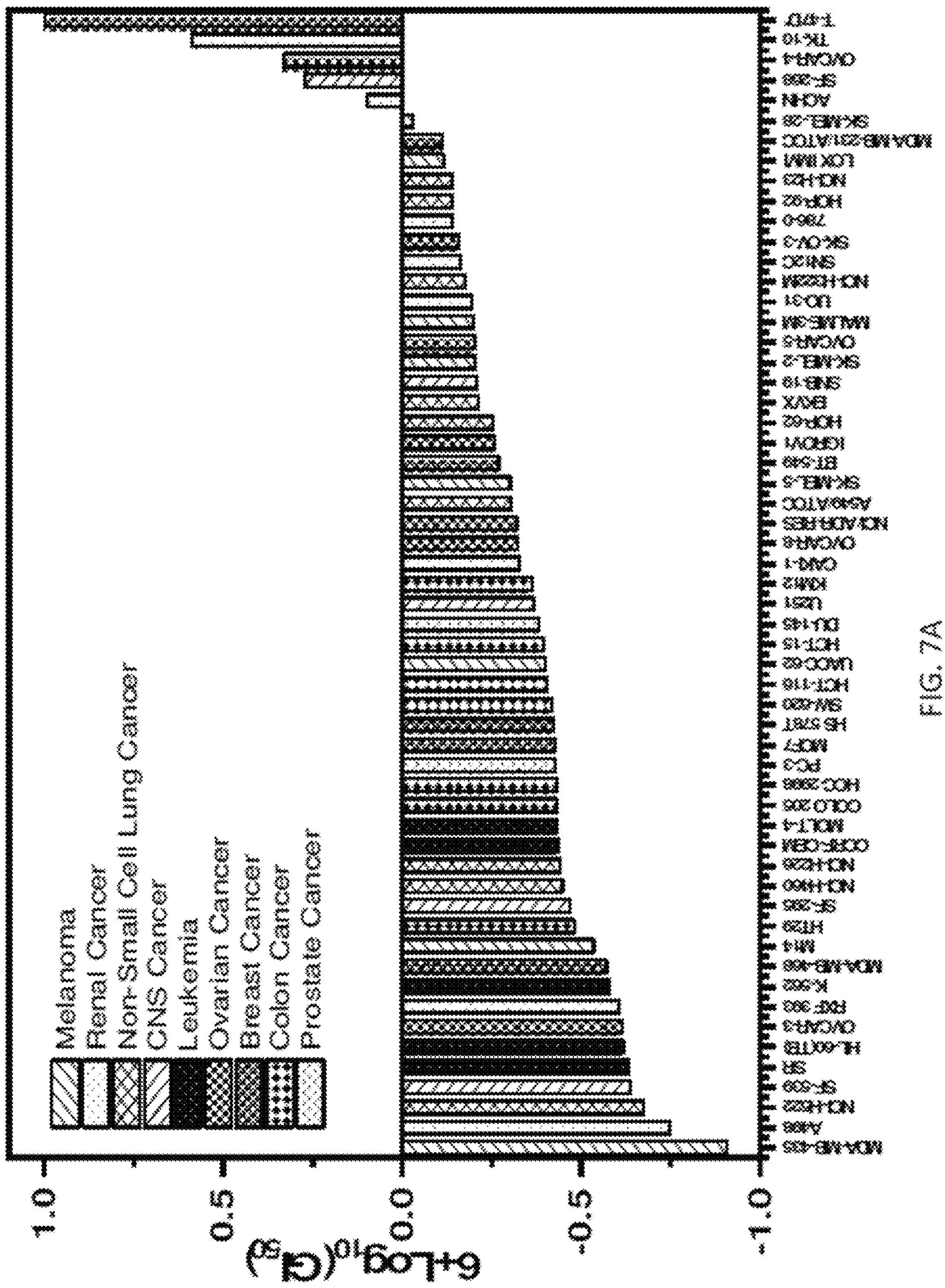
FIGS. 7A-7D show the assay results of in-vitro NCI60 cell lines vs GI50 representation for compounds.
Figure 7B:
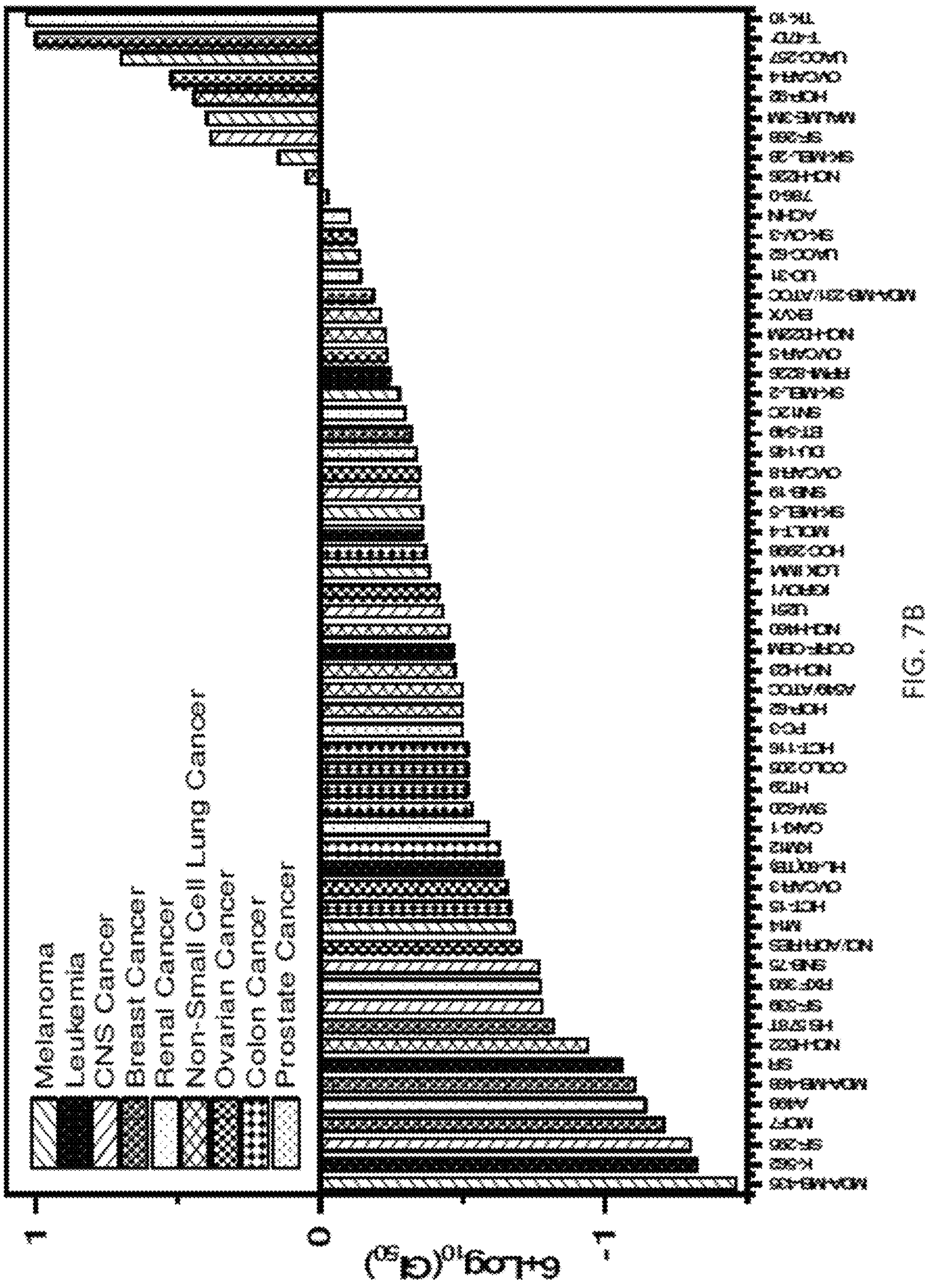
Figure 7C:
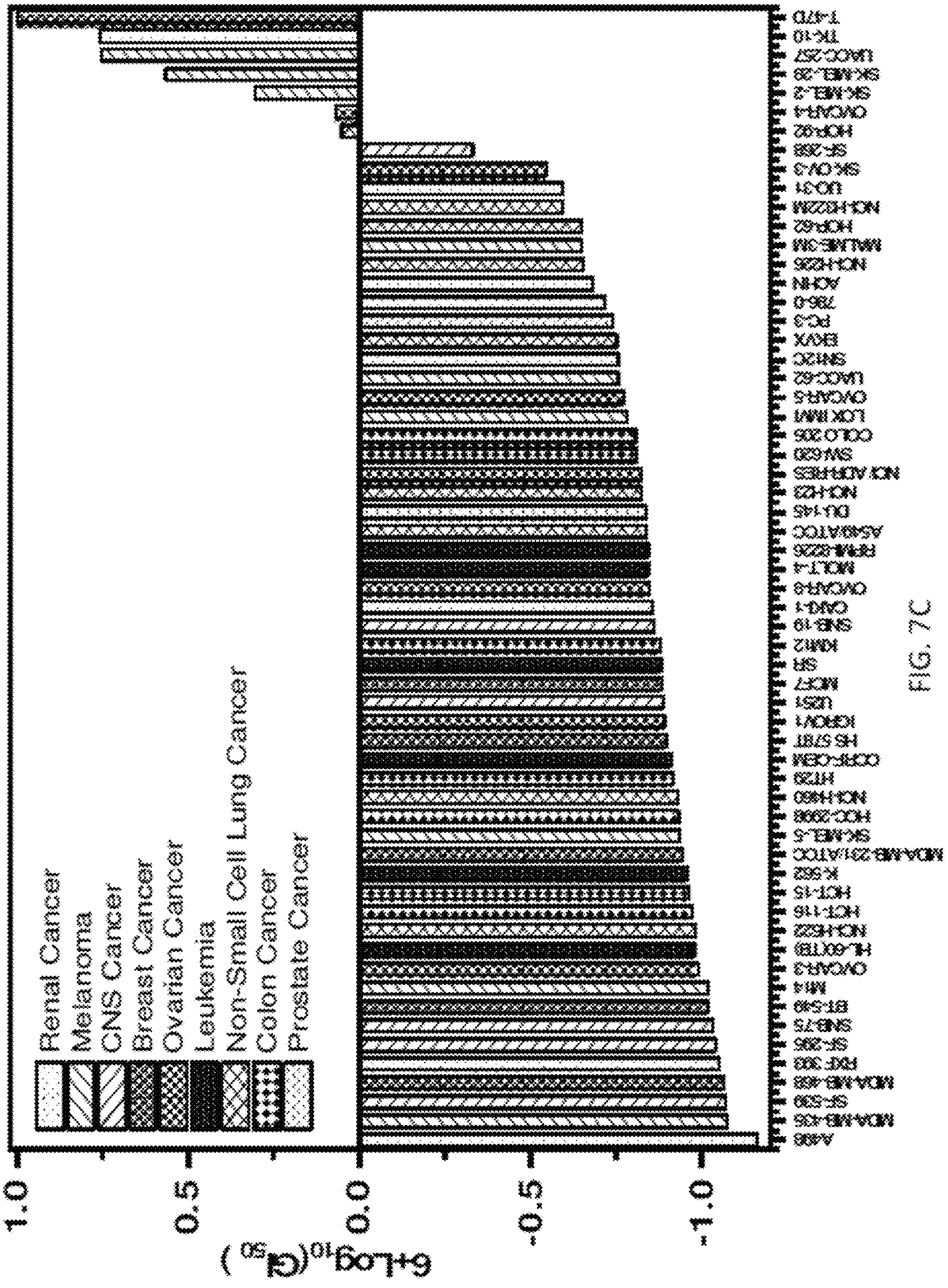
Figure 7D:
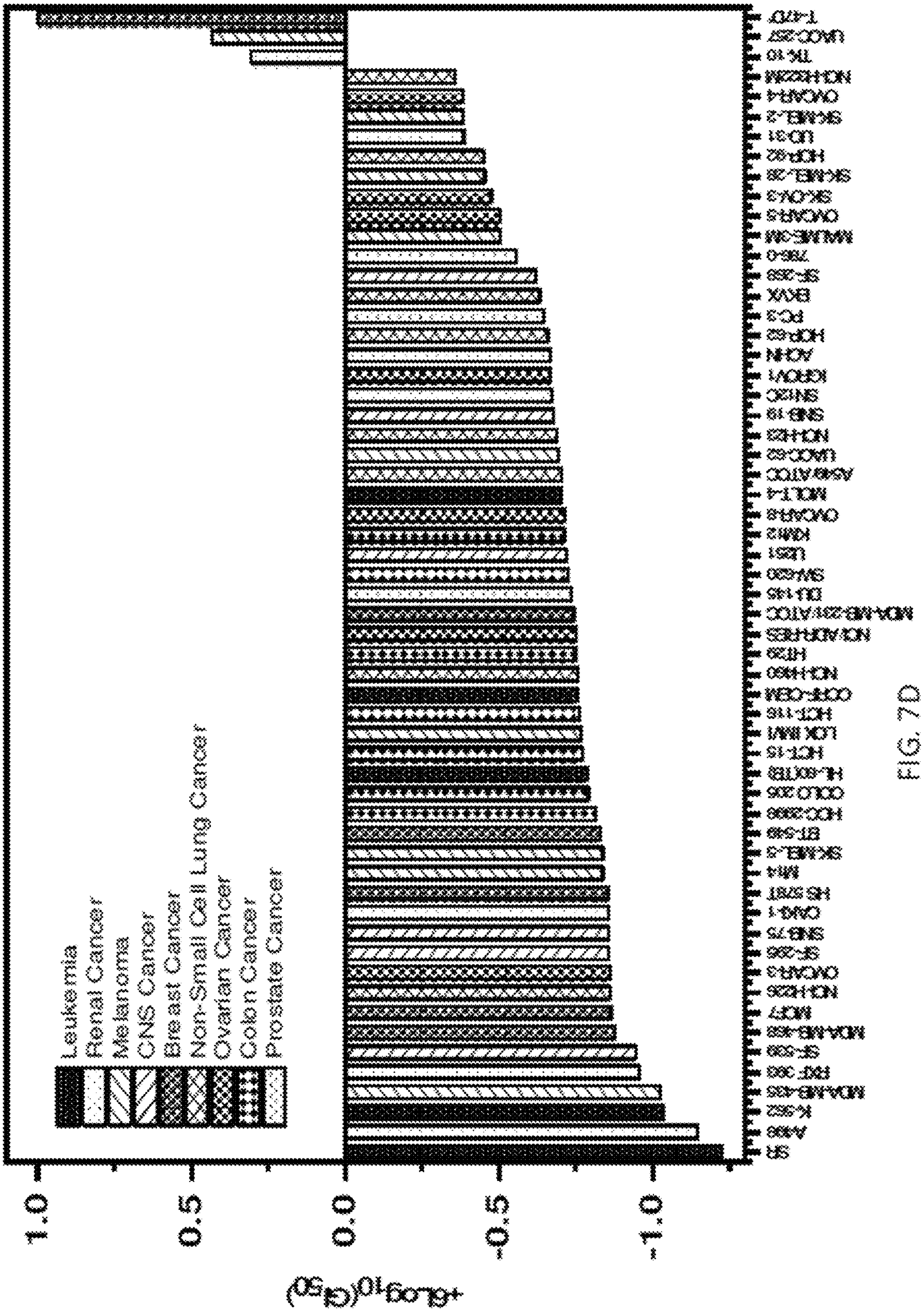

Screening for Inhibition of MDA-MB-231 Cell Line by HSD Analogs:

Next, we screened our synthesized library of seventeen HSD1787 analogs (FIGS. 4 and 5) against MDA-MB-231 and evaluated viability of the cancer cell line after 72 h incubation (FIG. 6). Compounds 18 and 19, whereby the tetrahydro-3H-pyrazolo[4,3-]quinoline moiety (referred to as TPQ herethereafter) in HSD1787 was changed to tetrahydro-3H-[1,2,3]triazolo[4,5-J]quinoline or tetrahydro-3H-imidazo[4,5-J]quinoline respectively, led to loss in potency. Likewise, —Me (20) and —F (21) substitution at 1-position of the TPQ core resulted in loss of potency. Substitution of position 5 of the TPQ unit with Cl (24), Br (25) led to inactive compounds whereas F (22) and OMe substitutions at position 5 of the TPQ unit of HSD1787 resulted in 79% and 55% growth inhibition of MDA-MB-231 respectively. Compound 27, which contained F substitution on the TPQ moiety as well as the indazoyl unit completely inhibited (~100%) the growth of MDA-MB-231 at 1 μM. Carboxamide analog (28) and aminobenzothiazole analog (29) inhibited MDA-MB-231 at 31% and 41% respectively. Notably, regioisomer of HSD1787 (compound 30) showed only 29% inhibition while another regioisomer of HSD1787 (compound 31), inhibited MDA-MB-231 at 94%, which is similar to HSD1787 (95% inhibition). Analog 32, with less $sp^3$ carbon than HSD1878 inhibited MDA-MB-231 at only 19%, highlighting that a higher fraction $sp^3$ is important for anticancer activities for this series. Compound 33, which did not contain the bicyclo[2.2.1]heptan-2-yl moiety in ring D but instead contained 2,3-dihydro-1,4-dioxine showed no activity.

TABLE 2

$GI_{50}$ and TGI (total growth inhibition) by HSD1787 (a), 22 (b), 23 (c) and 27 (d) against select cell lines.

| Entry | Cell line | Cancer type | $GI_{50}$/μM | TGI/μM |
|---|---|---|---|---|
| a | MDA-MB-435 | Melanoma | 0.124[a], 0.0348[b], 0.0846[c], 0.0943[d] | 0.329[a], ND[b], 0.231[c], 0.283[d] |
| b | K-562 | Leukemia | 0.264[a], 0.0477[b], 0.11[c], 0.0922[d] | >10[a], >10[b], >10[c], >10[d] |
| c | SF-539 | CNS | 0.232[a], 0.167[b], 0.0852[c], 0.114[d] | 0.654[a], 0.590[b], 0.270[c], 0.304[d] |
| d | MCF7 | Breast | 0.375[a], 0.0616[b], 0.131[c], 0.137[d] | >10[a], >10[b], 8.33[c], 8.44[d] |
| e | A498 | Renal | 0.179[a], 0.0722[b], 0.0690[c], 0.0714[d] | 0.646[a], 0.636[b], 0.2[c], 0.280[d] |
| f | MDA-MB-468 | Breast | 0.269[a], 0.0788[b], 0.0865[c], 0.133[d] | 2.73[a], 0.468[b], ND[c], 0.424[d] |
| g | SR | Lymphoma | 0.233[a], 0.0877[b], 0.131[c], 0.0598[d] | >10[a], >10[b], >10[c], >10[d] |
| h | SF-295 | CNS | 0.340[a], 0.05b, 0.0915[c], 0.139[d] | >10[a], >10[b], 3.99[c], 5.77[d] |

TABLE 2-continued $GI_{50}$ and TGI (total growth inhibition) by HSD1787 (a), 22 (b), 23 (c) and 27 (d) against select cell lines.

| Entry | Cell line | Cancer type | $GI_{50}$/μM | TGI/μM |
|---|---|---|---|---|
| i | Ovcar-3 | Ovarian | 0.243[a], 0.22[b], 0.103[c], 0.138[d] | 0.634[a], 0.806[b], 4.10[c], ND[d] |
| j | NCI-H522 | Non-Small Cell Lung | 0.21[a], 0.115[b], 0.105[c], 0.109[d] | 0.868[a], 1.92[b], 6.60[c], 0.544[d] |
| k | Ovcar-8 | Ovarian | 0.479[a], 0.448[b], 0.142[c], 0.194[d] | >10[a], >10[b], >10[c], >10[d] |
| l | NCI/ADR-RES | Ovarian | 0.480[a], 0.198[b], 0.150[c], 0.177[d] | >10[a], 0.921[b], 5.81[c], 1.21[d] |
| m | UACC-257 | Melanoma | >10[a], 5.01[b], 5.66[c], 2.70[d] | >10[a], >10[b], >10[c], >10[d] |
| n | TK-10 | Renal | 3.86[a], 10.7[b], 5.72[c], 2.02[d] | >10[a], >10[b], >10[c], >10[d] |
| o | Ovcar-4 | Ovarian | 2.14[a], 3.34[b], 1.17[c], 0.416[d] | >10[a], >10[b], >10[c], >10[d] |
| p | SK-MEL-28 | Melanoma | 0.934[a], 1.40[b], 3.68[c], 0.352[d] | >10[a], >10[b], >10[c], >10[d] |
| q | T-47D | Breast | >10[a],>10[b], >10[c], >10[d] | >10[a], >10[b], >10[c], >10[d] |

*[a]HSD1787; [b]Compound 22; [c]Compound 23; [d]Compound 27; ND = not determined; > 10 means value is greater than 10 uM. Values are average of a biological duplicate.

Compounds HSD1787, 22, 23 and 27 were sent to the National Cancer Institute (NCI), Bethesda, Maryland (Drug Evaluation Branch), to evaluate the effects of compounds on the NCI-60 cell panel. According to the NCI protocol, the compounds were evaluated at five concentrations (10-fold dilutions) with the highest concentration being 100 μM and the incubation period was 48 h. A sulforhodamine B assay was used to assay the effects of the compounds on the cancer cells. All four compounds exhibited sub-micromolar $GI_{50}$ (the concentration that causes 50% growth inhibition) against the majority of the cell lines in the NCI-60 panel (see FIGS. 7A-D). The most sensitive cell lines (total growth inhibition, TGI, could be achieved with concentrations less than 1 μM of some of the compounds) were MDA-MB-435 (melanoma), SF-539 (glioma), A498 (renal), MDA-MB-468 (breast), OVCAR-3 (ovarian), NCI-H522 (non-small cell lung cancer). On the other hand, UACC-257 and SK-MEL-28 (both melanoma), TK-10 (renal), OVCAR-4 (ovarian) and T-47D (breast) were resistant to the compounds as 10 μM could not cause total growth inhibition (Table 2). Thus, the inhibitions of the cancer cell lines by these new compounds do not necessarily depend on the tissue type but probably on specific cancer drivers. This is in line with current appreciation that tumor mutational burden and not necessarily the anatomical origin of the tumor determines treatment strategies or outcomes. Compounds that do not grossly kill all cell types but are selective for dysregulated pathways tend to be better tolerated by patients. NCI COMPARE analysis indicated that the cancer growth inhibition profiles of HSD1787 and analogs were similar to those of compounds that inhibit tubulin polymerization. This was verified experimentally whereby at 10 μM, HSD1787 and analogs inhibited the polymerization of tubulin (similar to inhibition by colchicine).

Conclusion: We have synthesized a library of compounds containing the tetrahydro-3H-pyrazolo[4,3-f]quinoline core, using the Povarov multicomponent reaction. These compounds, synthesized in only a single-flask operation, potently inhibited NCI-60 cancer cell lines at sub-micromolar concentrations. Fluorine substitution enhanced the anticancer properties and some of the compounds inhibited melanoma, breast, leukemia, lung and renal cell lines with $GI_{50}$ as low as 0.03 μM. The tetrahydro-3H-pyrazolo[4,3-f]quinoline-containing compounds represents one of the most potent anticancer agents synthesized via Povarov reported to date. The synthesized compounds inhibit tubulin polymerization and have the potential to be used in various diseased states whereby inhibition of tubulin polymerization (and vascular disruption) is beneficial, such as cancer. Tubulin polymerization inhibitors also have potential applications in areas beyond cancer, such as in controlling infection by various types of pathogens. This work adds literature examples whereby multicomponent reactions have been used to make libraries that contain potent anticancer agents with nanomolar activities.[42-46]

Experimental Section

MDA-MB-231 cell line was a kind gift from Professor Camarillo's lab (Purdue University). The cells were cultured using Dulbecco's Modified Eagle's Medium (DMEM) (Corning), supplemented with 10% fetal bovine serum (FBS) (Atlanta Biologicals), 1× glutaMAX (Gibco), and 1× penicillin/streptomycin (Corning) at 37° C. with 5% $CO_2$. Cells were seeded at $1.0\times10^4$ cells/mL in 96-well plates and incubated for up to 24 h. Cells were then treated with 1 μM of different compounds for 72 h in triplicates. The CellTiter-Blue Cell Viability Assay (Promega) was then added to the cells and incubated for 3 h before reading following the manufacturers recommendations.

GI50 Determination

According to the National Cancer Institute, Bethesda, Maryland (the protocol of the Drug Evaluation Branch), the effects of compounds are measured as follows: Cell suspensions are diluted to a target cell density of 5000-40,000 cells per well (based on cell growth characteristics) in a 96-well microtiter plates. The test compounds were evaluated at five concentrations (10-fold dilutions) with the highest concentration being 100 μM. The incubation period was 48 h under 5% carbon dioxide atmosphere and 100% humidity. A sulforhodamine B assay was used to assay the cells. Optical densities of the wells were read by a plate reader the optical densities were processed into GI50 (the concentration that causes 50% growth inhibition).

The NCI renamed the IC50 value, the concentration of compound that causes 50% growth inhibition, as follows:

GI50=100×(T−T0)/(C−T0)=50, where T=the optical density of the test well after a 48-h period of exposure to test drug, T0=the optical density at time zero, C=the control optical density. The control is the well not treated with test agent (https://dtp.cancer.gov/databases_tools/docs/compare/compare_methodology.htm).

General Procedure for the Multicomponent Reaction:

Method A: Amine (1 mmol) and aldehyde (1 mmol) in 4 mL of 1,1,1,3,3,3-Hexafluoro-2-propanol stirred for 2 h at 80° C. After that, alkene (2 mmol) and 10 mol % scandium (III) trifluoromethanesulfonate was added to the reaction mixture at ambient temperature. The reaction mixture was continued to stir for another 8 to 12 h. After completion, the reaction mixture was concentrated and purified by silica gel chromatography (Hexanes/ethyl acetate 95:5 to 50:50) or dichloromethane/methanol (99:01 to 95:05) to give the desired cyclized compound.

Method B: Formation of 1H-indazol-3-amine

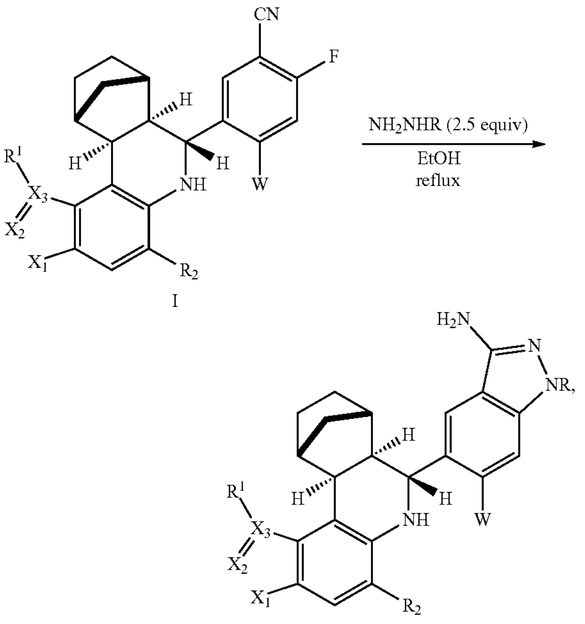

I

II wherein $R^1$ is methyl or F; $R^2$ is F, Cl, Br, or OMe; W is F; R is Me, ethyl, —$CH_2CH_2OH$; and $X_1$, $X_2$, or $X_3$ is N, NH, CO, S, or CH.

For the formation of 1H-indazol-3-amine ring, substrates I (0.3 mmol) prepared by method A was treated with hydrazine monohydrate (2.5 equiv) in ethanol (2 mL) at reflux for 4 to 8 h. After completion reaction was concentrated and purified by silica gel chromatography (dichloromethane/methanol (99:01 to 95:05) to give the desired compound.

7-(3-(Trifluoromethyl)-1H-pyrazol-4-yl)-6,7,7a,8,9,10,11,11a-octahydro 3H-8,11-methanopyrazolo[4,3-a]phenanthridine (1)

1

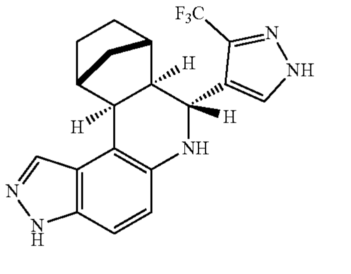

Method A Off-white solid (168 mg, 45%). $^1H$ NMR (500 MHz, DMSO-$d_6$) δ 7.85 (s, 1H), 7.63 (s, 1H), 7.11 (d, J=8.7 Hz, 1H), 6.79 (dd, J=8.7, 1.8 Hz, 1H), 5.21 (s, 1H), 4.08-3.96 (m, 1H), 2.90 (d, J=8.5 Hz, 1H), 2.68 (d, J=3.9 Hz, 1H), 2.11 (t, J=7.8 Hz, 1H), 2.04-1.98 (m, 1H), 1.66-1.58 (m, 2H), 1.58-1.48 (m, 2H), 1.29-1.20 (m, 1H), 1.03-0.94 (m, 1H); $^{13}C$ NMR (126 MHz, DMSO-$d_6$) δ 139.7, 138.3, 136.0, 131.4, 129.6, 124.1, 123.2, 121.8 (q=269.64 Hz), 118.5, 114.6, 108.5, 51.7, 49.9, 43.1, 42.4, 40.9, 34.2, 29.8, 29.4. HRMS (ESI) m/z calcd for $C_{19}H_{19}F_3N_5$ $[M+H]^+$ 374.1593, found 374.1586.

7-(1H-Pyrazol-4-yl)-6,7,7a,8,9,10,11,11a-octahydro-3H-8,11-methanopyrazolo[4,3-a]phenanthridine (2)

2

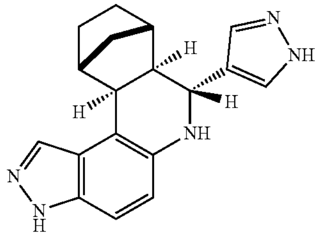

Method A Pale yellow solid (158 mg, 52%). $^1H$ NMR (500 MHz, DMSO-$d_6$) δ 7.83 (s, 1H), 7.49 (s, 2H), 7.08 (d, J=8.6 Hz, 1H), 6.78 (d, J=8.7 Hz, 1H), 6.04 (t, J=6.6 Hz, 1H), 5.24 (s, 1H), 3.93 (d, J=7.1 Hz, 1H), 3.92-3.80 (m, 2H), 2.87 (d, J=8.6 Hz, 1H), 2.66 (d, J=4.0 Hz, 1H), 2.17-2.05 (m, 2H), 1.66-1.58 (m, 2H), 1.58-1.42 (m, 2H), 1.34-1.23 (m, 1H), 0.96 (d, J=9.7 Hz, 1H); $^{13}C$ NMR (126 MHz, DMSO-$d_6$) δ 140.0, 137.9, 135.8, 131.3, 126.5, 125.2, 123.3, 118.7, 114.8, 108.2, 51.2, 51.0, 43.2, 42.5, 41.0, 34.4, 29.8, 29.6; HRMS (ESI) m/z calcd for $C_{18}H_{20}N_5$ $[M+H]^+$ 306.1719, found 306.1714.

2-(6,7,7a,8,9,10,11,11a-Octahydro-3H-8,11-methanopyrazolo[4,3-a]phenanthridin-7-yl)thiazole (3)

3

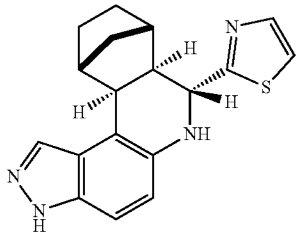

Method A Pale yellow solid (111 mg, 36%). $^1H$ NMR (500 MHz, Methanol-$d_4$) δ 7.88 (s, 1H), 7.63 (dd, J=3.4, 1.2 Hz, 1H), 7.34 (dd, J=3.3, 1.2 Hz, 1H), 7.20 (d, J=8.7 Hz, 1H), 6.83 (dd, J=8.8, 1.2 Hz, 1H), 4.60 (d, J=4.5 Hz, 1H), 3.06 (d, J=8.7 Hz, 1H), 2.61 (d, J=4.3 Hz, 1H), 2.43 (dd, J=8.7, 4.5 Hz, 1H), 2.36-2.29 (m, 1H), 1.83-1.75 (m, 1H), 1.75-1.68 (m, 1H), 1.65-1.53 (m, 2H), 1.45-1.35 (m, 1H), 1.14-1.04 (m, 1H); $^{13}C$ NMR (126 MHz, Methanol-$d_4$) δ 176.5, 140.5, 137.6, 136.2, 131.0, 122.6, 119.2, 119.1, 116.0, 108.3, 57.7, 50.1, 44.7, 42.1, 41.6, 34.0, 29.8, 28.5. HRMS (ESI) m/z calcd for $C_{18}H_{19}N_4S$ $[M+H]^+$ 323.1330, found 323.1323.

7-(1H-Imidazol-4-yl)-6,7,7a,8,9,10,11,11a-octahydro-3H-8,11-methanopyrazolo[4,3-a]phenanthridine (4)

4

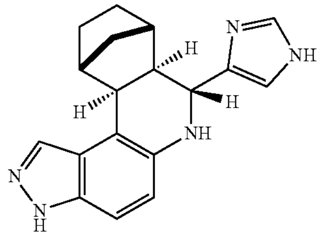

Method A Off-white solid (149 mg, 49%). $^{1}$H NMR (500 MHz, Methanol-$d_4$) δ 7.89 (s, 1H), 7.73 (s, 1H), 7.15 (d, J=8.7 Hz, 1H), 6.89 (s, 1H), 6.80 (d, J=8.7 Hz, 1H), 4.10 (d, J=7.1 Hz, 1H), 2.94 (d, J=8.6 Hz, 1H), 2.70 (d, J=4.1 Hz, 1H), 2.34 (t, J=7.8 Hz, 1H), 2.15 (d, J=3.8 Hz, 1H), 1.75-1.62 (m, 2H), 1.60-1.46 (m, 2H), 1.35-1.29 (m, 1H), 1.01 (d, J=9.9 Hz, 1H); $^{13}$C NMR (126 MHz, Methanol-$d_4$) δ 140.2, 138.7, 136.5, 134.3, 131.0, 122.7, 121.6, 119.1, 116.0, 108.2, 53.1, 48.8, 43.3, 42.2, 41.0, 33.7, 29.1. HRMS (ESI) m/z calcd for $C_{18}H_{20}N_5$[M+H]$^+$ 306.1719, found 306.1714.

7-(1-Methyl-3-(trifluoromethyl)-1H-pyrazol-4-yl)-6,7,7a,8,9,10,11,11a-octahydro-3H-8,11-methanopyrazolo[4,3-a]phenanthridine (5)

5

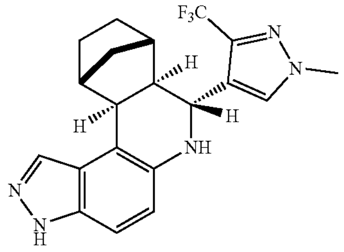

Method A Off-white solid (144 mg, 37%). $^{1}$H NMR (500 MHz, Methanol-$d_4$) δ 7.94 (s, 1H), 7.45 (s, 1H), 7.19 (d, J=8.7 Hz, 1H), 6.80 (d, J=8.7 Hz, 1H), 4.18 (d, J=6.7 Hz, 1H), 3.81 (s, 3H), 3.04 (d, J=8.6 Hz, 1H), 2.76 (d, J=4.2 Hz, 1H), 2.20 (t, J=7.6 Hz, 1H), 2.11 (d, J=3.8 Hz, 1H), 1.78-1.66 (m, 2H), 1.65-1.52 (m, 2H), 1.41-1.29 (m, 1H), 1.15-0.89 (m, 1H); $^{13}$C NMR (126 MHz, Methanol-$d_4$) δ 138.7, 138.4, 136.4, 131.2, 130.9, 125.1 (q=269.64 Hz), 124.6, 122.7, 118.9, 115.9, 108.1, 51.3, 50.0, 43.5, 42.3, 41.2, 38.1, 33.6, 29.2, 29.1. HRMS (ESI) m/z calcd for $C_{20}H_{21}F_3N_5$ [M+H]$^+$ 388.1749, found 388.1742.

7-(4-(Trifluoromethyl)phenyl)-6,7,7a,8,9,10,11,11a-octahydro-3H-8,11-methanopyrazolo[4,3-a]phenanthridine (6)

6

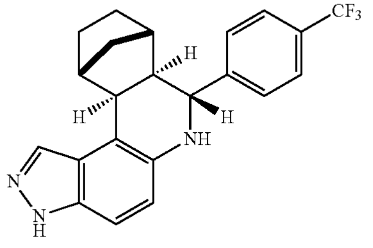

Method A Off-white solid (161 mg, 42%). $^{1}$H NMR (500 MHz, DMSO-$d_6$) δ 8.01 (s, 1H), 7.86 (s, 1H), 7.67 (d, J=8.2 Hz, 2H), 7.62 (d, J=8.2 Hz, 2H), 7.13 (d, J=8.7 Hz, 1H), 6.81 (d, J=8.7 Hz, 1H), 5.57 (s, 1H), 5.19-5.05 (m, 1H), 3.94 (d, J=8.2 Hz, 1H), 2.88 (d, J=8.5 Hz, 1H), 2.77 (d, J=3.9 Hz, 1H), 2.10 (t, J=8.4 Hz, 1H), 2.03 (d, J=4.1 Hz, 1H), 1.70 (d, J=9.8 Hz, 1H), 1.61 (dt, J=12.7, 4.6 Hz, 1H), 1.50 (dtd, J=12.0, 7.8, 3.8 Hz, 2H), 1.23-1.11 (m, 1H), 1.02 (d, J=9.8 Hz, 1H); $^{13}$C NMR (126 MHz, DMSO-$d_6$) δ 150.4, 139.7, 136.0, 131.5, 129.0, 128.2 (q, J=31.5 Hz), 125.9, 125.5, 125.4, 123.9 (q, J=286.06 Hz), 123.7, 123.2, 118.5, 114.2, 108.6, 67.7 (quintet, J=31.5 Hz), 59.7, 51.3, 42.7, 42.6, 34.2, 30.1, 29.0; HRMS (ESI) m/z calcd for $C_{22}H_{21}F_3N_3$ [M+H]$^+$ 384.1688, found 384.1681.

7-(3-Fluoropyridin-4-yl)-6,7,7a,8,9,10,11,11a-octahydro-3H-8,11-methanopyrazolo[4,3-a]phenanthridine (7)

7

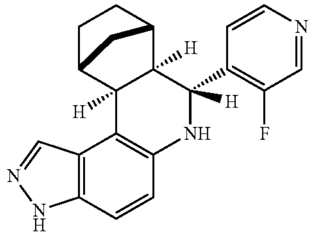

Method A Light brown solid (177 mg, 53%). $^{1}$H NMR (500 MHz, DMSO-$d_6$) δ 8.51 (s, 1H), 8.30 (d, J=5.0 Hz, 1H), 7.85 (s, 1H), 7.36 (t, J=5.7 Hz, 1H), 7.15 (d, J=8.7 Hz, 1H), 6.80 (d, J=8.7 Hz, 1H), 5.59 (s, 1H), 4.29 (d, J=6.8 Hz, 1H), 2.91 (d, J=8.5 Hz, 1H), 2.74-2.63 (m, 1H), 2.12 (t, J=7.8 Hz, 1H), 2.06 (d, J=3.4 Hz, 1H), 1.68-1.57 (m, 2H), 1.55-1.44 (m, 2H), 1.27-1.16 (m, 1H), 1.02 (d, J=9.8 Hz, 1H); $^{13}$C NMR (126 MHz, DMSO-$d_6$) δ 158.7 (J=254.52 Hz), 146.4, 141.1, 139.3, 138.1, 136.0, 131.4, 123.6, 123.2, 118.3, 114.2, 108.9, 51.7, 50.2, 43.3, 42.3, 41.1, 34.3, 29.7, 29.4. HRMS (ESI) m/z calcd for $C_{20}H_{20}FN_4$ [M+H]$^+$ 335.1672, found 335.1667.

7-(Thiophen-2-yl)-6,7,7a,8,9,10,11,11a-octahydro-3H-8,11-methanopyrazolo[4,3-a]phenanthridine (8)

8

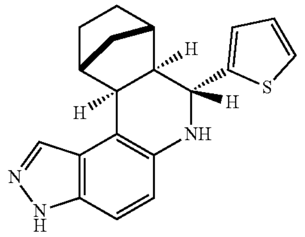

Method A Pale yellow solid (150 mg, 47%). $^1$H NMR (500 MHz, Methanol-$d_4$) δ 8.26 (d, J=1.1 Hz, 1H), 7.51 (dd, J=5.2, 1.2 Hz, 1H), 7.47 (dt, J=8.8, 1.1 Hz, 1H), 7.32 (dd, J=3.6, 1.3 Hz, 1H), 7.21 (d, J=8.8 Hz, 1H), 7.11 (dd, J=5.2, 3.5 Hz, 1H), 4.63 (d, J=10.3 Hz, 1H), 3.33-3.31 (m, 1H), 3.17-3.04 (m, 1H), 2.63 (ddd, J=10.0, 8.5, 1.2 Hz, 1H), 2.22-2.14 (m, 1H), 1.90-1.78 (m, 1H), 1.77-1.66 (m, 2H), 1.60 (dt, J=10.5, 1.9 Hz, 1H), 1.49-1.38 (m, 1H), 1.27-1.16 (m, 1H); $^{13}$C NMR (126 MHz, Methanol-$d_4$) δ 140.7, 139.5, 132.7, 128.3, 127.9, 126.8, 126.5, 124.4, 122.0, 120.0, 109.4, 57.3, 49.5, 43.1, 39.8, 33.2, 29.4, 28.2. HRMS (ESI) m/z calcd for $C_{19}H_{20}N_3S$ [M+H]$^+$ 322.1378, found 322.1371.

5-(6,7,7a,8,9,10,11,11a-Octahydro-3H-8,11-methanopyrazolo[4,3-a]phenanthridin-7-yl)pyridin-2-amine (9)

9

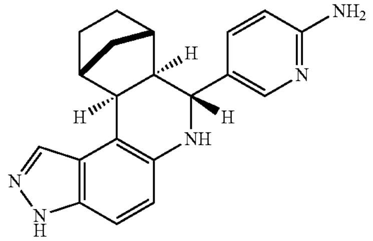

Method A Pale yellow solid (53 mg, 16%). $^1$H NMR (500 MHz, Methanol-$d_4$) δ 7.95 (d, J=1.1 Hz, 1H), 7.89 (d, J=2.4 Hz, 1H), 7.58 (dd, J=8.6, 2.4 Hz, 1H), 7.18 (d, J=8.7 Hz, 1H), 6.84 (d, J=8.7 Hz, 1H), 6.60 (d, J=8.6 Hz, 1H), 3.72 (d, J=9.3 Hz, 1H), 2.94 (dd, J=21.9, 6.3 Hz, 2H), 2.17 (d, J=8.9 Hz, 1H), 2.04 (d, J=4.2 Hz, 1H), 1.78-1.70 (m, 2H), 1.65-1.56 (m, 2H), 1.28 (tdd, J=11.0, 5.6, 2.3 Hz, 1H), 1.11 (dt, J=9.9, 1.5 Hz, 1H); $^{13}$C NMR (126 MHz, Methanol-$d_4$) δ 158.6, 146.5, 145.3, 139.6, 137.7, 128.8, 122.7, 119.0, 115.5, 109.1, 108.1, 58.1, 51.0, 42.9, 42.2, 39.6, 33.2, 29.7, 28.3. HRMS (ESI) m/z calcd for $C_{20}H_{22}N_5$[M+H]$^+$ 332.1875, found 332.1870.

2-Fluoro-5-(−6,7,7a,8,9,10,11,11a-octahydro-3H-8,11-methanopyrazolo[4,3-a]phenanthridin-7-yl)benzonitrile (10)

10

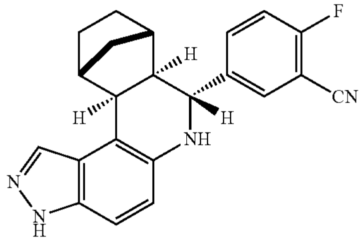

Method A Off-white solid (154 mg, 43%). $^1$H NMR (500 MHz, DMSO-$d_6$) δ 7.94 (dd, J=6.4, 2.3 Hz, 1H), 7.85 (d, J=1.3 Hz, 1H), 7.83-7.75 (m, 1H), 7.46 (t, J=9.0 Hz, 1H), 7.12 (d, J=8.6 Hz, 1H), 6.78 (d, J=8.7 Hz, 1H), 5.51 (s, 1H), 3.93 (dd, J=8.0, 1.4 Hz, 1H), 2.88 (d, J=8.5 Hz, 1H), 2.74 (d, J=3.9 Hz, 1H), 2.10 (t, J=8.3 Hz, 1H), 2.01 (d, J=4.0 Hz, 1H), 1.73-1.58 (m, 2H), 1.55-1.41 (m, 2H), 1.31-1.16 (m, 1H), 1.01 (d, J=9.8 Hz, 1H); $^{13}$C NMR (126 MHz, DMSO-$d_6$) δ 162.9 (J=255.78 Hz), 143.4, 139.6, 136.0, 135.7, 133.4, 131.5, 123.2, 118.4, 116.8, (18.19 Hz), 114.6, 114.3, 108.6, 100.1 (15.12), 58.5, 51.0, 42.7, 42.6, 34.3, 30.1, 29.0. HRMS (ESI) m/z calcd for $C_{22}H_{20}FN_4$ [M+H]$^+$ 359.1672, found 359.1665.

4-(−6,7,7a,8,9,10,11,11a-Octahydro-3H-8,11-methanopyrazolo[4,3-a]phenanthridin-7-yl)phenol (11)

11

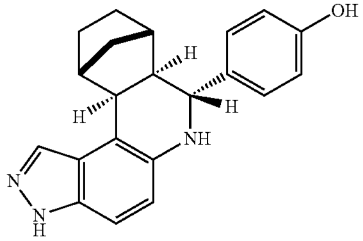

Method A Off-white solid (151 mg, 45%). $^1$H NMR (500 MHz, DMSO-$d_6$) δ 9.26 (s, 1H), 7.85 (s, 1H), 7.19 (d, J=8.5 Hz, 2H), 7.08 (d, J=8.7 Hz, 1H), 6.82 (d, J=8.7 Hz, 1H), 6.70 (d, J=8.5 Hz, 2H), 5.20 (s, 1H), 3.64 (d, J=9.0 Hz, 1H), 2.85-2.74 (m, 2H), 2.05-1.93 (m, 2H), 1.77-1.58 (m, 2H), 1.55-1.44 (m, 2H), 1.23-1.09 (m, 1H), 0.99 (d, J=9.7 Hz, 1H); $^{13}$C NMR (126 MHz, DMSO-$d_6$) δ 156.8, 140.6, 135.9, 131.5, 129.2, 123.3, 118.6, 115.3, 113.9, 108.3, 59.9, 52.0, 43.0, 42.0, 34.0, 30.4, 28.8. HRMS (ESI) m/z calcd for $C_{21}H_{22}N_{30}$ [M+H]$^+$ 332.1763, found 332.1755.

4-(6,7,7a,8,9,10,11,11a-Octahydro-3H-8,11-methanopyrazolo[4,3-a]phenanthridin-7-yl)benzamide (12)

12

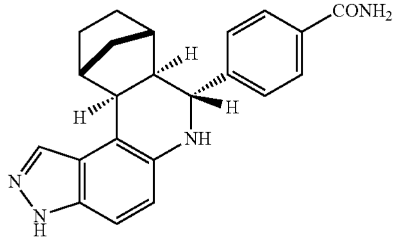

Method A Off-white solid (122 mg, 34%). $^1H$ NMR (500 MHz, DMSO-$d_6$) δ 7.89 (s, 1H), 7.85 (s, 1H), 7.80 (d, J=8.0 Hz, 2H), 7.46 (d, J=8.0 Hz, 2H), 7.28 (s, 1H), 7.10 (d, J=8.6 Hz, 1H), 6.81 (d, J=8.8 Hz, 1H), 5.44 (s, 1H), 3.87 (d, J=8.2 Hz, 1H), 2.86 (d, J=8.6 Hz, 1H), 2.77 (s, 1H), 2.11-2.08 (m, 1H), 2.03 (s, 1H), 1.70 (d, J=9.9 Hz, 1H), 1.64-1.59 (m, 1H), 1.54-1.46 (m, 2H), 1.21-1.15 (m, 1H), 1.04-1.00 (m, 1H); $^{13}C$ NMR (126 MHz, DMSO-$d_6$) δ 169.0, 149.8, 140.9, 136.7, 134.3, 132.3, 128.8, 128.6, 124.1, 119.3, 114.9, 109.3, 60.7, 52.3, 43.6, 43.3, 35.0, 31.0, 29.8. HRMS (ESI) m/z calcd for $C_{22}H_{23}N_4O$ [M+H]$^+$ 359.1872, found 359.1865.

7-(3-Cyclopropyl-1-methyl-1H-pyrazol-4-yl)-6,7,7a,8,9,10,11,11a-octahydro-3H-8,11-methanopyrazolo[4,3-a]phenanthridine (13)

13

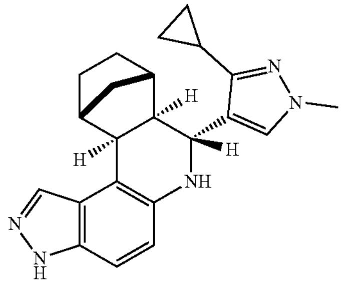

Method A Light brown solid (166 mg, 46%). $^1H$ NMR (500 MHz, DMSO-$d_6$) δ 7.86 (s, 1H), 7.35 (s, 1H), 7.09 (d, J=8.6 Hz, 1H), 6.81 (d, J=8.7 Hz, 1H), 5.09 (s, 1H), 3.90 (d, J=8.4 Hz, 1H), 3.63 (s, 2H), 2.85 (d, J=8.5 Hz, 1H), 2.77 (d, J=3.8 Hz, 1H), 2.11 (t, J=8.5 Hz, 1H), 2.07 (d, J=3.9 Hz, 1H), 1.90 (tt, J=8.2, 5.1 Hz, 1H), 1.69-1.64 (m, 1H), 1.61 (dt, J=10.7, 3.6 Hz, 1H), 1.52 (tdd, J=13.3, 8.0, 3.8 Hz, 2H), 1.21 (ddd, J=13.1, 9.8, 6.7 Hz, 1H), 1.02-0.96 (m, 1H), 0.83-0.69 (m, 4H). $^{13}C$ NMR (126 MHz, DMSO-$d_6$) δ 150.6, 140.5, 135.9, 131.5, 129.7, 123.4, 123.3, 118.6, 114.3, 108.3, 51.8, 51.0, 42.8, 42.4, 38.6, 34.1, 30.2, 29.2, 7.9, 7.8, 7.7. HRMS (ESI) m/z calcd for $C_{22}H_{26}N_5$[M+H]$^+$ 360.2188, found 360.2182.

3-Fluoro-4-(6,7,7a,8,9,10,11,11a-octahydro-3H-8,11-methanopyrazolo[4,3-a]phenanthridin-7-yl)phenol (14)

14

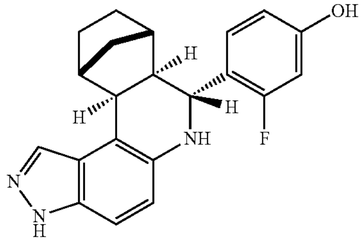

Method A Off-white solid (209 mg, 66%). $^1H$ NMR (500 MHz, DMSO-$d_6$) δ 9.76 (s, 1H), 7.85 (s, 1H), 7.24 (t, J=8.6 Hz, 1H), 7.10 (d, J=8.7 Hz, 1H), 6.81 (d, J=8.7 Hz, 1H), 6.57 (dd, J=8.5, 2.4 Hz, 1H), 6.52 (dd, J=12.2, 2.4 Hz, 1H), 5.24 (s, 1H), 4.02 (d, J=8.7 Hz, 1H), 2.84 (d, J=8.5 Hz, 1H), 2.78 (s, 1H), 2.06 (t, J=8.6 Hz, 1H), 1.97 (s, 1H), 1.71-1.57 (m, 2H), 1.51 (td, J=10.8, 4.0 Hz, 2H), 1.24-1.12 (m, 1H), 1.05-0.98 (m, 1H); $^{13}C$ NMR (126 MHz, DMSO-$d_6$) δ 161.9, 160.0 (J=253.26 Hz), 140.4, 135.9, 131.5, 129.8, 123.3, 122.2, 118.5, 112.1, 108.4, 102.5, 102.3, 52.1, 51.4, 42.9, 42.3, 34.1, 30.3, 28.9. HRMS (ESI) m/z calcd for $C_{21}H_{21}FN_{30}$ [M+H]$^+$ 350.1669, found 350.1663.

7-(3-Methoxypyridin-4-yl)-6,7,7a,8,9,10,11,11a-octahydro-3H-8,11-methanopyrazolo[4,3-a]phenanthridine (15)

15

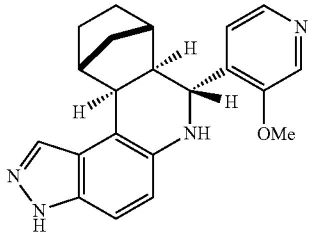

Method A Pale yellow solid (169 mg, 47%). $^1H$ NMR (500 MHz, DMSO-$d_6$) δ 8.56 (s, 1H), 8.33 (d, J=5.6 Hz, 1H), 7.90 (s, 1H), 7.59 (d, J=5.6 Hz, 1H), 7.21 (d, J=8.7 Hz, 1H), 6.88 (d, J=8.7 Hz, 1H), 4.52 (d, J=5.7 Hz, 1H), 4.03 (s, 3H), 2.96 (d, J=8.6 Hz, 1H), 2.63 (s, 1H), 2.22 (t, J=7.2 Hz, 1H), 2.11 (d, J=3.4 Hz, 1H), 1.65-1.56 (m, 2H), 1.52 (dt, J=8.8, 5.2 Hz, 2H), 1.30-1.21 (m, 1H), 1.01 (d, J=9.7 Hz, 1H); $^{13}C$ NMR (126 MHz, DMSO-$d_6$) δ 154.8, 137.3, 137.3, 137.2, 136.6, 131.4, 128.2, 124.0, 123.0, 123.0, 118.4, 109.3, 57.8, 52.2, 48.7, 44.3, 42.1, 41.8, 34.5, 29.8, 29.4. HRMS (ESI) m/z calcd for $C_{21}H_{23}N_4O$ [M+H]$^+$ 347.1872, found 347.1866.

7-(1H-Indazol-5-yl)-6,7,7a,8,9,10,11,11a-octahydro-3H-8,11-methanopyrazolo[4,3-a]phenanthridine (16)

16

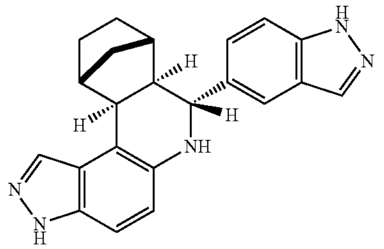

Method A Off-white solid (120 mg, 33%). $^1$H NMR (500 MHz, DMSO-$d_6$) δ 8.01 (t, J=1.3 Hz, 1H), 7.87 (s, 1H), 7.74 (s, 1H), 7.50 (d, J=8.7 Hz, 1H), 7.44 (dd, J=8.6, 1.6 Hz, 1H), 7.11 (d, J=8.7 Hz, 1H), 6.84 (d, J=8.8 Hz, 1H), 5.36 (s, 1H), 3.87 (d, J=8.9 Hz, 1H), 2.86 (d, J=8.6 Hz, 1H), 2.83 (s, 1H), 2.13 (t, J=8.8 Hz, 1H), 2.02 (s, 1H), 1.73 (d, J=9.8 Hz, 1H), 1.65-1.55 (m, 1H), 1.55-1.42 (m, 2H), 1.19-1.09 (m, 1H), 1.02 (d, J=9.8 Hz, 1H); $^{13}$C NMR (126 MHz, DMSO-$d_6$) δ 140.5, 139.8, 137.5, 135.9, 133.8, 131.5, 126.8, 123.4, 123.1, 119.6, 118.6, 113.9, 110.3, 108.4, 60.6, 52.0, 43.0, 42.1, 34.1, 30.4, 28.8. HRMS (ESI) m/z calcd for $C_{22}H_{22}N_5$ $[M+H]^+$ 356.1875, found 356.1869.

7-(1H-Indazol-6-yl)-6,7,7a,8,9,10,11,11a-octahydro-3H-8,11-methanopyrazolo[4,3-a]phenanthridine (17)

17

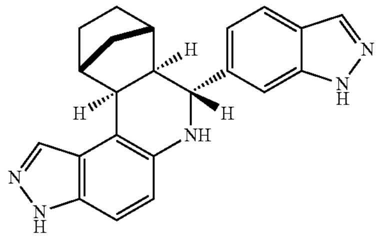

Method A Off-white solid (133 mg, 37%). $^1$H NMR (500 MHz, DMSO-$d_6$) δ 8.00 (s, 1H), 7.86 (s, 1H), 7.69 (d, J=8.3 Hz, 1H), 7.49 (s, 1H), 7.19 (dd, J=8.4, 1.4 Hz, 1H), 7.11 (d, J=8.7 Hz, 1H), 6.83 (d, J=8.7 Hz, 1H), 5.44 (s, 1H), 3.94 (d, J=8.3 Hz, 1H), 2.88 (d, J=8.6 Hz, 1H), 2.83-2.74 (m, 1H), 2.15 (t, J=8.5 Hz, 1H), 2.07 (d, J=4.1 Hz, 1H), 1.74 (d, J=9.8 Hz, 1H), 1.67-1.56 (m, 1H), 1.57-1.39 (m, 2H), 1.25-1.10 (m, 1H), 1.03 (d, J=9.7 Hz, 1H); $^{13}$C NMR (126 MHz, DMSO-$d_6$) δ 143.9, 140.4, 140.3, 135.9, 133.6, 131.5, 123.3, 122.5, 121.3, 120.5, 118.5, 114.0, 109.0, 108.4, 60.5, 51.8, 42.9, 42.5, 34.2, 30.2, 29.0. HRMS (ESI) m/z calcd for $C_{22}H_{22}N_5[M+H]^+$ 356.1875, found 356.1870.

5-(6,7,7a,8,9,10,11,11a-Octahydro-3H-8,11-methanopyrazolo[4,3-a]phenanthridin-7-yl)-1H-indazol-3-amine (HSD1787)

HSD1787

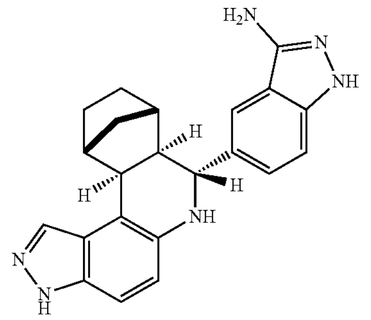

Prepared by using compound 10 as substrate. Method B Off-white solid (94 mg, 85%). $^1$H NMR (500 MHz, DMSO-$d_6$) δ 11.29 (s, 1H), 7.88 (s, 1H), 7.75 (d, J=1.6 Hz, 1H), 7.32 (dd, J=8.6, 1.6 Hz, 1H), 7.19 (d, J=8.5 Hz, 1H), 7.10 (d, J=8.7 Hz, 1H), 6.85 (d, J=8.7 Hz, 1H), 5.29 (s, 3H), 3.74 (d, J=9.6 Hz, 1H), 2.86 (dd, J=15.4, 6.2 Hz, 2H), 2.11 (t, J=9.1 Hz, 1H), 2.03 (d, J=4.2 Hz, 1H), 1.71 (d, J=9.8 Hz, 1H), 1.64 (tt, J=12.3, 4.4 Hz, 1H), 1.56-1.44 (m, 2H), 1.18-1.09 (m, 1H), 1.04 (d, J=9.7 Hz, 1H); $^{13}$C NMR (126 MHz, DMSO-$d_6$) δ 149.6, 141.6, 140.8, 135.9, 134.5, 131.6, 126.9, 123.4, 119.7, 118.6, 114.3, 113.7, 109.5, 108.3, 61.0, 52.3, 43.2, 41.7, 39.3, 34.0, 30.6, 28.6; HRMS (ESI) m/z calcd for $C_{22}H_{23}N_6[M+H]^+$ 371.1984, found 371.1977.

2-Fluoro-5-(6,7,7a,8,9,10,11,11a-octahydro-3H-8,11-methano[1,2,3]triazolo[4,5-a]phenanthridin-7-yl) benzonitrile (S-1)

S-1

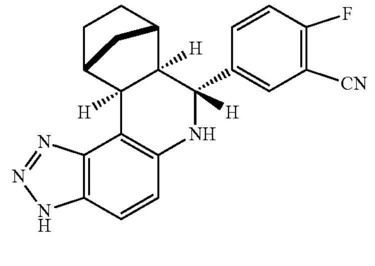

Method A Off-white solid (183 mg, 51%). $^1$H NMR (500 MHz, DMSO-$d_6$) δ 7.97-7.89 (m, 1H), 7.79-7.70 (m, 1H), 7.54 (d, J=8.9 Hz, 1H), 7.46 (d, J=9.1 Hz, 1H), 6.77 (d, J=8.8 Hz, 1H), 6.19 (s, 1H), 4.08 (d, J=6.7 Hz, 1H), 2.85 (d, J=8.6 Hz, 1H), 2.58 (s, 1H), 2.20-2.13 (m, 1H), 2.11-2.06 (m, 1H), 1.69-1.58 (m, 2H), 1.57-1.42 (m, 2H), 1.25 (s, 1H), 1.01 (d, J=10.1 Hz, 1H); $^{13}$C NMR (126 MHz, DMSO) δ 162.8 (J=254.5 Hz), 145.1, 143.1, 139.7, 135.4, 133.8, 133.3, 116.9, 116.8, 116.0, 114.5, 105.2, 100.2, 100.1, 57.5, 49.9, 42.3, 41.1, 40.7, 34.3, 29.9, 29.2.

5-(6,7,7a,8,9,10,11,11a-Octahydro-3H-8,11-methano[1,2,3]triazolo[4,5-a]phenanthridin-7-yl)-1H-indazol-3-amine (18)

18

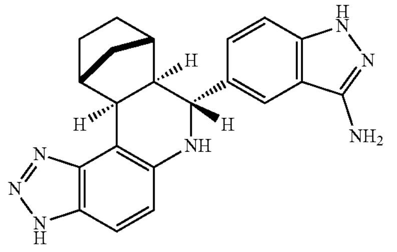

Prepared by using S-1 as substrate. Method B Off-white solid (91 mg, 82%). H NMR (500 MHz, DMSO-$d_6$) δ 7.75 (s, 1H), 7.48 (d, J=8.7 Hz, 1H), 7.30 (dd, J=8.7, 1.6 Hz, 1H), 7.20 (d, J=8.5 Hz, 1H), 6.87 (d, J=8.8 Hz, 1H), 5.90 (s, 1H), 5.31 (s, 2H), 3.80 (d, J=9.1 Hz, 1H), 2.95 (s, 1H), 2.86 (d, J=8.6 Hz, 1H), 2.14 (t, J=8.8 Hz, 1H), 2.07 (d, J=4.2 Hz, 1H), 1.70-1.60 (m, 2H), 1.56-1.44 (m, 2H), 1.18-1.09 (m, 1H), 1.04 (d, J=9.9 Hz, 1H); $^{13}$C NMR (126 MHz, DMSO) δ 149.6, 145.7, 141.6, 137.4, 136.9, 134.2, 126.8, 119.7, 117.2, 115.0, 114.3, 109.7, 106.3, 60.3, 51.8, 41.6, 41.0, 33.9, 30.6, 28.6.

2-Fluoro-5-(6,7,7a,8,9,10,11,11a-octahydro-3H-8,11-methanoimidazo[4,5-a]phenanthridin-7-yl)benzonitrile (S-2)

S-2

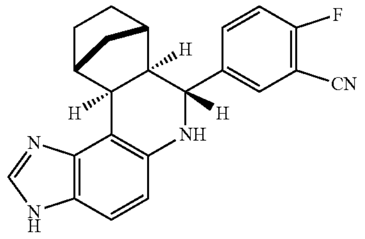

Method A Off white solid (130 mg, 36%). $^1$H NMR (500 MHz, DMSO-$d_6$) δ 7.93 (s, 1H), 7.90 (dd, J=6.4, 2.4 Hz, 1H), 7.76 (ddd, J=8.2, 5.4, 2.3 Hz, 1H), 7.43 (t, J=9.0 Hz, 1H), 7.14 (d, J=8.4 Hz, 1H), 6.58 (d, J=8.4 Hz, 1H), 5.54 (s, 1H), 3.98 (d, J=6.9 Hz, 1H), 2.99-2.83 (m, 2H), 2.12 (t, J=7.8 Hz, 1H), 2.06-2.02 (m, 1H), 1.69-1.54 (m, 2H), 1.52-1.42 (m, 2H), 1.29-1.15 (m, 1H), 1.02-0.83 (m, 1H); $^{13}$C NMR (126 MHz, DMSO-$d_6$) δ 162.7, (d, J=255.7 Hz), 143.7, 141.6, 140.1, 135.6, 135.5, 133.3, 116.8, 116.6, 114.6, 112.3, 100.0, 99.9, 58.3, 50.5, 42.3, 41.2, 41.0, 34.3, 29.9, 29.4.

5-(6,7,7a,8,9,10,11,11a-Octahydro-3H-8,11-methanoimidazo[4,5-a]phenanthridin-7-yl)-1H-indazol-3-amine

19

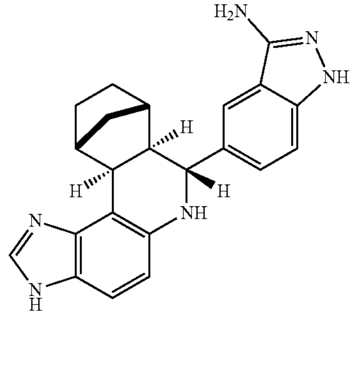

Prepared by using S-2 as substrate. Method B off-white solid (79 mg, 71%). $^1$H NMR (500 MHz, Methanol-$d_4$) δ 7.97 (s, 1H), 7.70 (s, 1H), 7.43 (dd, J=8.7, 1.7 Hz, 1H), 7.29-7.22 (m, 2H), 6.68 (d, J=8.5 Hz, 1H), 3.91 (d, J=9.2 Hz, 1H), 3.03-2.96 (m, 2H), 2.30 (t, J=8.9 Hz, 1H), 2.11 (d, J=4.2 Hz, 1H), 1.79-1.69 (m, 2H), 1.65-1.51 (m, 2H), 1.29-1.19 (m, 1H), 1.10 (d, J=10.0 Hz, 1H); $^{13}$C NMR (126 MHz, Methanol-$d_4$) δ 149.0, 142.5, 141.7, 139.2, 135.0, 133.4, 127.3, 118.7, 114.0, 113.7, 112.9, 111.4, 109.4, 61.2, 51.5, 41.5, 41.2, 39.9, 33.3, 29.9, 28.3.

2-Fluoro-5-(1-methyl-6,7,7a,8,9,10,11,11a-octahydro-3H-8,11-methanopyrazolo[4,3-a]phenanthridin-7-yl)benzonitrile (S-3)

S-3

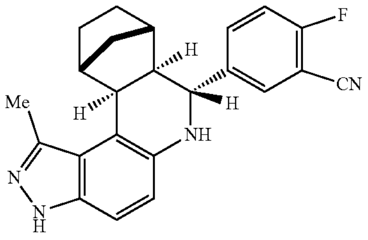

Method A Pale yellow solid (160 mg, 43%). $^1$H NMR (500 MHz, DMSO-$d_6$) δ 12.21 (s, 1H), 7.79 (dd, J=6.3, 2.4 Hz, 1H), 7.63 (ddd, J=8.2, 5.4, 2.4 Hz, 1H), 7.33 (t, J=9.1 Hz, 1H), 7.00 (d, J=8.6 Hz, 1H), 6.67 (d, J=8.7 Hz, 1H), 5.57 (s, 1H), 4.30 (s, 1H), 3.25 (d, J=8.7 Hz, 1H), 2.53 (s, 3H), 2.29-2.23 (m, 2H), 2.21 (d, J=3.1 Hz, 1H), 1.79 (d, J=9.5 Hz, 1H), 1.65-1.58 (m, 1H), 1.56-1.50 (m, 2H), 1.44-1.37 (m, 1H), 0.93 (d, J=9.5 Hz, 1H); $^{13}$C NMR (126 MHz, DMSO-$d_6$) δ 162.3 (d, J=253.26 Hz), 144.4, 139.2, 137.4, 134.9, 134.9, 132.9, 121.1, 118.5, 116.5, 116.4, 114.7, 109.0, 99.8 (d, J=15.12 Hz), 56.7, 48.7, 47.9, 43.8, 40.8, 34.6, 30.5, 28.7, 15.2. HRMS (ESI) m/z calcd for $C_{23}H_{22}FN_4$ $[M+H]^+$ 373.1828, found 373.1829.

5-(1-Methyl-6,7,7a,8,9,10,11,11a-octahydro-3H-8,11-methanopyrazolo[4,3-a]phenanthridin-7-yl)-1H-indazol-3-amine (20)

20

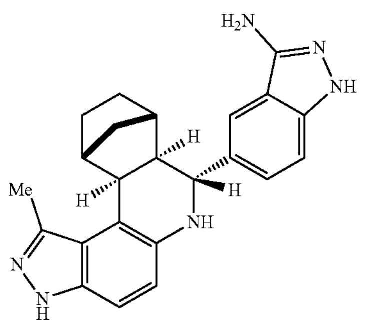

Prepared by using S-3 as substrate. Method B Pale yellow solid (95 mg, 82%). $^1H$ NMR (500 MHz, Methanol-$d_4$) δ 7.60 (s, 1H), 7.34 (dd, J=8.7, 1.6 Hz, 1H), 7.17 (dd, J=8.7, 0.8 Hz, 1H), 7.06 (d, J=8.7 Hz, 1H), 6.74 (d, J=8.7 Hz, 1H), 4.22 (d, J=5.3 Hz, 1H), 2.67 (s, 3H), 2.53-2.47 (m, 1H), 2.42-2.34 (m, 1H), 2.26-2.21 (m, 1H), 1.93 (dt, J=9.8, 1.9 Hz, 1H), 1.75-1.67 (m, 1H), 1.67-1.58 (m, 2H), 1.43-1.34 (m, 1H), 1.06 (dt, J=9.9, 1.4 Hz, 1H); $^{13}C$ NMR (126 MHz, Methanol-$d_4$) δ 148.8, 141.3, 140.0, 138.1, 137.8, 136.4, 127.1, 120.8, 119.3, 117.8, 116.97, 113.5, 109.2, 108.2, 59.6, 50.1, 42.8, 41.5, 33.4, 29.3, 29.2, 13.8. HRMS (ESI) m/z calcd for $C_{23}H_{25}N_6[M+H]^+$ 385.2141, found 385.2133.

Synthesis of 2-Fluoro-5-(1-fluoro-6,7,7a,8,9,10,11,11a-octahydro-3H-8,11-methanopyrazolo[4,3-a]phenanthridin-7-yl)benzonitrile (S-4)

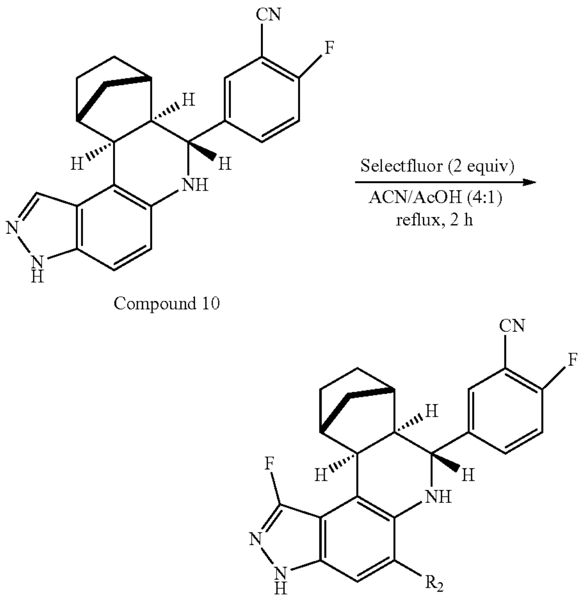

Compound 10

S-4

Selectfluor (149 mg, 2 equiv) was added to a mixture of compound 10 (150 mg, 0.42 mmol) in acetonitrile (4 mL) and acetic acid (1 mL). Reaction mixture was refluxed for 2 h. After completion of reaction extract with ethyl acetate and water and organic layer was dried and purified by silica gel column chromatography. Yellow solid (79 mg, 50%). $^1H$ NMR (500 MHz, DMSO-$d_6$) δ 12.09 (s, 1H), 7.89 (d, J=2.3 Hz, 1H), 7.74 (ddd, J=8.3, 5.4, 2.3 Hz, 1H), 7.43 (t, J=9.1 Hz, 1H), 7.04 (dd, J=8.9, 2.4 Hz, 1H), 6.83 (dd, J=8.9, 1.3 Hz, 1H), 5.70 (d, J=2.0 Hz, 1H), 4.11-4.02 (m, 1H), 2.92 (d, J=8.5 Hz, 1H), 2.45 (d, J=4.5 Hz, 1H), 2.13 (t, J=7.5 Hz, 1H), 2.10-2.05 (m, 1H), 1.69 (d, J=9.8 Hz, 1H), 1.60 (tt, J=11.2, 4.4 Hz, 1H), 1.55-1.41 (m, 2H), 1.30-1.23 (m, 1H), 0.98 (d, J=9.9 Hz, 1H); $^{13}C$ NMR (126 MHz, DMSO-$d_6$) δ 162.7, 160.7, 157.5, 155.6, 143.5, 139.3, 137.9, 137.7, 135.5, 135.4, 133.3, 120.5, 116.8, 116.6, 114.6, 113.3, 109.6, 107.2, 107.0, 100.1, 99.9, 57.4, 49.7, 45.0, 41.6, 41.2, 34.0, 30.0, 29.3; HRMS (ESI) m/z calcd for $C_{22}H_{19}F_2N_4$ $[M+H]^+$ 377.1578, found 377.1578.

5-(1-Fluoro-6,7,7a,8,9,10,11,11a-octahydro-3H-8,11-methanopyrazolo[4,3-a]phenanthridin-7-yl)-1H-indazol-3-amine (21)

21

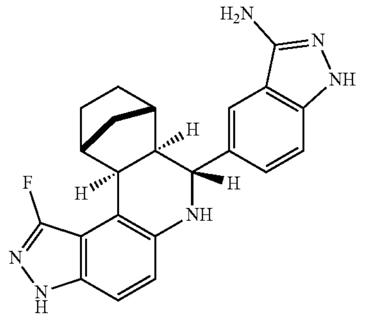

Prepared by using S-4 as substrate. Method B Off-white solid (91 mg, 78%). $^1H$ NMR (500 MHz, Methanol-$d_4$) δ 7.73-7.68 (m, 1H), 7.44 (dd, J=8.7, 1.6 Hz, 1H), 7.27 (dd, J=8.7, 0.8 Hz, 1H), 7.05 (ddd, J=8.9, 2.6, 1.0 Hz, 1H), 6.87 (d, J=8.8 Hz, 1H), 3.98 (d, J=8.8 Hz, 1H), 3.02 (d, J=8.5 Hz, 1H), 2.72 (s, 1H), 2.29 (t, J=8.7 Hz, 1H), 2.13 (d, J=4.2 Hz, 1H), 1.86-1.79 (m, 1H), 1.69 (dt, J=11.3, 4.0 Hz, 1H), 1.65-1.53 (m, 2H), 1.30-1.23 (m, 1H), 1.10 (dt, J=10.2, 1.5 Hz, 1H); $^{13}C$ NMR (126 MHz, Methanol-$d_4$) δ 157.8, 155.8, 149.0, 141.7, 139.7, 138.5, 135.0, 127.2, 120.6, 118.6, 114.4, 113.7, 113.7, 109.4, 108.5, 107.1, 60.4, 51.1, 44.0, 42.2, 40.2, 32.8, 30.3, 28.1. HRMS (ESI) m/z calcd for $C_{22}H_{22}FN_6$ $[M+H]^+$ 389.1890, found 389.1884.

2-Fluoro-5-(5-fluoro-6,7,7a,8,9,10,11,11a-octahydro-3H-8,11-methanopyrazolo[4,3-a]phenanthridin-7-yl)benzonitrile (S-5)

S-5

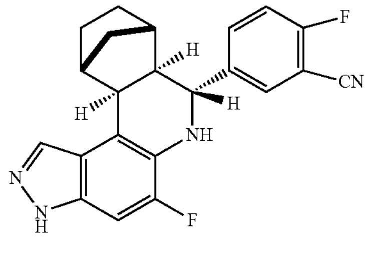

Method A Off white solid (113 mg, 30%). $^{1}$H NMR (500 MHz, DMSO-$d_6$) δ 7.94-7.86 (m, 1H), 7.78-7.67 (m, 1H), 7.43 (t, J=9.1 Hz, 1H), 7.08 (d, J=10.4 Hz, 1H), 5.33 (d, J=2.5 Hz, 1H), 4.10-3.98 (m, 1H), 2.99 (d, J=8.6 Hz, 1H), 2.66 (s, 1H), 2.19 (t, J=7.7 Hz, 1H), 2.07 (s, 1H), 1.68-1.59 (m, 1H), 1.59-1.48 (m, 1H), 1.32-1.22 (m, 1H), 1.01 (d, J=9.9 Hz, 1H); $^{13}$C NMR (126 MHz, DMSO-$d_6$) δ 162.8 (d, J=245.5 Hz), 153.4 (d, J=240.6 Hz), 143.1, 135.4, 133.6, 133.4, 131.7, 128.7, 119.3, 117.5, 116.7, 114.6, 100.0, 93.9, 57.5, 49.9, 43.7, 42.3, 40.9, 34.5, 29.7, 29.4.

5-(5-fluoro-6,7,7a,8,9,10,11,11a-octahydro-3H-8,11-methanopyrazolo[4,3-a]phenanthridin-7-yl)-1H-indazol-3-amine (22)

22

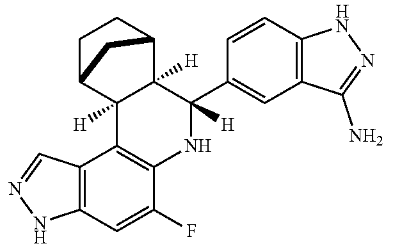

Prepared by using compound S-5 as substrate. Method B Off white solid (89 mg, 76%). $^{1}$H NMR (500 MHz, DMSO-$d_6$) δ 11.29 (s, 1H), 7.94 (s, 1H), 7.72 (s, 1H), 7.30 (dd, J=8.6, 1.6 Hz, 1H), 7.16 (dd, J=8.5, 0.8 Hz, 1H), 7.08 (d, J=10.4 Hz, 1H), 5.28 (s, 2H), 4.71 (s, 1H), 3.88 (dd, J=8.7, 1.4 Hz, 1H), 2.98 (d, J=8.6 Hz, 1H), 2.86-2.76 (m, 1H), 2.20 (t, J=8.6 Hz, 1H), 2.08 (d, J=4.5 Hz, 1H), 1.75-1.60 (m, 2H), 1.60-1.44 (m, 1H), 1.24-1.14 (m, 1H), 1.11-1.01 (m, 1H); $^{13}$C NMR (126 MHz, DMSO-$d_6$) δ 153.4 (d, J=240.6 Hz) 149.6, 141.5, 134.1, 133.6, 131.9, 129.8, 126.7, 119.5, 117.1, 114.3, 109.6, 93.7, 93.5, 59.9, 51.3, 42.9, 42.6, 34.2, 30.3, 28.9.

2,4-Difluoro-5-(5-fluoro-6,7,7a,8,9,10,11,11a-octahydro-3H-8,11-methanopyrazolo[4,3-a]phenanthridin-7-yl)benzonitrile (S-6)

S-6

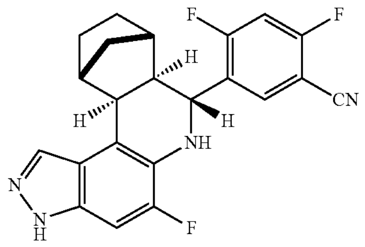

Method A Pale yellow solid (102 mg, 26%). $^{1}$H NMR (500 MHz, Methanol-$d_4$) δ 7.97 (s, 1H), 7.81 (t, J=7.4 Hz, 1H), 7.28 (t, J=9.7 Hz, 1H), 7.07 (d, J=10.4 Hz, 1H), 4.38 (d, J=7.6 Hz, 1H), 3.07 (d, J=8.6 Hz, 1H), 2.85-2.79 (m, 1H), 2.25 (t, J=8.1 Hz, 1H), 2.15-2.13 (m, 1H), 1.81-1.70 (m, 2H), 1.69-1.58 (m, 2H), 1.38-1.30 (m, 1H), 1.18-1.13 (m, 1H); $^{13}$C NMR (126 MHz, Methanol-$d_4$) δ 164.6 (d, J=257.0 Hz), 163.8 (d, J=259.56 Hz), 154.0 (d, J=244.44 Hz), 133.9, 133.6, 131.5, 130.2, 129.0, 118.8, 117.4, 112.76, 104.7 (J=23.94 Hz), 97.4 (d, J=15.12 Hz), 93.1 (d, J=25.2 Hz), 51.4, 50.4, 43.2, 42.4, 40.6, 33.5, 29.3, 28.6.

6-Fluoro-5-(5-fluoro-6,7,7a,8,9,10,11,11a-octahydro-3H-8,11-methanopyrazolo[4,3-a]phenanthridin-7-yl)-1H-indazol-3-amine (23)

23

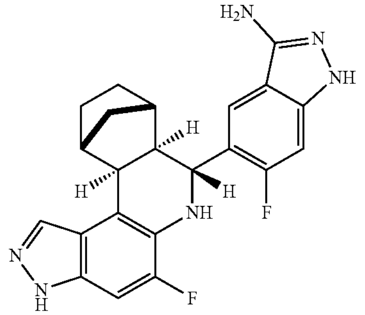

Prepared by using compound S-6 as substrate. Method B Pale yellow solid (61 mg, 50%). $^{1}$H NMR (500 MHz, Methanol-$d_4$) δ 7.99 (d, J=1.1 Hz, 1H), 7.81 (d, J=6.8 Hz, 1H), 7.05-7.02 (m, 1H), 6.99 (d, J=11.1 Hz, 1H), 4.38 (d, J=7.8 Hz, 1H), 3.14 (d, J=8.6 Hz, 1H), 2.87 (d, J=4.0 Hz, 1H), 2.41 (t, J=8.2 Hz, 1H), 2.17 (d, J=3.7 Hz, 1H), 1.82-1.74 (m, 2H), 1.67-1.62 (m, 2H), 1.39-1.32 (m, 1H), 1.20-1.14 (m, 1H); $^{13}$C NMR (126 MHz, Methanol-$d_4$) δ 164.3 (d, J=243.18 Hz), 151.3, 143.3, 141.8, 138.5, 133.4, 125.9, 124.8, 121.9, 120.9, 117.5, 113.0, 109.9, 96.6 (d, J=28.9 Hz), 55.3, 53.5, 45.1, 44.3, 41.8, 35.4, 31.8, 30.4.

5-(5-Chloro-6,7,7a,8,9,10,11,11a-Octahydro-3H-8,11-methanopyrazolo[4,3-a]phenanthridin-7-yl)-2-fluorobenzonitrile (S-7)

S-7

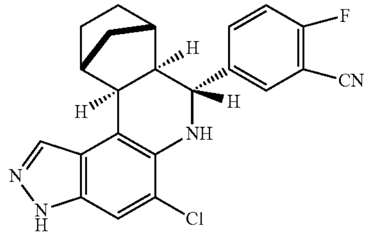

Method A Off white solid (180 mg, 46%). $^{1}$H NMR (500 MHz, DMSO-$d_6$) δ 7.92 (s, 1H), 7.88 (dd, J=6.4, 2.3 Hz, 1H), 7.73-7.68 (m, 1H), 7.41 (t, J=9.2 Hz, 1H), 7.38 (s, 1H), 5.17 (d, J=2.3 Hz, 1H), 4.22 (dd, J=5.8, 2.2 Hz, 1H), 3.05 (d, J=8.6 Hz, 1H), 2.59 (d, J=3.9 Hz, 1H), 2.38-2.13 (m, 1H), 2.11 (d, J=4.2 Hz, 1H), 1.67-1.47 (m, 4H), 1.34 (d, J=12.1 Hz, 1H), 0.99 (d, J=9.8 Hz, 1H); $^{13}$C NMR (126 MHz, DMSO-$d_6$) δ 162.7 (d, J=255.78 Hz), 143.0, 135.2, 134.6, 133.2, 131.7, 122.3, 121.7, 117.6, 116.8, 116.7, 114.6, 108.5, 100.1, 57.5, 49.5, 44.6, 42.5, 41.6, 34.6, 29.7, 29.4.

6-(5-Chloro-6,7,7a,8,9,10,11,11a-octahydro-3H-8,11-methanopyrazolo[4,3-a]phenanthridin-7-yl)-1H-indazol-3-amine (24)

24

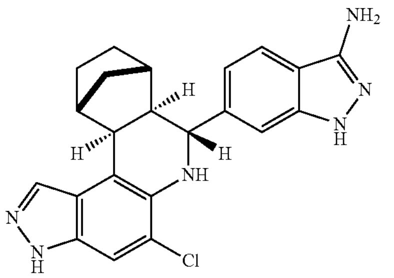

Prepared by using compound S-7 as substrate. Method B Off white solid (92 mg, 76%). $^1$H NMR (500 MHz, DMSO-$d_6$) δ 11.32 (s, 1H), 7.97 (s, 1H), 7.73 (s, 1H), 7.40 (s, 1H), 7.30 (dd, J=8.6, 1.6 Hz, 1H), 7.17 (d, J=8.5 Hz, 1H), 5.29 (s, 2H), 4.53 (s, 1H), 3.95 (d, J=8.4 Hz, 1H), 3.02 (d, J=8.6 Hz, 1H), 2.87-2.76 (m, 1H), 2.25 (t, J=8.5 Hz, 1H), 2.07 (d, J=4.2 Hz, 1H), 1.71-1.61 (m, 2H), 1.60-1.48 (m, 1H), 1.22 (d, J=11.8 Hz, 1H), 1.04 (d, J=9.8 Hz, 1H); $^{13}$C NMR (126 MHz, DMSO-$d_6$) δ 149.6, 141.5, 135.6, 134.7, 133.8, 132.0, 126.6, 122.4, 121.7, 119.4, 117.1, 114.3, 109.8, 108.3, 60.2, 51.3, 43.4, 42.9, 34.2, 30.2, 28.9.

5-(5-Bromo-6,7,7a,8,9,10,11,11a-octahydro-3H-8,11-methanopyrazolo[4,3-a]phenanthridin-7-yl)-2-fluorobenzonitrile (S-8)

S-8

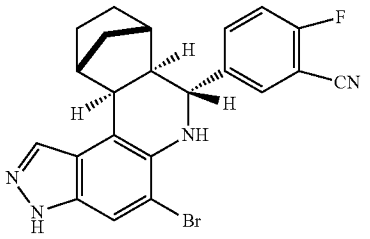

Method A Off white solid (170 mg, 49%). $^1$H NMR (500 MHz, DMSO-$d_6$) δ 7.92 (d, J=1.1 Hz, 1H), 7.88 (dd, J=6.3, 2.4 Hz, 1H), 7.71 (ddd, J=8.8, 5.4, 2.4 Hz, 1H), 7.56 (d, J=0.9 Hz, 1H), 7.41 (t, J=9.1 Hz, 1H), 4.24 (d, J=5.6 Hz, 1H), 3.06 (d, J=8.6 Hz, 1H), 2.58 (d, J=3.9 Hz, 1H), 2.28 (dd, J=8.7, 5.6 Hz, 1H), 2.16-2.07 (m, 1H), 1.67-1.46 (m, 4H), 1.37-1.29 (m, 1H), 1.02-0.95 (m, 1H); $^{13}$C NMR (126 MHz, DMSO-$d_6$) δ 162.8 (d, J=255.7 Hz), 143.0, 135.6, 135.2, 133.1, 131.5, 122.8, 117.8, 116.9, 116.7, 114.6, 112.8, 112.0, 100.2, 57.7, 49.6, 44.6, 42.6, 41.6, 34.6, 29.7, 29.4.

6-(5-Bromo-6,7,7a,8,9,10,11,11a-octahydro-3H-8,11-methanopyrazolo[4,3-a]phenanthridin-7-yl)-1H-indazol-3-amine (25)

25

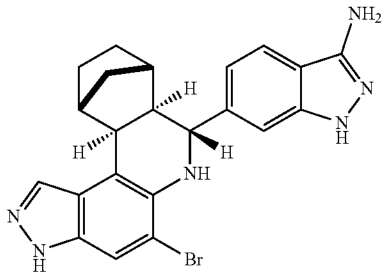

Prepared by using compound S-8 as substrate. Method B Off-white solid (108 mg, 80%). $^1$H NMR (500 MHz, DMSO-$d_6$) δ 11.34 (s, 2H), 7.97 (s, 2H), 7.74 (s, 2H), 7.57 (s, 2H), 7.31 (dd, J=8.6, 1.6 Hz, 2H), 7.18 (d, J=8.5 Hz, 2H), 5.29 (s, 4H), 4.41 (d, J=1.4 Hz, 2H), 3.94 (d, J=8.6 Hz, 2H), 3.03 (d, J=8.6 Hz, 2H), 2.86-2.81 (m, 2H), 2.25 (t, J=8.6 Hz, 2H), 2.06 (d, J=4.2 Hz, 2H), 1.70 (d, J=9.9 Hz, 2H), 1.68-1.61 (m, 1H), 1.59 (s, 2H), 1.59-1.46 (m, 2H), 1.21 (s, 2H), 1.04 (d, J=9.8 Hz, 2H); $^{13}$C NMR (126 MHz, DMSO-$d_6$) δ 149.6, 141.5, 136.3, 135.5, 133.7, 132.0, 126.6, 123.0, 119.5, 117.2, 114.3, 112.9, 111.5, 109.8, 60.4, 51.5, 43.6, 42.9, 34.2, 30.2, 28.8.

2-Fluoro-5-(5-methoxy-6,7,7a,8,9,10,11,11a-octahydro-3H-8,11-methanopyrazolo[4,3-a]phenanthridin-7-yl)benzonitrile (S-9)

S-9

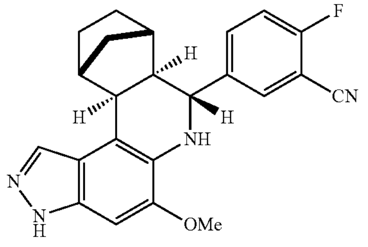

Method A Off-white solid (113 mg, 29%). $^1$H NMR (500 MHz, DMSO-$d_6$) δ 7.90 (dd, J=6.4, 2.3 Hz, 1H), 7.80 (s, 1H), 7.78-7.73 (m, 1H), 7.43 (t, J=9.0 Hz, 1H), 6.72 (s, 1H), 4.71 (s, 1H), 3.97 (d, J=7.2 Hz, 1H), 3.79 (s, 3H), 2.92 (d, J=8.7 Hz, 1H), 2.71 (d, J=3.9 Hz, 1H), 2.15 (t, J=8.0 Hz, 1H), 2.02 (d, J=4.0 Hz, 1H), 1.72-1.57 (m, 2H), 1.57-1.44 (m, 2H), 1.35-1.18 (m, 1H), 1.00 (d, J=9.8 Hz, 1H); $^{13}$C NMR (126 MHz, DMSO-$d_6$) δ 162.9 (J=254.5 Hz), 148.7, 143.2, 135.5, 135.1, 133.3, 131.5, 130.6, 116.9, 116.7, 115.0, 114.6, 100.2, 88.7, 58.1, 56.0, 50.4, 43.0, 42.6, 34.3, 29.9, 29.2.

6-(5-Methoxy-6,7,7a,8,9,10,11,11a-octahydro-3H-8,11-methanopyrazolo[4,3-a]phenanthridin-7-yl)-1H-indazol-3-amine (26)

26

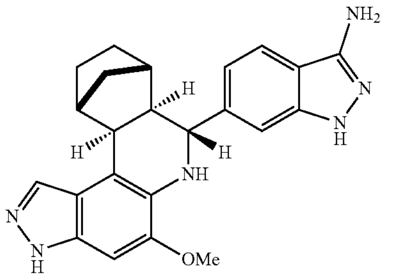

Prepared by using compound S-9 as substrate. Method B Off-white solid (94 mg, 78%). $^{1}$H NMR (500 MHz, DMSO-$d_6$) δ 11.32 (s, 1H), 7.92-7.71 (m, 2H), 7.37-7.15 (m, 2H), 6.73 (s, 1H), 5.29 (s, 2H), 4.28 (d, J=1.3 Hz, 1H), 3.78 (s, 3H), 3.74 (d, J=9.5 Hz, 1H), 2.92-2.87 (m, 2H), 2.17 (t, J=9.0 Hz, 1H), 2.03 (d, J=4.2 Hz, 1H), 1.69 (d, J=9.9 Hz, 1H), 1.63 (dt, J=11.2, 4.2 Hz, 1H), 1.58-1.45 (m, 2H), 1.18-1.12 (m, 1H), 1.04 (d, J=9.8 Hz, 1H); $^{13}$C NMR (126 MHz, DMSO-$d_6$) δ 149.6, 148.6, 141.6, 135.1, 134.1, 131.7, 126.7, 119.6, 117.0, 114.6, 114.3, 109.7, 88.5, 60.6, 56.0, 52.0, 43.3, 41.7, 34.0, 30.5, 28.6.

2,4-Difluoro-5-(6,7,7a,8,9,10,11,11a-octahydro-3H-8,11-methanopyrazolo[4,3-a]phenanthridin-7-yl) benzonitrile (S-10)

S-10

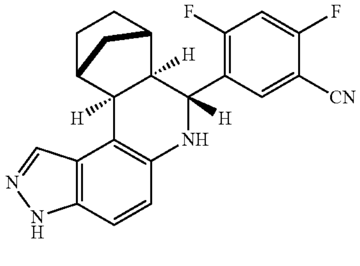

Method A Pale yellow solid (120 mg, 32%). $^{1}$H NMR (500 MHz, DMSO-$d_6$) δ 7.95 (t, J=7.5 Hz, 1H), 7.87 (s, 1H), 7.66 (t, J=9.9 Hz, 1H), 7.15 (d, J=8.7 Hz, 1H), 6.78 (d, J=8.7 Hz, 1H), 5.49 (s, 1H), 4.17 (dd, J=8.0, 1.5 Hz, 1H), 2.91 (d, J=8.6 Hz, 1H), 2.74 (s, 1H), 2.16 (t, J=8.3 Hz, 1H), 1.99 (s, 1H), 1.63 (t, J=10.9 Hz, 2H), 1.52 (td, J=12.0, 10.1, 5.0 Hz, 2H), 1.27-1.18 (m, 1H), 1.03 (d, J=9.9 Hz, 1H); $^{13}$C NMR (126 MHz, DMSO-$d_6$) δ 164.6 (d, J=257.7 Hz), 163.4 (d, J=255.7 Hz), 139.4, 136.0, 134.8, 131.5, 130.9 (d, J=15.1 Hz), 123.2, 118.3, 114.1, 113.9, 108.8, 106.0, 97.3 (d, J=15.1 Hz), 52.1, 50.3, 42.8, 42.5, 34.2, 30.0, 29.0.

6-Fluoro-5-(6,7,7a,8,9,10,11,11a-octahydro-3H-8,11-methanopyrazolo[4,3-a]phenanthridin-7-yl)-1H-indazol-3-amine (27)

27

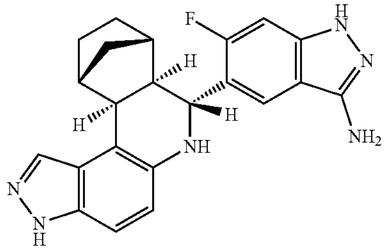

Prepared by using compound S-10 as substrate. Method B Pale yellow solid (73 mg, 63%). $^{1}$H NMR (500 MHz, Methanol-$d_4$) δ 7.98 (d, J=1.1 Hz, 1H), 7.83 (d, J=6.8 Hz, 1H), 7.19 (d, J=8.7 Hz, 1H), 6.98 (d, J=10.9 Hz, 1H), 6.87 (d, J=8.7 Hz, 1H), 4.28 (d, J=9.1 Hz, 1H), 3.04 (d, J=8.5 Hz, 1H), 2.94 (d, J=3.9 Hz, 1H), 2.36 (t, J=8.9 Hz, 1H), 2.09 (s, 1H), 1.81 (d, J=10.0 Hz, 1H), 1.76-1.70 (m, 1H), 1.66-1.58 (m, 2H), 1.33-1.25 (m, 1H), 1.16-1.11 (m, 1H).

$^{13}$C NMR (126 MHz, Methanol-$d_4$) δ 162.41 (d, J=245.7 Hz), 149.3, 141.4, 139.8, 131.5, 123.9, 123.8, 122.8, 119.9, 119.0, 115.6, 111.1, 108.0, 94.6 (d, J=30.6 Hz), 53.3, 51.6, 43.2, 42.3, 39.8, 33.4, 29.8, 28.4.

N-(5-(6,7,7a,8,9,10,11,11a-octahydro-3H-8,11-Methanopyrazolo[4,3-a]phenanthridin-7-yl)-1H-indazol-3-yl)cyclopropanecarboxamide (28)

28

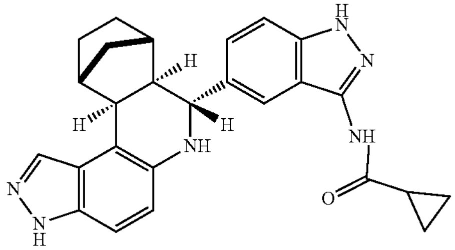

To a solution of Compound HSD1787 (0.3 mmol) in pyridine (1.5 mL) at 0° C. was added cyclopropanecarbonyl chloride (0.3 mmol) dropwise and continued to stir for 5 h. After completion, reaction mixture was concentrated and residue was purified by using silica gel chromatography to get the desired compound. Off-white solid (67 mg, 51%).

$^{1}$H NMR (500 MHz, DMSO-$d_6$) δ 10.55 (s, 1H), 7.87 (s, 1H), 7.79 (s, 1H), 7.44-7.35 (m, 2H), 7.10 (d, J=8.7 Hz, 1H), 6.83 (d, J=8.7 Hz, 1H), 5.29 (s, 1H), 3.77 (d, J=9.4 Hz, 1H), 2.90-2.81 (m, 2H), 2.09 (t, J=9.1 Hz, 1H), 2.00 (d, J=4.3 Hz, 1H), 1.94-1.87 (m, 1H), 1.70 (d, J=9.8 Hz, 1H), 1.66-1.57 (m, 1H), 1.54-1.44 (m, 2H), 1.17-1.10 (m, 1H), 1.03 (d, J=9.7 Hz, 1H), 0.87-0.71 (m, 4H); $^{13}$C NMR (126 MHz, DMSO-$d_6$) δ 172.1, 141.1, 140.8, 140.5, 136.6, 135.9, 131.6, 127.3, 123.3, 121.5, 118.6, 116.5, 113.7, 110.2, 108.4, 60.9, 52.2, 43.1, 41.8, 34.1, 30.4, 28.7, 14.1, 7.6.

6-(6,7,7a,8,9,10,11,11a-Octahydro-3H-8,11-methanopyrazolo[4,3-a]phenanthridin-7-yl)benzo[d]thiazol-2-amine (29)

29

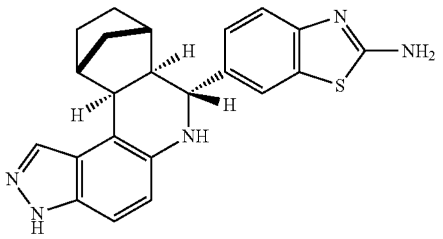

Method A Yellow solid (116 mg, 30%). $^{1}$H NMR (500 MHz, DMSO-$d_6$) δ 7.88-7.83 (m, 1H), 7.70-7.64 (m, 1H), 7.38 (d, J=8.4 Hz, 2H), 7.29-7.22 (m, 2H), 7.09 (t, J=8.1 Hz, 1H), 6.84-6.78 (m, 1H), 5.33 (d, J=7.6 Hz, 1H), 3.75 (t, J=8.3 Hz, 1H), 2.89-2.79 (m, 3H), 2.11-2.06 (m, 1H), 2.05-1.98 (m, 1H), 1.74-1.68 (m, 1H), 1.65-1.59 (m, 1H), 1.55-1.43 (m, 3H), 1.23-1.12 (m, 2H), 1.01 (t, J=8.3 Hz, 1H); $^{13}$C NMR (126 MHz, DMSO-$d_6$) δ 166.7, 152.5, 140.5, 138.4, 135.9, 131.5, 131.3, 125.8, 123.3, 120.5, 118.5, 117.6, 113.9, 108.4, 60.3, 52.0, 43.0, 42.1, 34.1, 30.4, 28.8.

2-Fluoro-4-(6,7,7a,8,9,10,11,11a-octahydro-3H-8,11-methanopyrazolo[4,3-a]phenanthridin-7-yl)benzonitrile (S-11)

S-11

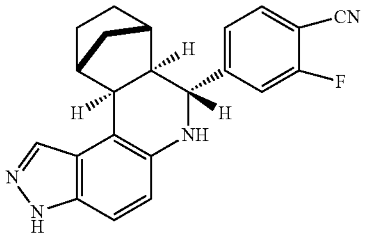

Method A Off-white solid (161 mg, 45%). $^{1}$H NMR (500 MHz, DMSO-$d_6$) δ 7.89-7.75 (m, 2H), 7.51 (dd, J=10.8, 1.5 Hz, 1H), 7.42 (dd, J=8.1, 1.5 Hz, 1H), 7.13 (d, J=8.7 Hz, 1H), 6.79 (d, J=8.8 Hz, 1H), 5.63 (s, 1H), 4.03 (d, J=7.1 Hz, 1H), 2.88 (d, J=8.6 Hz, 1H), 2.69 (d, J=4.0 Hz, 1H), 2.48 (p, J=1.8 Hz, 1H), 2.11 (t, J=7.9 Hz, 1H), 1.68 (d, J=9.5 Hz, 1H), 1.62-1.56 (m, 1H), 1.56-1.44 (m, 2H), 1.28-1.18 (m, 1H), 1.00 (d, J=9.9 Hz, 1H); $^{13}$C NMR (126 MHz, DMSO-$d_6$) δ 163.8 (J=255.78 Hz), 155.6, 139.2, 135.9, 134.0, 131.4, 125.2, 123.2, 118.3, 116.0, 115.9, 114.5, 108.7, 98.8, 59.1, 50.7, 43.2, 42.4, 34.4, 29.8, 29.3.

6-(6,7,7a,8,9,10,11,11a-Octahydro-3H-8,11-methanopyrazolo[4,3-a]phenanthridin-7-yl)-1H-indazol-3-amine (30)

30

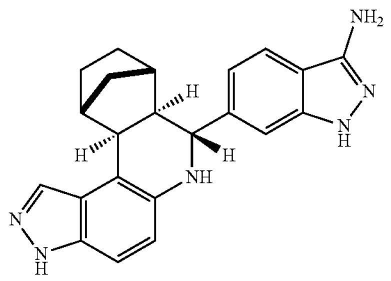

Prepared by using S-11 as substrate. Method B Pale yellow solid (108 mg, 30%). $^{1}$H NMR (500 MHz, DMSO-$d_6$) δ 11.25 (s, 1H), 7.86 (s, 1H), 7.60 (d, J=8.3 Hz, 1H), 7.20 (s, 1H), 7.10 (d, J=8.7 Hz, 1H), 6.98 (dd, J=8.4, 1.3 Hz, 1H), 6.83 (d, J=8.8 Hz, 1H), 5.38 (s, 1H), 5.25 (s, 2H), 3.85 (d, J=8.5 Hz, 1H), 2.85 (d, J=8.6 Hz, 1H), 2.80 (d, J=3.8 Hz, 1H), 2.12 (t, J=8.6 Hz, 1H), 2.08-2.04 (m, 1H), 1.72 (d, J=9.8 Hz, 1H), 1.65-1.56 (m, 1H), 1.56-1.44 (m, 2H), 1.26-1.12 (m, 1H), 1.02 (d, J=9.7 Hz, 1H); $^{13}$C NMR (126 MHz, DMSO-$d_6$) δ 149.4, 143.9, 142.1, 140.4, 135.9, 131.5, 123.3, 120.3, 118.5, 118.4, 113.9, 113.8, 108.5, 108.4, 60.7, 51.9, 42.9, 42.3, 34.1, 30.3, 28.9. HRMS (ESI) m/z calcd for $C_{22}H_{23}N_6$[M+H]$^+$ 371.1984, found 371.1978.

2-Fluoro-5-(6,7,7a,8,9,10,11,11a-octahydro-1H-8,11-methanopyrazolo[3,4-a]phenanthridin-7-yl)benzonitrile (S-12)

S-12

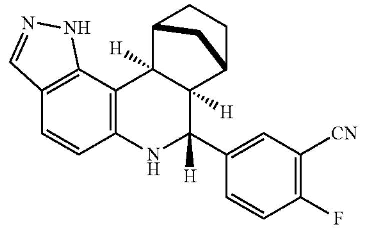

Method A Pale yellow solid (179 mg, 50%). $^{1}$H NMR (500 MHz, DMSO-$d_6$) δ 7.86 (dd, J=6.4, 2.3 Hz, 1H), 7.78 (s, 1H), 7.70 (ddd, J=8.2, 5.3, 2.3 Hz, 1H), 7.41 (t, J=9.1 Hz, 1H), 7.26 (d, J=8.5 Hz, 1H), 6.52 (d, J=8.4 Hz, 1H), 5.97-5.93 (m, 1H), 4.14 (d, J=5.8 Hz, 1H), 2.86 (d, J=8.7 Hz, 1H), 2.55 (d, J=3.5 Hz, 1H), 2.19 (dd, J=8.6, 5.5 Hz, 1H), 2.11 (d, J=4.0 Hz, 1H), 1.64 (d, J=9.8 Hz, 1H), 1.63-1.52 (m, 2H), 1.48 (dq, J=11.4, 6.0, 5.3 Hz, 1H), 1.29 (dt, J=8.8, 4.8 Hz, 1H), 0.98 (d, J=9.7 Hz, 1H); $^{13}$C NMR (126 MHz, DMSO-$d_6$) δ 162.6 (254.52 Hz), 143.9, 143.7, 140.6, 135.3, 135.2, 134.1, 133.2, 118.8, 117.3, 116.8, 116.6, 114.6, 113.0, 105.5, 100.0, 99.9, 57.3, 49.7, 42.7, 41.8, 34.6, 29.6; HRMS (ESI) m/z calcd for $C_{22}H_{20}FN_4$ [M+H]$^+$ 359.1672, found 359.1667.

5-(6,7,7a,8,9,10,11,11a-Octahydro-1H-8,11-methanopyrazolo[3,4-a]phenanthridin-7-yl)-1H-indazol-3-amine (31)

31

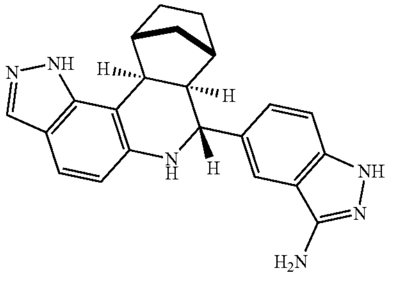

Prepared by using S-12 as substrate. Method B Off-white solid (98 mg, 88%). $^{1}$H NMR (500 MHz, DMSO-$d_6$) δ 11.28 (s, 1H), 7.79 (s, 1H), 7.71 (s, 1H), 7.33-7.21 (m, 2H), 7.16 (d, J=8.6 Hz, 1H), 6.57 (d, J=8.4 Hz, 1H), 5.70 (s, 1H), 5.27 (s, 2H), 3.86 (d, J=8.2 Hz, 1H), 3.09 (s, 1H), 2.82 (d, J=8.6 Hz, 1H), 2.75 (s, 1H), 2.14 (t, J=8.4 Hz, 1H), 2.11-2.04 (m, 1H), 1.68 (d, J=9.7 Hz, 1H), 1.62-1.54 (m, 2H), 1.52-1.41 (m, 1H), 1.21-1.11 (m, 1H), 1.06-0.99 (m, 1H); $^{13}$C NMR (126 MHz, DMSO-$d_6$) δ 149.5, 145.2, 141.4, 141.0, 134.7, 134.1, 126.6, 119.6, 118.4, 117.2, 114.3, 113.3, 109.5, 104.7, 60.0, 51.4, 41.0, 40.9, 34.1, 30.6, 28.8.

5-(8,9,10,11-tetrahydro-3H-8,11-Methanopyrazolo[4,3-a]phenanthridin-7-yl)-1H-indazol-3-amine (32)

32

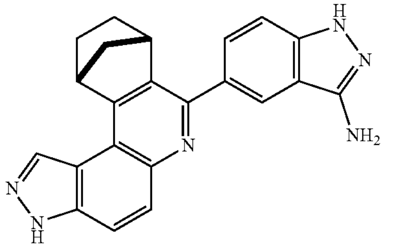

Synthesized by oxidation of HSD1787. To a reaction mixture of Compound HSD1787 (0.3 mmol) dissolved in acetonitrile (5 mL) was added DDQ (1.5 equiv) and reaction stirred for 8 h at room temperature. After completion, reaction mixture was diluted with ethyl acetate and washed with aqueous solution of sodium hydroxide followed by washing with brine. Organic layer was concentrated and purified by silica gel column chromatography. Brown solid (49 mg, 45%).

$^{1}$H NMR (500 MHz, DMSO-$d_6$) δ 11.53 (s, 1H), 8.68 (s, 1H), 7.87 (d, J=9.6 Hz, 1H), 7.84-7.74 (m, 2H), 7.37 (d, J=8.6 Hz, 1H), 5.52 (s, 2H), 4.34 (s, 1H), 3.86 (d, J=3.3 Hz, 1H), 2.27-2.11 (m, 2H), 1.84 (d, J=8.8 Hz, 1H), 1.69 (d, J=8.7 Hz, 1H), 1.47-1.32 (m, 1H), 1.32-1.20 (m, 1H); $^{13}$C NMR (126 MHz, DMSO-$d_6$) δ 152.4, 150.4, 144.9, 141.6, 139.5, 138.0, 134.9, 129.9, 129.5, 127.8, 121.3, 116.3, 115.9, 114.7, 114.4, 109.6, 49.9, 43.4, 42.6, 27.1, 25.5.

2-Fluoro-5-(2,3,4a,6,9,11c-hexahydro-5H-[1,4]dioxino[2,3-c]pyrazolo[4,3-f]quinolin-5-yl)benzonitrile (S-13)

S-13

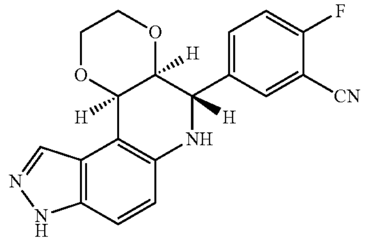

Method A Pale yellow solid (126 mg, 36%). $^{1}$H NMR (500 MHz, DMSO-$d_6$) δ 8.02-7.99 (m, 1H), 7.96-7.92 (m, 1H), 7.89 (d, J=1.0 Hz, 1H), 7.53 (t, J=9.1 Hz, 1H), 7.27 (d, J=8.9 Hz, 1H), 6.81 (d, J=8.8 Hz, 1H), 5.81 (s, 1H), 5.29 (d, J=3.5 Hz, 1H), 4.65 (s, 1H), 3.92-3.84 (m, 1H), 3.59-3.48 (m, 2H), 3.38-3.35 (m, 1H), 3.26-3.20 (m, 1H); $^{13}$C NMR (126 MHz, DMSO-$d_6$) δ 163.1 (J=255.7 Hz), 139.9, 139.0, 136.1, 133.4, 122.4, 122.0, 119.8, 118.3, 116.6, 116.4, 114.6, 106.7, 99.7, 72.3, 70.4, 66.3, 59.7, 57.3.

5-(2,3,4a,6,9,11c-Hexahydro-5H-[1,4]dioxino[2,3-c]pyrazolo[4,3-f]quinolin-5-yl)-1H-indazol-3-amine (33)

33

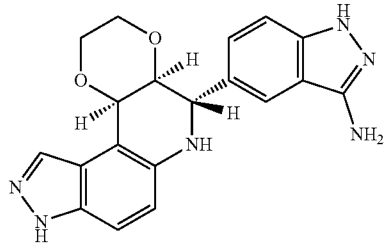

Prepared by using compound S-13 as substrate. Method B Pale yellow solid (88 mg, 81%). $^{1}$H NMR (500 MHz, DMSO-$d_6$) δ 11.28 (s, 1H), 7.88 (d, J=4.5 Hz, 2H), 7.39 (dd, J=8.6, 1.6 Hz, 1H), 7.24 (d, J=8.7 Hz, 1H), 7.18 (d, J=8.5 Hz, 1H), 6.85 (d, J=8.8 Hz, 1H), 5.70 (s, 1H), 5.35 (d, J=3.5 Hz, 1H), 5.29 (s, 2H), 4.59 (s, 1H), 3.83 (d, J=3.6 Hz, 1H), 3.57-3.45 (m, 2H), 3.40-3.34 (m, 1H), 3.24 (td, J=11.4, 3.1 Hz, 1H); $^{13}$C NMR (126 MHz, DMSO-$d_6$) δ 149.6, 141.7, 140.7, 135.5, 132.2, 130.2, 127.2, 122.3, 119.9, 118.3, 114.2, 110.3, 109.0, 106.4, 73.3, 70.8, 66.2, 59.7, 59.1.

(3-(6,7,7a,8,11,11a-Hexahydro-3H-8,11-methanopyrazolo[4,3-a]phenanthridin-7-yl)-2-methoxyphenyl) boronic acid

HSD1792

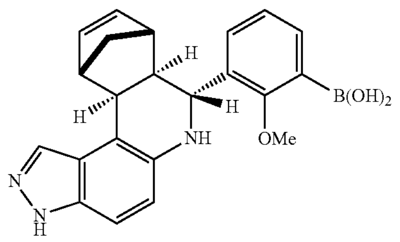

Method A Off-white solid (102 mg, 26%). $^{1}$H NMR (500 MHz, Methanol-$d_4$) δ 8.10 (s, 1H), 7.47 (dd, J=7.7, 1.7 Hz, 1H), 7.22-7.13 (m, 2H), 7.04 (t, J=7.4 Hz, 1H), 6.88 (d, J=8.7 Hz, 1H), 6.42 (dd, J=5.7, 2.9 Hz, 1H), 6.11 (dd, J=5.7, 3.0 Hz, 1H), 4.42 (d, J=8.4 Hz, 1H), 3.79 (s, 3H), 3.49 (s, 1H), 2.85 (d, J=8.4 Hz, 1H), 2.72-2.65 (m, 1H), 2.09 (t, J=8.4 Hz, 1H), 1.83 (d, J=8.7 Hz, 1H), 1.31 (d, J=1.6 Hz, 1H). $^{13}$C NMR (126 MHz, Methanol-$d_4$) δ 160.4, 140.3, 137.8, 136.3, 135.7, 131.7, 131.3, 128.8, 123.1, 122.8, 118.8, 115.7, 108.1, 60.4, 55.2, 45.8, 45.6, 43.2, 38.5.

(3-(2,3,4a,6,9,11c-Hexahydro-5H-[1,4]dioxino[2,3-c]pyrazolo[4,3-f]quinolin-5-yl)-2-methoxyphenyl) boronic acid

HSD1799

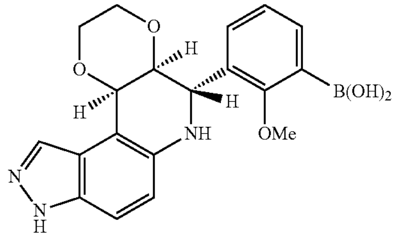

Method A Off-white solid (141 mg, 37%). $^{1}$H NMR (500 MHz, Methanol-$d_4$) δ 8.10 (s, 1H), 7.48 (d, J=7.7 Hz, 1H), 7.24-7.16 (m, 3H), 7.05 (t, J=7.5 Hz, 1H), 6.90 (d, J=8.7 Hz, 2H), 6.43 (dd, J=5.8, 2.9 Hz, 1H), 6.12 (dd, J=5.9, 3.0 Hz, 1H), 4.42 (d, J=8.5 Hz, 1H), 3.80 (s, 4H), 3.50 (s, 1H), 2.86 (d, J=8.4 Hz, 1H), 2.68 (s, 1H), 2.10 (t, J=8.4 Hz, 1H), 1.84 (d, J=8.7 Hz, 1H), 1.31 (d, J=8.7 Hz, 2H); $^{13}$C NMR (126 MHz, Methanol-$d_4$) δ 160.5, 140.3, 137.7, 136.3, 135.7, 131.7, 131.3, 128.8, 123.1, 122.8, 118.8, 115.8, 108.0, 60.4, 55.3, 45.8, 45.5, 43.2, 38.5.

1-Methyl-7-(1-methyl-3-(trifluoromethyl)-1H-pyrazol-4-yl)-6,7,7a,8,9,10,11,11a-octahydro-3H-8,11-methanopyrazolo[4,3-a]phenanthridine

HSD1817

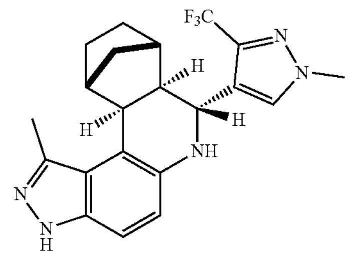

Method A Off-white solid (111 mg, 28%). $^{1}$H NMR (500 MHz, Methanol-$d_4$) δ 7.12-7.02 (m, 2H), 6.67 (dd, J=8.7, 1.5 Hz, 1H), 4.47 (s, 1H), 3.66 (s, 3H), 3.38 (d, J=8.7 Hz, 1H), 2.66 (s, 3H) 2.36 (d, J=4.2 Hz, 1H), 2.21 (d, J=8.1 Hz, 2H), 1.96-1.87 (m, 1H), 1.73-1.64 (m, 1H), 1.63-1.51 (m, 1H), 1.46-1.38 (m, 1H), 1.03-0.92 (m, 1H); $^{13}$C NMR (126 MHz, Methanol-$d_4$) δ 140.2, 137.8, 137.2, 131.6, 130.2, 125.9, 123.1 (J=268.3 Hz), 120.4, 119.3, 117.7, 108.4, 49.8, 49.3, 47.0, 44.4, 40.7, 37.9, 33.9, 30.6, 28.0.

7-(1-Methyl-3-(trifluoromethyl)-1H-pyrazol-4-yl)-6,7,7a,8,9,10,11,11a-octahydro-3H-8,11-methanopyrrolo[3,2-a]phenanthridine

HSD1818

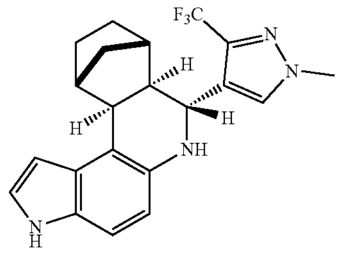

Method A Off-white solid (90 mg, 23%). $^{1}$H NMR (500 MHz, Methanol-$d_4$) δ 7.31 (d, J=1.3 Hz, 1H), 7.15 (d, J=3.1 Hz, 1H), 7.05 (dd, J=8.4, 0.9 Hz, 1H), 6.50 (d, J=8.5 Hz, 1H), 6.38 (dd, J=3.1, 0.9 Hz, 1H), 4.23 (d, J=6.0 Hz, 1H), 3.76 (s, 3H), 3.02 (d, J=8.6 Hz, 1H), 2.86-2.71 (m, 1H), 2.24-2.14 (m, 1H), 2.14-2.08 (m, 1H), 1.76-1.65 (m, 2H), 1.65-1.49 (m, 2H), 1.41-1.33 (m, 1H), 1.02 (dd, J=9.9, 1.5 Hz, 1H); $^{13}$C NMR (126 MHz, Methanol-$d_4$) δ 138.3, 136.7, 131.6, 130.8, 127.3, 125.1, 123.8, 123.0, 122.2 (J=268.3), 117.0, 112.1, 109.4, 99.2, 51.0, 50.1, 43.1, 42.4, 41.7, 38.0, 33.7, 29.5, 29.0.

2-Fluoro-5-(6,7,7a,8,11,11a-hexahydro-3H-8,11-methanopyrazolo[4,3-a]phenanthridin-7-yl)benzonitrile

HSD1831

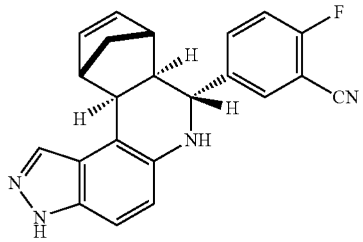

Method A Off-white solid (160 mg, 45%). $^1$H NMR (500 MHz, Methanol-$d_4$) δ 8.09 (d, J=1.1 Hz, 1H), 7.80 (dd, J=6.3, 2.3 Hz, 1H), 7.76 (ddd, J=8.7, 5.2, 2.3 Hz, 1H), 7.30 (t, J=8.9 Hz, 1H), 7.21 (d, J=8.7 Hz, 1H), 6.89 (d, J=8.8 Hz, 1H), 6.44 (dd, J=5.7, 3.0 Hz, 1H), 6.13 (dd, J=5.7, 3.0 Hz, 1H), 3.97 (d, J=8.3 Hz, 1H), 3.51-3.43 (m, 1H), 2.86 (d, J=8.5 Hz, 1H), 2.67 (dd, J=3.2, 1.6 Hz, 1H), 2.00 (td, J=8.4, 1.4 Hz, 1H), 1.80 (dt, J=8.9, 1.6 Hz, 1H), 1.32 (dt, J=8.8, 1.7 Hz, 1H); $^{13}$C NMR (126 MHz, Methanol-$d_4$) δ 163.2 (J=257.0 Hz), 142.7, 139.4, 137.8, 136.1, 134.7, 132.6, 131.3, 122.6, 118.6, 116.0, 115.8, 113.4, 108.3, 100.4, 61.5, 46.1, 45.3, 43.1, 38.2.

7-(3-Fluoro-1H-indazol-5-yl)-6,7,7a,8,9,10,11,11a-octahydro-3H-8,11-methanopyrazolo[4,3-a]phenanthridine

HSD1832

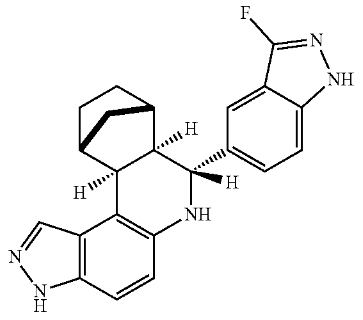

Method A Off-white solid (86 mg, 23%). $^1$H NMR (500 MHz, DMSO-$d_6$) δ 7.86 (s, 1H), 7.66 (s, 1H), 7.53 (dd, J=8.7, 1.6 Hz, 1H), 7.44 (dd, J=8.8, 2.2 Hz, 1H), 7.11 (d, J=8.7 Hz, 1H), 6.82 (d, J=8.7 Hz, 1H), 5.39 (s, 1H), 3.90 (d, J=8.7 Hz, 1H), 2.87 (d, J=8.6 Hz, 1H), 2.81 (d, J=3.9 Hz, 1H), 2.13 (t, J=8.7 Hz, 1H), 2.03 (d, J=4.1 Hz, 1H), 1.73 (d, J=9.7 Hz, 1H), 1.67-1.59 (m, 1H), 1.55-1.44 (m, 2H), 1.21-1.11 (m, 1H), 1.02 (d, J=9.7 Hz, 1H); $^{13}$C NMR (126 MHz, DMSO-$d_6$) δ 157.7 (J=243.1), 141.4, 140.3, 138.3, 135.9, 131.5, 128.6, 123.3, 118.5, 117.0, 114.0, 111.2, 108.4, 107.6 (25.2 Hz), 60.1, 51.7, 42.9, 42.3, 34.1, 31.1, 30.3, 28.9.

7-(1-Methyl-3-(trifluoromethyl)-1H-pyrazol-4-yl)-6,7,7a,8,9,10,11,11a-octahydro-8,11-methanoisothiazolo[4,5-a]phenanthridine

HSD1845

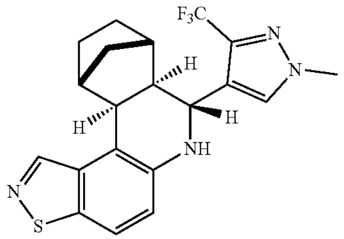

Method A Pale yellow solid (158 mg, 39%). $^1$H NMR (500 MHz, DMSO-$d_6$) δ 8.94 (d, J=1.0 Hz, 1H), 7.70 (dt, J=8.7, 0.8 Hz, 1H), 7.47 (d, J=1.2 Hz, 1H), 6.98 (d, J=8.6 Hz, 1H), 5.82 (d, J=1.9 Hz, 1H), 4.25 (dd, J=4.5, 2.0 Hz, 1H), 3.75 (s, 3H), 3.25 (d, J=8.6 Hz, 1H), 2.42 (s, 1H), 2.13 (dd, J=9.1, 4.3 Hz, 2H), 1.60 (td, J=7.9, 6.4, 2.4 Hz, 3H), 1.53 (td, J=9.5, 8.1, 3.9 Hz, 1H), 1.33-1.24 (m, 1H), 0.97 (dt, J=9.7, 1.5 Hz, 1H); $^{13}$C NMR (126 MHz, DMSO-$d_6$) δ 153.6, 143.0, 142.7, 137.5, 137.2, 136.2, 131.4, 125.1, 123.6, 121.4, 119.6, 119.3, 118.2, 50.6, 48.7, 46.0, 42.5, 41.4, 34.4, 30.1, 29.2.

5-(6,7,7a,8,11,11a-Hexahydro-3H-8,11-methanopyrazolo[4,3-a]phenanthridin-7-yl)-1H-indazol-3-amine

HSD1880

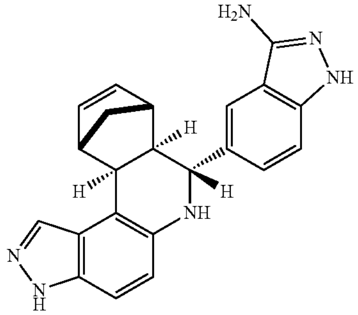

Prepared by using compound HSD1831 as substrate. Method B Off-white solid (91 mg, 82%). $^1$H NMR (500 MHz, Methanol-$d_4$) δ 7.98 (d, J=1.1 Hz, 1H), 7.73 (d, J=1.6 Hz, 1H), 7.46 (dd, J=8.7, 1.7 Hz, 1H), 7.29 (d, J=8.7 Hz, 1H), 7.22-7.16 (m, 1H), 6.87 (d, J=8.7 Hz, 1H), 3.87 (d, J=10.0 Hz, 1H), 3.03-2.94 (m, 2H), 2.30 (t, J=9.3 Hz, 1H), 2.08 (d, J=4.1 Hz, 1H), 1.83-1.76 (m, 1H), 1.77-1.67 (m, 1H), 1.61-1.49 (m, 2H), 1.27-1.20 (m, 1H), 1.17-1.07 (m, 1H). $^{13}$C NMR (126 MHz, Methanol-$d_4$) δ 149.0, 141.8, 139.9, 136.6, 134.6, 131.4, 127.3, 122.8, 119.0, 118.9, 115.6, 113.7, 109.4, 108.0, 61.7, 51.9, 43.2, 41.9, 39.2, 33.2, 30.0, 28.1.

5-(6-Methyl-6,7,7a,8,9,10,11,11a-octahydro-3H-8,11-methanopyrazolo[4,3-a]phenanthridin-7-yl)-1H-indazol-3-amine

HSD1897

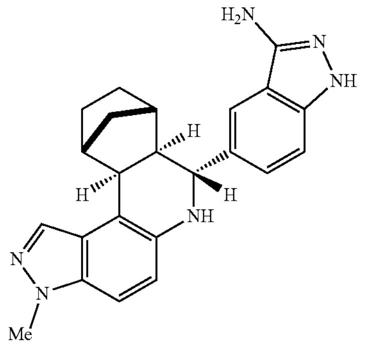

Prepared by using compound S-13 as substrate. Method B Off-white solid (96 mg, 83%). $^{1}H$ NMR (500 MHz, DMSO-$d_6$) δ 7.87 (s, 1H), 7.75 (s, 1H), 7.36 (dd, J=8.7, 1.6 Hz, 1H), 7.26 (d, J=8.6 Hz, 1H), 7.10 (d, J=8.7 Hz, 1H), 6.84 (d, J=8.7 Hz, 1H), 5.38 (s, 2H), 5.29 (s, 1H), 3.74 (d, J=9.6 Hz, 1H), 3.69 (s, 3H), 2.86 (dd, J=15.0, 6.3 Hz, 2H), 2.10 (t, J=9.0 Hz, 1H), 2.02 (d, J=4.3 Hz, 1H), 1.71 (d, J=9.9 Hz, 1H), 1.65-1.58 (m, 1H), 1.55-1.45 (m, 2H), 1.19-1.09 (m, 1H), 1.08-1.00 (m, 1H); $^{13}C$ NMR (126 MHz, DMSO-$d_6$) δ 148.8, 141.3, 140.7, 135.9, 134.5, 131.6, 127.1, 123.3, 119.9, 118.6, 114.6, 113.7, 108.7, 108.4, 60.9, 52.4, 43.2, 41.7, 35.0, 34.0, 30.5, 28.6.

N-(5-(6,7,7a,8,9,10,11,11a-Octahydro-3H-8,11-methanopyrazolo[4,3-a]phenanthridin-7-yl)-1H-indazol-3-yl)cyclopropanesulfonamide

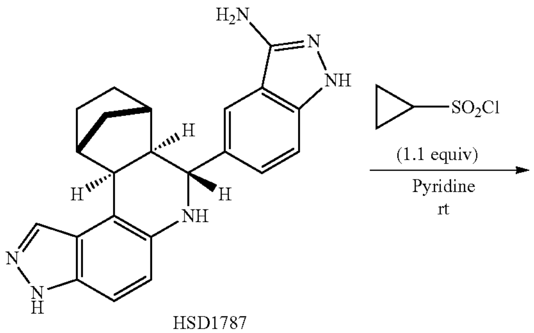

HSD1787

-continued

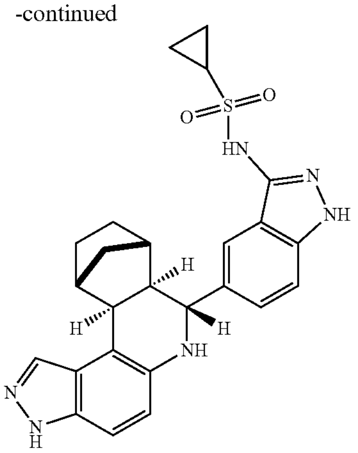

HSD1898

Off-white solid (Starting from 0.3 mmol Substrate 1787) (120 mg, 84%). $^{1}H$ NMR (500 MHz, DMSO-$d_6$) δ 10.00 (s, 1H), 8.39 (s, 1H), 7.75 (d, J=4.6 Hz, 1H), 7.44 (s, 2H), 7.35 (d, J=9.2 Hz, 1H), 7.03 (d, J=9.3 Hz, 1H), 5.85 (s, 1H), 3.93 (d, J=8.5 Hz, 1H), 3.29-3.20 (m, 1H), 2.79 (d, J=8.5 Hz, 1H), 2.77-2.70 (m, 2H), 2.12-2.03 (m, 3H), 1.74 (d, J=9.9 Hz, 1H), 1.62 (tt, J=12.5, 4.4 Hz, 1H), 1.57-1.47 (m, 2H), 1.38-1.33 (m, 2H), 1.26-1.19 (m, 2H), 1.08-1.01 (m, 2H).

1-Methyl-5-(6,7,7a,8,9,10,11,11a-octahydro-3H-8,11-methanopyrazolo[4,3-a]phenanthridin-7-yl)-1H-indazol-3-amine

HSD1902

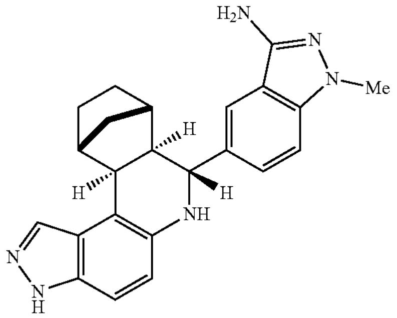

Prepared by using compound Compound 10 as substrate and methylhydrazine as reagent. Method B. Off-white solid (93 mg, 80%). $^{1}H$ NMR (500 MHz, DMSO-$d_6$) δ 7.87 (s, 1H), 7.75 (s, 1H), 7.36 (dd, J=8.7, 1.6 Hz, 1H), 7.26 (d, J=8.6 Hz, 1H), 7.10 (d, J=8.7 Hz, 1H), 6.84 (d, J=8.7 Hz, 1H), 5.38 (s, 2H), 5.29 (s, 1H), 3.74 (d, J=9.6 Hz, 1H), 3.69 (s, 3H), 2.90-2.82 (m, 3H), 2.10 (t, J=9.0 Hz, 1H), 2.02 (d, J=4.3 Hz, 1H), 1.71 (d, J=9.9 Hz, 1H), 1.66-1.58 (m, 1H), 1.54-1.45 (m, 2H), 1.19-1.08 (m, 1H), 1.06-1.00 (m, 1H); $^{13}C$ NMR (126 MHz, DMSO-$d_6$) δ 148.8, 141.3, 140.7, 135.9, 134.5, 131.6, 127.1, 123.3, 119.9, 118.6, 114.6, 113.7, 108.7, 108.4, 60.9, 52.4, 43.2, 41.7, 35.0, 34.0, 30.5, 28.6.

tert-Butyl 4-(3-amino-1H-indazol-5-yl)-3,3a,4,5,8,10c-hexahydropyrazolo[4,3-f]pyrrolo[3,2-c]quinoline-1(2H)-carboxylate

HSD2038

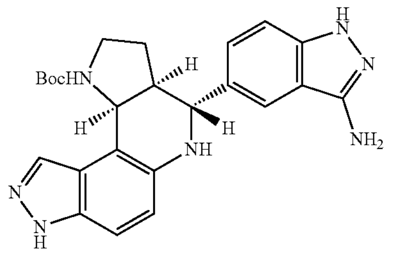

Prepared by using compound HSD2015 (0.10 mmol) as substrate. Method B white solid (28 mg, 63%)$^1$H NMR (500 MHz, DMSO-$d_6$) δ 8.06-7.88 (m, 3H), 7.56 (t, J=9.0 Hz, 1H), 7.24 (d, J=8.8 Hz, 1H), 6.84 (d, J=8.8 Hz, 1H), 5.91 (s, 1H), 5.52 (d, J=7.1 Hz, 1H), 4.71 (s, 1H), 3.53-3.35 (m, 2H), 2.97 (d, J=10.8 Hz, 1H), 2.62 (s, 1H), 1.99-1.85 (m, 1H), 1.55-1.44 (m, 10H), 1.40-1.31 (m, 1H).

2-Fluoro-5-(1-oxo-2,3,6,7,7a,8,9,10,11,11a-decahydro-1H-8,11-methanopyrrolo[3,4-a]phenanthridin-7-yl)benzonitrile

HSD1949

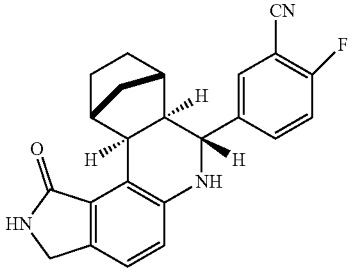

Method A Off white solid (131 mg, 35%)$^1$H NMR (500 MHz, DMSO-$d_6$) δ 8.18 (s, 1H), 7.79 (dd, J=6.5, 2.3 Hz, 1H), 7.65-7.58 (m, 1H), 7.42-7.33 (m, 1H), 7.02 (d, J=7.9 Hz, 1H), 6.78 (dd, J=8.0, 1.2 Hz, 1H), 6.04 (s, 1H), 4.28 (s, 1H), 4.18-4.06 (m, 2H), 3.49 (d, J=8.8 Hz, 1H), 2.29 (s, 1H), 2.20-2.14 (m, 2H), 1.62 (d, J=9.6 Hz, 1H), 1.53-1.40 (m, 4H), 1.38-1.31 (m, 1H), 0.94-0.80 (m, 2H); $^{13}$C NMR (126 MHz, DMSO-$d_6$) δ 171.4, 162.4, (d, J=254.5 Hz), 144.9, 144.0, 134.8, 132.9, 129.5, 125.0, 121.7, 118.9, 116.7, 116.6, 114.6, 99.9, 56.4, 48.2, 47.9, 44.1, 43.7, 34.4, 30.3, 29.4.

7-(3-Amino-1H-indazol-5-yl)-2,3,6,7,7a,8,9,10,11,11a-decahydro-1H-8,11-methanopyrrolo[3,4-a]phenanthridin-1-one

HSD1950

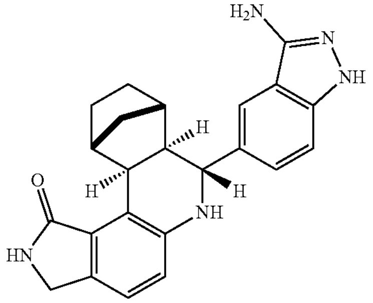

Prepared by using compound HSD1949 as substrate. Method B Pale yellow solid (96 mg, 83%)$^1$H NMR (500 MHz, DMSO-$d_6$) δ 11.24 (s, 1H), 8.15 (s, 1H), 7.64 (s, 1H), 7.24-7.15 (m, 1H), 7.11 (d, J=8.6 Hz, 1H), 6.99 (d, J=8.0 Hz, 1H), 6.80 (d, J=8.0 Hz, 1H), 5.79 (s, 1H), 5.24 (s, 2H), 4.17-4.01 (m, 3H), 3.39 (d, J=8.8 Hz, 1H), 2.46 (d, J=3.1 Hz, 2H), 2.18-2.09 (m, 2H), 1.65 (d, J=9.6 Hz, 1H), 1.56-1.43 (m, 3H), 1.27-1.19 (m, 1H), 0.92 (d, J=9.6 Hz, 1H); $^{13}$C NMR (126 MHz, DMSO-$d_6$) δ 171.6, 149.5, 146.0, 141.2, 135.3, 134.5, 129.8, 126.4, 124.3, 121.3, 119.0, 114.2, 109.5, 58.6, 49.4, 47.2, 44.1, 42.5, 33.9, 30.3, 29.6.

5-(3-Amino-1H-indazol-5-yl)-1,2,3,4,4a,5,6,8,9,11b-decahydro-10H-1,4-methanopyrrolo[3,4-b]phenanthridin-10-one

HSD1910

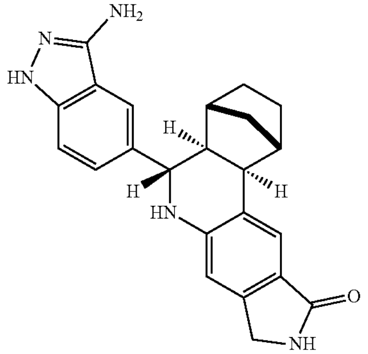

Prepared by using compound HSD1909 as substrate. Method B White solid (102 mg, 88%). $^1$H NMR (500 MHz, DMSO-$d_6$) δ 11.33 (s, 1H), 8.04-7.94 (m, 2H), 7.75 (s, 1H), 7.49-7.41 (m, 2H), 7.34-7.29 (m, 1H), 7.25-7.19 (m, 1H), 6.85-6.78 (m, 1H), 6.02 (s, 1H), 5.32 (s, 2H), 4.16 (s, 2H), 3.59-3.50 (m, 1H), 2.71-2.61 (m, 2H), 2.15-2.05 (m, 1H), 2.02-1.94 (m, 1H), 1.66-1.54 (m, 2H), 1.49-1.37 (m, 2H), 1.15-1.00 (m, 3H); $^{13}$C NMR (126 MHz, DMSO-$d_6$) δ 171.3, 151.9, 149.6, 143.0, 141.6, 133.6, 126.8, 126.1, 122.8, 122.6, 119.8, 114.3, 109.7, 109.4, 60.5, 53.7, 44.8, 43.9, 43.0, 33.9, 29.7, 29.1.

2-Fluoro-5-(2-oxo-2,3,6,7,7a,8,9,10,11,11a-decahydro-1H-8,11-methanopyrrolo[3,2-a]phenanthridin-7-yl)benzonitrile

HSD1929

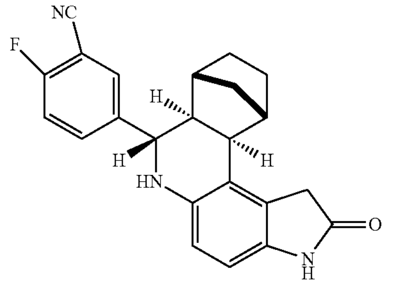

Method A Brown solid (179 mg, 48%). $^1$H NMR (500 MHz, DMSO-d$_6$) δ 10.00 (s, 1H), 7.96 (dd, J=6.4, 2.3 Hz, 1H), 7.83 (ddd, J=8.2, 5.4, 2.3 Hz, 1H), 7.50 (t, J=9.0 Hz, 1H), 6.59 (d, J=10.2 Hz, 2H), 5.29 (s, 1H), 3.56 (d, J=9.7 Hz, 1H), 3.29 (s, 3H), 2.56 (d, J=8.9 Hz, 1H), 1.99 (t, J=9.3 Hz, 1H), 1.95-1.89 (m, 1H), 1.61-1.52 (m, 2H), 1.48-1.41 (m, 1H), 1.38-1.32 (m, 1H), 1.24-1.20 (m, 1H), 1.13-1.07 (m, 1H), 1.01 (d, J=9.9 Hz, 1H); $^{13}$C NMR (126 MHz, DMSO-d$_6$) δ 176.5, 163.0 (d, J=255.7 Hz), 142.9, 142.5, 136.1, 135.9, 133.5, 125.1, 124.1, 116.9, 114.5, 112.8, 108.7, 100.2 (d, J=15.0 Hz), 59.5, 52.9, 44.2, 42.9, 36.2, 34.0, 29.6, 29.1.

7-(3-Amino-1H-indazol-5-yl)-1,3,6,7,7a,8,9,10,11,11a-decahydro-2H-8,11-methanopyrrolo[3,2-a]phenanthridin-2-one

HSD1930

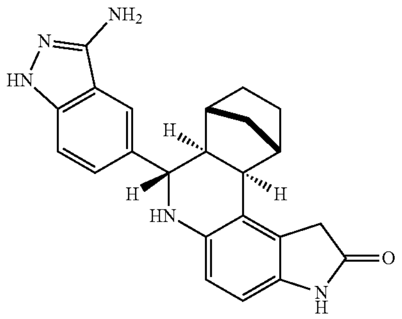

Prepared by using compound HSD1929 as substrate. Method B Off-white solid (95 mg, 82%). $^1$H NMR (500 MHz, DMSO-d$_6$) δ 11.29 (s, 1H), 9.98 (s, 1H), 7.73 (d, J=2.5 Hz, 1H), 7.34-7.23 (m, 1H), 7.25-7.12 (m, 1H), 6.66-6.57 (m, 2H), 5.30 (s, 2H), 5.10 (s, 1H), 3.42 (dd, J=10.2, 2.6 Hz, 1H), 2.58-2.45 (m, 3H), 2.04 (td, J=10.6, 5.3 Hz, 1H), 1.96 (s, 1H), 1.63-1.54 (m, 2H), 1.47-1.37 (m, 1H), 1.37-1.34 (m, 1H), 1.09-0.98 (m, 2H); $^{13}$C NMR (126 MHz, DMSO-d$_6$) δ 176.5, 149.6, 143.5, 141.6, 135.7, 134.1, 126.9, 125.1, 123.9, 119.7, 114.3, 112.8, 109.5, 108.6, 61.7, 54.0, 44.3, 42.4, 36.2, 33.9, 29.7, 29.1.

5-(3-Amino-1H-indazol-5-yl)-1,2,3,4,4a,5,6,11b-octahydro-8H-1,4-methanopyrrolo[3,4-b]phenanthridine-8,10(9H)-dione

HSD1943

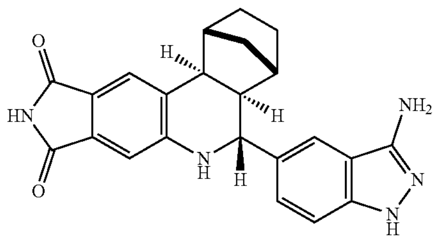

Prepared by using compound HSD1944 as substrate. Method B Off white solid (110 mg, 92%)$^1$H NMR (500 MHz, DMSO-d$_6$) δ 11.29 (s, 1H), 10.13 (s, 1H), 10.07 (s, 1H), 7.73 (s, 1H), 7.34-7.28 (m, 1H), 7.19 (d, J=8.5 Hz, 1H), 6.71 (s, 1H), 6.41 (s, 1H), 5.30 (s, 2H), 5.12 (s, 1H), 3.42 (d, J=10.4 Hz, 1H), 2.58-2.52 (m, 2H), 2.03 (t, J=9.6 Hz, 1H), 1.95 (d, J=4.2 Hz, 1H), 1.64-1.55 (m, 2H), 1.47-1.37 (m, 1H), 1.37-1.33 (m, 1H), 1.08-0.99 (m, 2H); $^{13}$C NMR (126 MHz, DMSO-d$_6$) δ 156.1, 149.6, 143.2, 141.6, 134.3, 128.5, 126.9, 122.9, 119.7, 118.9, 114.3, 109.5, 107.9, 96.6, 61.8, 54.2, 44.2, 42.5, 39.2, 33.9, 29.7, 29.2.

6-Fluoro-1-methyl-5-(6,7,7a,8,9,10,11,11a-octahydro-3H-8,11-methanopyrazolo[4,3-a]phenanthridin-7-yl)-1H-indazol-3-amine

HSD1945

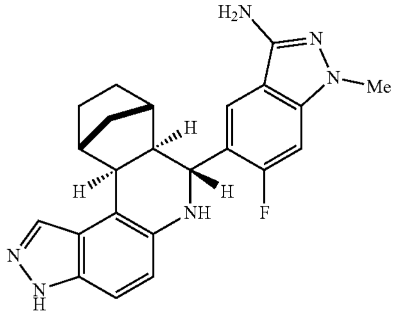

Prepared by using compound S-10 (0.3 mmol) as substrate and methylhydrazine as reagent. Method B Off-white solid (93 mg, 77%). $^1$H NMR (500 MHz, DMSO-d$_6$) δ 7.97-7.83 (m, 2H), 7.16 (d, J=11.4 Hz, 1H), 7.11 (d, J=8.7 Hz, 1H), 6.83 (d, J=8.7 Hz, 1H), 5.48 (s, 2H), 5.28 (s, 1H), 4.06 (d, J=9.4 Hz, 1H), 3.66 (s, 3H), 2.88 (dd, J=15.3, 6.2 Hz, 2H), 2.14 (t, J=9.0 Hz, 1H), 1.99 (d, J=4.2 Hz, 1H), 1.72-1.59 (m, 2H), 1.52 (pd, J=8.4, 8.0, 3.7 Hz, 2H), 1.16 (tt, J=12.8, 10.0, 4.0 Hz, 1H), 1.05 (dd, J=8.6, 6.5 Hz, 1H); $^{13}$C NMR (126 MHz, DMSO-d$_6$) δ 161.7 (d, J=243.1 Hz), 149.1, 140.8, 140.6, 136.05, 131.6, 123.2, 123.0, 121.5, 118.6, 113.8, 112.1, 108.4, 94.4, 53.0, 52.5, 43.3, 41.8, 35.1, 34.1, 30.5, 28.6.

5-(9,10-Dihydroxy-6,7,7a,8,9,10,11,11a-octahydro-3H-8,11-methanopyrazolo[4,3-a]phenanthridin-7-yl)-2-fluorobenzonitrile

HSD2024

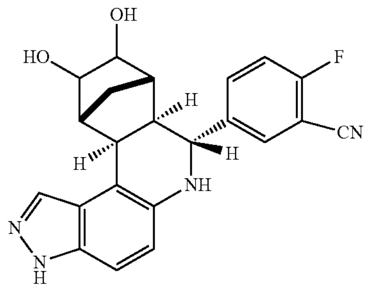

Prepared by using compound HSD1831 (100 mg, 0.28 mmol) as substrate. Substrate 10 (100 mg, 0.28 mmol) was dissolved in acetone/$H_2O$ (3:1) followed by addition of N-methyl morpholineoxide in water (2 equiv.) and a solution of $OsO_4$ in t-BuOH (23 μL, 2.5% wt.) cautiously. Reaction mixture was stirred for 12 h at room temperature. After completion, aqueous saturated $Na_2SO_3$ (3 mL) was added and stirred for 15 minutes. Reaction mixture extracted with ethyl acetate (25 mL) and water (10 mL), again water layer extracted with ethyl acetate (10 mL). Combined organic layer dried and purified by silica gel chromatography to get the desired compound HSD 2024 as gray solid (42 mg, 81%). $^1$H NMR (500 MHz, DMSO-$d_6$) δ 7.95 (dd, J=6.3, 2.3 Hz, 1H), 7.88-7.83 (m, 1H), 7.80 (ddd, J=8.8, 5.3, 2.3 Hz, 1H), 7.48 (t, J=9.0 Hz, 1H), 7.14 (d, J=8.7 Hz, 1H), 6.80 (d, J=8.8 Hz, 1H), 5.57 (s, 1H), 4.86-4.76 (m, 1H), 4.57 (d, J=5.0 Hz, 1H), 3.92-3.84 (m, 2H), 3.64-3.54 (m, 1H), 2.71 (d, J=8.6 Hz, 1H), 2.60-2.51 (m, 1H), 1.96-1.93 (m, 1H), 1.83-1.74 (m, 1H), 1.54 (d, J=10.3 Hz, 1H), 1.47 (d, J=10.4 Hz, 1H); $^{13}$C NMR (126 MHz, DMSO-$d_6$) δ 162.9 (d, J=255.7 Hz), 143.0, 139.9, 136.0, 135.8, 133.5, 131.3, 123.0, 118.4, 116.9, 114.6, 113.2, 108.8, 100.1, 73.8, 73.3, 58.1, 49.4, 47.2, 46.1, 37.6, 28.1.

2-Fluoro-5-(6,7,7a,8,9,10,11,11a-octahydro-8,11-methanothiazolo[4,5-a]phenanthridin-7-yl)benzonitrile

HSD2041

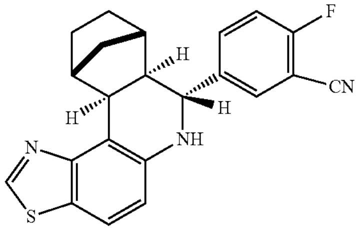

Method A Off-white solid (111 mg, 30%). $^1$H NMR (500 MHz, DMSO-$d_6$) δ 9.21 (s, 1H), 7.92 (dd, J=6.3, 2.3 Hz, 1H), 7.76 (ddd, J=8.1, 5.5, 2.3 Hz, 1H), 7.64 (d, J=8.5 Hz, 1H), 7.44 (t, J=9.1 Hz, 1H), 6.86 (d, J=8.5 Hz, 1H), 6.00 (s, 1H), 4.08 (d, J=6.5 Hz, 1H), 3.15 (d, J=8.7 Hz, 1H), 3.01-2.91 (m, 1H), 2.17 (t, J=7.6 Hz, 1H), 2.11-2.07 (m, 1H), 1.68-1.54 (m, 2H), 1.53-1.43 (m, 2H), 1.30-1.22 (m, 1H), 0.99-0.92 (m, 1H); $^{13}$C NMR (126 MHz, DMSO-$d_6$) δ 162.8 (d, J=254.5 Hz), 154.9, 153.0, 144.8, 143.4, 136.4, 135.5, 133.3, 123.3, 120.0, 119.0, 116.9, 115.9, 114.6, 100.1 (d, J=16.38 Hz), 57.4, 50.0, 43.9, 41.9, 41.4, 34.2, 30.0, 29.4.

2-Fluoro-5-(6,7,7a,8,9,10,11,11a-octahydro-3H-8,11-methanopyrrolo[3,2-a]phenanthridin-7-yl)benzonitrile

HSD2030

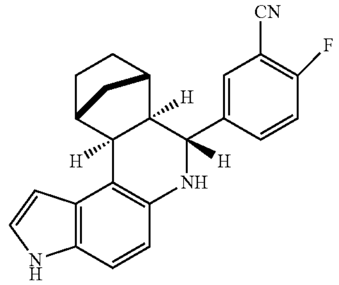

Method A White solid (84 mg, 24%). $^1$H NMR (500 MHz, Methanol-$d_4$) δ 8.22 (dd, J=6.3, 2.4 Hz, 1H), 8.16 (ddd, J=8.9, 5.2, 2.4 Hz, 1H), 7.36 (t, J=8.9 Hz, 1H), 7.26-7.24 (m, 1H), 7.21 (d, J=8.4 Hz, 1H), 7.15-7.14 (m, 1H), 6.42 (d, J=2.9 Hz, 1H), 3.43 (d, J=10.5 Hz, 1H), 3.20 (d, J=10.9 Hz, 1H), 2.95 (d, J=8.4 Hz, 1H), 2.69 (s, 1H), 2.28 (s, 1H), 1.70-1.65 (m, 2H), 1.64-1.58 (m, 1H), 1.34 (d, J=10.0 Hz, 1H), 1.11-1.05 (m, 1H).

5-(6,7,7a,8,9,10,11,11a-Octahydro-3H-8,11-methanopyrrolo[3,2-a]phenanthridin-7-yl)-1H-indazol-3-amine

HSD4017

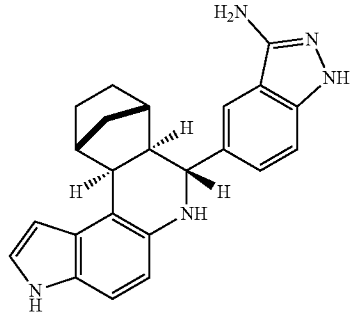

Prepared by using compound HSD2030 (0.14 mmol) as substrate. Method B Pale yellow solid (42 mg, 81%). $^1$H NMR (500 MHz, Methanol-$d_4$) δ 7.70 (s, 1H), 7.44 (dd, J=8.7, 1.6 Hz, 1H), 7.26 (dd, J=8.6, 0.8 Hz, 1H), 7.14 (d, J=3.1 Hz, 1H), 7.05 (d, J=8.4 Hz, 1H), 6.57 (d, J=8.4 Hz, 1H), 6.44 (dd, J=3.2, 0.9 Hz, 1H), 3.89 (d, J=10.1 Hz, 1H), 3.11 (d, J=3.9 Hz, 1H), 2.97 (d, J=8.7 Hz, 1H), 2.29 (t, J=9.3 Hz, 1H), 2.04 (d, J=3.7 Hz, 1H), 1.82-1.76 (m, 1H), 1.71-1.64 (m, 1H), 1.60-1.53 (m, 2H), 1.26-1.19 (m, 1H), 1.09-1.03 (m, 1H); $^{13}$C NMR (126 MHz, Methanol-$d_4$) δ 149.0, 141.8, 138.1, 134.9, 131.9, 127.5, 127.4, 123.6, 118.8, 116.6, 113.7, 112.1, 109.3, 109.2, 99.9, 61.9, 51.8, 43.5, 41.2, 39.2, 33.2, 30.1, 28.2.

7-(3-(Trifluoromethyl)-1H-pyrazol-4-yl)-6,7,7a,8,9,10,11,11a-octahydro-3H-8,11-methanobenzo[c]pyrazolo[4,3-f][1,7]naphthyridine

HSD4009

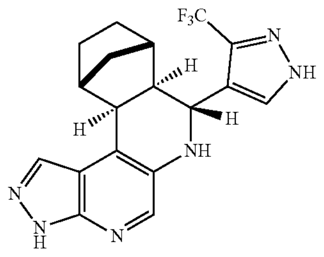

Method A Off white solid (65%)$^1$H NMR (500 MHz, DMSO-$d_6$) δ 7.90 (s, 1H), 7.34 (s, 1H), 5.38 (s, 1H), 4.38 (s, 1H), 3.34-3.31 (m, 1H), 2.55 (s, 3H), 2.35 (d, J=4.0 Hz, 1H), 2.23-2.10 (m, 2H), 1.69 (d, J=9.6 Hz, 1H), 1.64-1.58 (m, 1H), 1.57-1.48 (m, 2H), 1.38-1.27 (m, 1H), 0.97 (d, J=9.6 Hz, 1H); $^{13}$C NMR (126 MHz, DMSO) δ 149.26, 140.38, 139.00, 137.71 (q, J=35.2 Hz), 135.54, 128.92, 127.28, 124.35, 121.86 (q, J=269.6 Hz), 112.47, 49.99, 48.84, 47.67, 43.63, 34.66, 30.58, 28.89, 15.42.

Ethyl-6,7,7a,8,9,10,11,11a-octahydro-3H-8,11-methanopyrazolo[4,3-a]phenanthridine-7-carboxylate

HSD4011

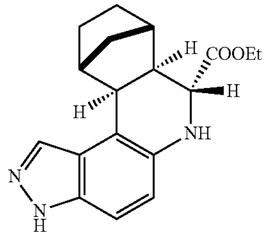

Method A Off white solid (61%) $^1$H NMR (500 MHz, DMSO-$d_6$) δ 8.13 (s, 1H), 7.34 (d, J=8.6 Hz, 1H), 7.29 (d, J=8.6 Hz, 1H), 4.26 (qd, J=7.1, 1.3 Hz, 2H), 3.50 (d, J=11.3 Hz, 1H), 3.12 (d, J=11.3 Hz, 1H), 2.49 (q, J=1.8 Hz, 1H), 2.43 (d, J=3.8 Hz, 1H), 1.81-1.45 (m, 5H), 1.28 (t, J=7.1 Hz, 3H), 1.18-1.06 (m, 2H); $^{13}$C NMR (126 MHz, DMSO) δ 165.53, 156.77, 140.96, 134.27, 133.95, 128.76, 122.06, 121.49, 109.22, 61.48, 46.91, 45.21, 43.03, 41.56, 40.89, 35.33, 29.62, 14.58.

2-Fluoro-5-(9-oxo-1,2,3,4,4a,5,6,8,9,10,11,12b-dodecahydro-1,4-methanopyrido[3,2-b]phenanthridin-5-yl)benzonitrile

HSD1951

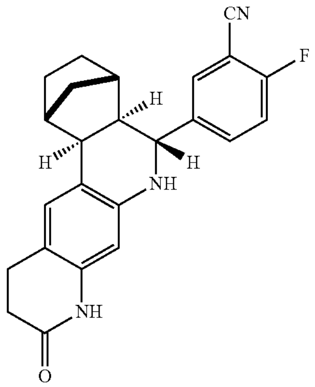

Method A Off white solid (80%)$^1$H NMR (500 MHz, DMSO-$d_6$) δ 9.84 (s, 1H), 7.93 (dd, J=6.3, 2.3 Hz, 1H), 7.80 (ddd, J=8.8, 5.4, 2.3 Hz, 1H), 7.49 (t, J=9.0 Hz, 1H), 6.94 (s, 1H), 6.21 (s, 1H), 5.57 (s, 1H), 3.60 (d, J=9.3 Hz, 1H), 2.71 (t, J=7.4 Hz, 2H), 2.54-2.46 (m, 2H), 2.39-2.31 (m, 2H), 2.02-1.90 (m, 2H), 1.61-1.52 (m, 2H), 1.48-1.29 (m, 1H), 1.37-1.26 (m, 1H), 1.12-1.05 (m, 1H), 1.02-0.94 (m, 1H); $^{13}$C NMR (126 MHz, DMSO) δ 170.79, 163.03 (d, J=255.7 Hz), 146.56, 142.98, 136.59, 135.87, 135.81, 133.54, 127.65, 120.16, 116.90, 116.74, 114.62, 113.90, 102.39, 100.15, 100.03, 58.96, 52.67, 43.43, 43.06, 34.06, 31.64, 29.62, 29.19, 24.87.

5-(3-Amino-1H-indazol-5-yl)-2,3,4,4a,5,6,8,10,11,12b-decahydro-1,4-methanopyrido[3,2-b]phenanthridin-9(1H)-one

HSD1952

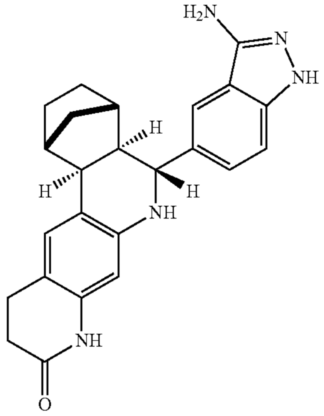

Prepared by using compound HSD1951 as substrate. Method B Off white solid (92%)$^1$H NMR (500 MHz, DMSO-$d_6$) δ 11.29 (s, 1H), 9.82 (s, 1H), 7.71 (d, J=1.6 Hz, 1H), 7.29 (dd, J=8.6, 1.6 Hz, 1H), 7.19 (d, J=8.6 Hz, 1H), 6.96 (s, 1H), 6.26 (s, 1H), 5.36 (s, 1H), 5.30 (s, 2H), 3.46 (d, J=10.1 Hz, 1H), 2.72 (t, J=7.5 Hz, 2H), 2.58 (d, J=4.2 Hz, 1H), 2.54-2.46 (m, 2H), 2.41-2.31 (m, 2H), 2.03 (t, J=9.5

Hz, 1H), 1.97 (d, J=4.2 Hz, 1H), 1.58 (dq, J=11.7, 7.3, 5.9 Hz, 2H), 1.47-1.28 (m, 2H), 1.08-0.97 (m, 2H); $^{13}C$ NMR (126 MHz, DMSO) δ 170.83, 149.63, 147.55, 141.63, 136.45, 134.20, 127.50, 126.92, 120.18, 119.72, 114.37, 113.48, 109.56, 102.45, 61.14, 53.86, 43.64, 42.50, 33.93, 31.73, 29.80, 29.17, 24.93.

Those skilled in the art will recognize that numerous modifications can be made to the specific implementations described above. The implementations should not be limited to the particular limitations described. Other implementations may be possible.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

It is intended that that the scope of the present methods and compositions be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims.

REFERENCES CITED

1. L. Weber, *Curr. Med. Chem.* 2002, 9, 2085-2093.
2. C. Hulme, I. Akritopoulou-Zanze, W. M Dai, B. Beck, S. Srivastava, W. Wang, K. Wang, A. Czarna, T. A. Holak, L. Meireles, C. Camacho, *Springer*, New York, NY. 2009, 75-106.
3. P. Slobbe, E. Ruijiter, R. V. Orru, *Med. Chem. Comm.* 2012, 3, 1189-1218.
4. M. Pedrola, M. Jorba, E. Jardas, F. Jardi, O. Ghashghaei, M. Viñas, R. Lavilla, *Front. Chem.* 2019, 7, 475.
5. D. Insuasty, J. Castillo, D). Becerra, H. Rojas, R. Abonia, *Molecules.* 2020, 25, p. 505.
6. a) L Ugi, R. Meyr, U. Fetzer, C. Steinbruckner, *Angew. Chem.* 1959, 71, 386. b) 1. Ugi, C. Steinbrückner, *Angew. Chem.* 1960, 72, 267-268. c) I. Ugi, F. K. Rosendahl, F. Bodesheim, *Justus Liebigs Annalen der Chemie,* 1963, 666, 54-61.
7. Z. Puterová, A. Krutošiková, D. Végh, *Arkivoc,* 2010, 1, 209-246.
8. A. Hantzsch, Ber. Dtsch. Chem. Ges. 1881, 14, 1637-1638.
9. P. Biginelli, Ber. Dtsch. Chem. Ges. 1891, 24, 1317-1319 and 2962-2967
10. a) M. Passerini, L. Simone, *Gazz. Chim. Ital,* 1921, 51, 126-129. b) M. Passerini, *Gazz. Chim.* Ital, 1921, 51, 181-189.
11. B. Loev, M. M Goodman, et al., *J. Med. Chem.* 1974, 17, 956-965.
12. a) A. Znabet, M. M. Polak, E. Janssen, F. J. de Kanter, N. J. Turner, R. V. Orru, E. Ruijter, *Chem. Commun.* 2010, 46, 7918-7920. b) K. Rossen, P. J. Pye, L. M. DiMichele, R. P. Volante, P. J. Reider, *Tetrahedron Lett.* 1998. 39, 6823-6826.
13. a) N, Desroy, C. Housserman, et al., *J. Med. Chem.* 2017, 60, 3580-3590. b) A. Joncour, N. Desroy, et al, *J. Med. Chemu.* 2017. 60, 7371-7392.
14. O. Ghashghaei, C. Masdeu, C. Alonso, F. Palacios, R. Lavilla, *Drug Dis. Today: Technol.* 2018, 29, 71-79.
15. J. S. Bello Forero, J. Jones Junior, F. M da Silva, Curr. *Org. Synth.* 2016, 13, 157-175.
16. I. Muthukrishnan, V. Sridharan, J. C. Menéndez, *Chem. Rev.* 2019, 119, 5057-5191.
17. E. S. Priestley, I. De Lucca, et al., *Bioorg. Med. Chem. Lett.* 2013, 23, 2432-2435.
18. P. C. Wong, J. M. Luettgen, A. R. Rendina, C. A. Kettner, B. Xin, R. M. Knabb, R. R. Wexler, E. S. Priestley, *Thromb. Hoemost.* 2010, 104, 261-269.
19. D. A. Powell, R. A. Batey, *Org. let.* 2002, 4, 2913-2916.
20. N. Goli. P. S. Mainkar, S. S. Kotapalli, K. Tejaswini, R. Ummanni. S. Chandrasekhar, *Bioorg. Med. Chem. Lett.* 2017, 27, 1714-1720.
21. L. Carlino. M. S. Christodoulou. V. Restelli, et al., *Chem. Med. Chem.* 2018, 13, 2627-2634.
22. G. A. Thakur, A. R. Kulkarni, J. R. Deschamps, R. L. Papke. 2013, *J. Med. Chew.* 56. 8943-8947.
23. G. Hoffmann, F. Breitenbücher, M. Schuler, A. E. Ehrenhofer-Murray, *J. Biol. Chem.* 2014. 289, 5208-5216.
24. V. Sridharan, P. A. Suryavanshi, J. C. Menendez, *Chem. Rev.* 2011, 111, 7157-7259.
25. US Food and Drug Administration. FDA approves talazoparib for gBRCAm HER2-negative locally advanced or metastatic breast cancer. Oct. 16, 2018. Updated Dec. 17, 2018. www.fda.gov/NewsEvents/Newsroom/PressAnnouncements/ucm6235 40.htm. Accessed Jan. 17, 2019.
26. C. Chen, S. Zingales, T. Wang, M. Yuan, D. Wang, L. Cai. Q. Jiang. *J. Enzyme Inhib. Med. Chem.* 2016. 31, 853-858.
27. J. L. Díaz, U. Christmann, A. Fernandez, Ni. Luengo, M. Bordas, R. Enrech, M. Carro, R. Pascual, J. Burgueno, M. Merlos, J. Benet-Buchholz, *J. Med. Chem.* 2013. 56, 3656-3665.
28. R. Dent, M. Trudeau, K. I. Pritchard, W. M. Hanna, H4.1K. Kahn, C. A. Sawka, L. A. Lickley, E. Rawlinson, P. Sun, S. A. Narod, *Clin. Cancer Res.* 2007, 13, 4429-4434.
29. F. Kassam, K. Enright, R. Dent, G. Dranitsaris, J. Myers, C. Flynn, M. Fralick, R. Kumar, M. Clemons, Clin. Breast *Cancer* 2009, 9, 29-33.
30. C. D. Smith, J. I. Gavrilyuk, A. J Lough, R. A. Batey, J. Or Chem. 2010, 75, 702-715.
31. J. L. Ralbovsky, R. P. Beckett, U.S. patent application Ser. No. 12/040, 2008, 565.
32. H. Mei, J. Han, S. Fustero, M. Medio-Sirnon, D. M. Sedgwick, C. Santi, R. Ruzziconi, V. A. Soloshonok, *Chem. Eur. J.* 2019. 25, 11797-11819.
33. T. Mosmann, J. Imimunol. Methods. 1983, 65, 55-63.
34. H. Mei, J. Han, S. Fustero, M. Medio-Simon, D. M. Sedgwick, C. Santi, R. Ruzziconi, V. A. Soloshonok, *Chem. Eur. J.* 2019, 25, 11797-11819.
35. P. C. Sharma, A. Sinhmar, A. Sharma, H. Rajak, D. P. Pathak, *J. Enzyme Inhib. Med. Chew.* 2013, 28, 240-266.
36. G. J. V. Nossal, Mol. Med. 1996, 2, 165-168.
37. R. J. Young. Green. D. V.; Luscombe, C. N.; Hill, A. P. *Drug Discov. Today* 2011, 16, 822-330.
38. Yang. Y.; Chen, I.; Nilsson, I.; et al, *J. Med. Chem.* 2010, 53, 7709-7714.
39. P. A. Clemons, N. E. Bodycombe, H. A. Carrinski, J. A. Wilson, A. F. Shamji, B. K. Wagner, A. N. Koehler, S. L. Schreiber, *Proc. Natl. Acad. Sci.* 2010, 107, 18787-18792.
40. F. Lovering, J. Bikker, C. Humblet, *J. Med. Chem,* 2009. 52, 6752-6756.
41. K. Schiemann, D. Bruge, H. Buchstaller, D. Finsinger, W. Stachle, C. Amendt, U. Eide, F. Zenke, 2006, WO2006002726A1, January, 12.

42. D. Insuasty, J. Castillo, D. Becerra, H. Rojas, R., Abonia, *Molecules,* 2020, 25, p. 505.

43. N. Dayal, C. Opoku-Temeng, D. E. Hernandez, M. A. Sooreshjani, B. A. Carter-Cooper, R. G. Lapidus, H. O. Sintim. *Future Med. Chem.* 2018, 10, 823-835.

44. C. Opoku-Terneng, N. Dayal, D. E. Hernandez, N. Naganna, H. O. Sintim, *Chem. Commun.* 2018, 54, 4521-4524.

45. Opoku-Teneng, C.; Dayal, N.; Sooreshjani, M. A.; Sintim, H. O. *Bioorg. Chem.* 2018, 78, 418-426.

46. N. Dayal, C. G. Mikek, D. Hernandez, G. A. Naclerio, E. F. Y. Chu, B. A. Carter-Cooper, R. G. Lapidus, H. O. Sintim, *Eur. J. Med. Chem.* 2019, 180, 449-456.

We claim:

1. A compound selected from the group consisting of

HSDC1p

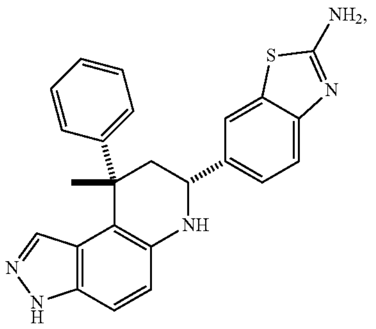

HSDC1q

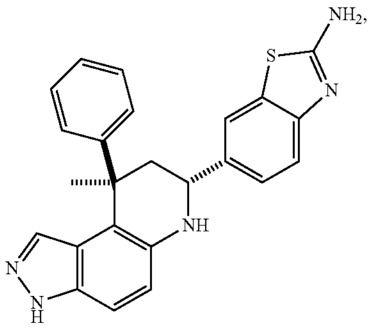

HSDC1r

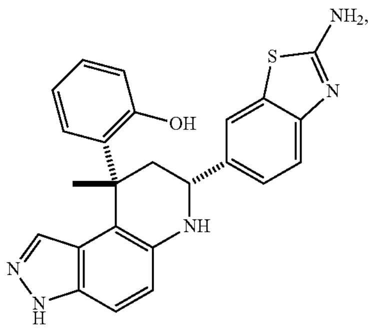

-continued

HSDC1s

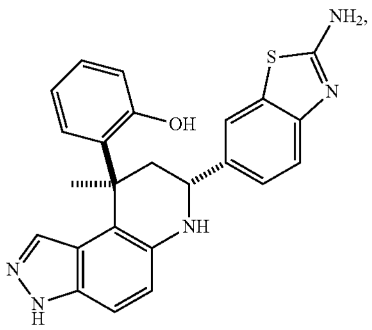

HSDC1t

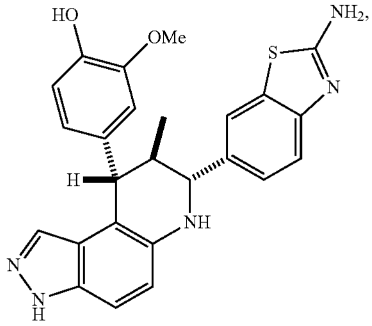

HSDC1u

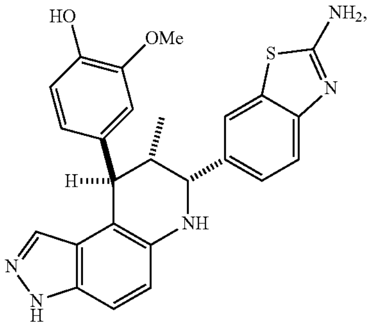

HSDC1v

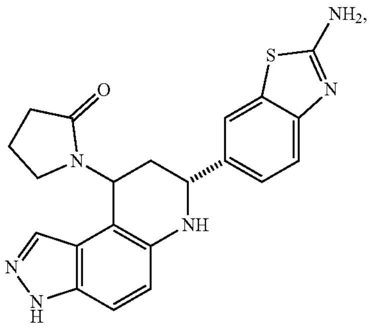

HSDD1

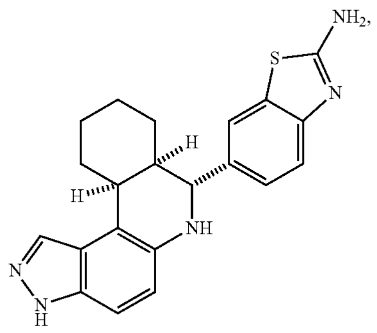

-continued
HSDD2
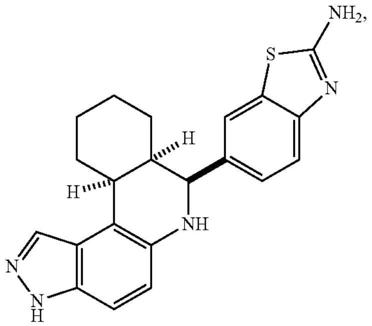
HSDD3
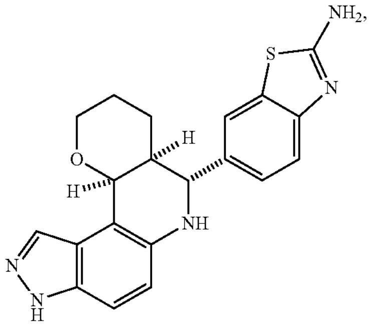
HSDD4
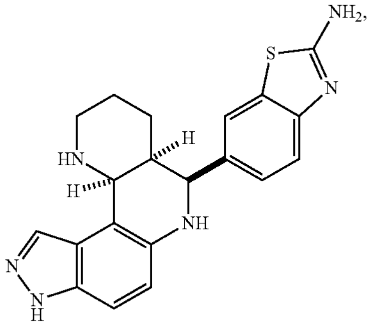
HSDD5
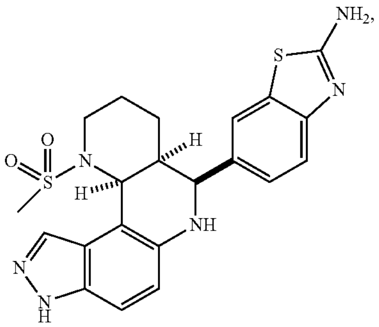
HSDD6
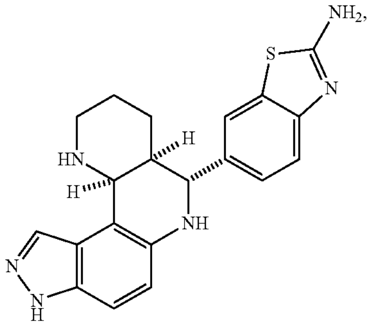
-continued
HSDD7
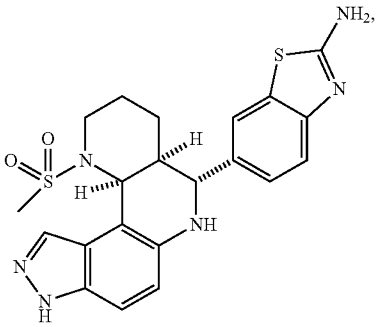
HSDD8
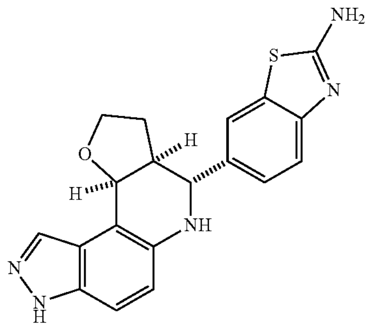
and
HSDD9
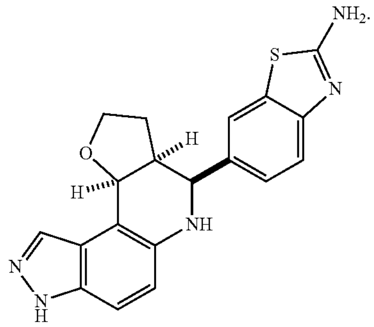
2. A compound selected from the group consisting of
1
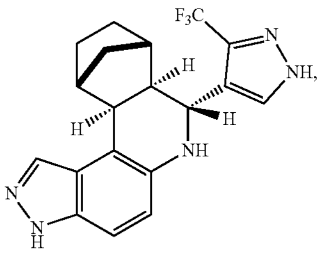
2
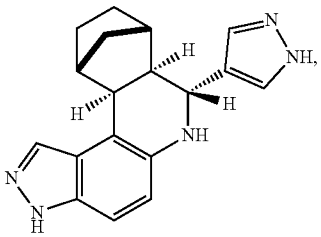

-continued
3
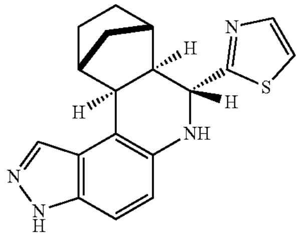
,
4
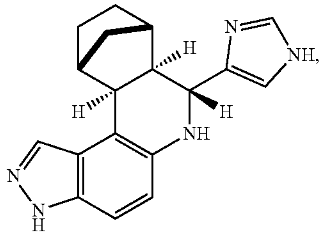
5
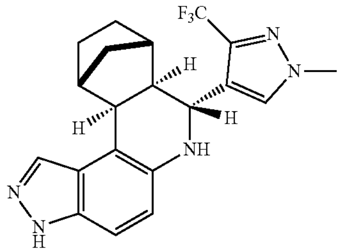
,
6
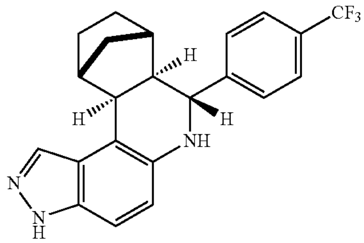
7
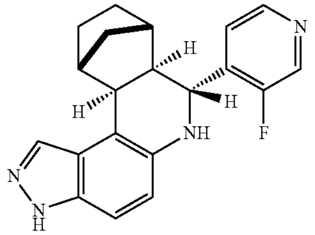
,
8
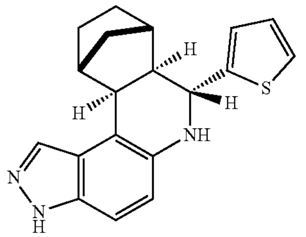
,
-continued
HSDF1
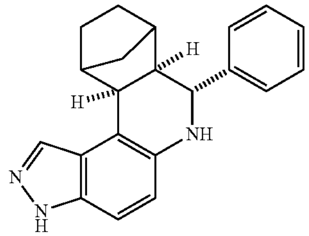
,
HSDF2
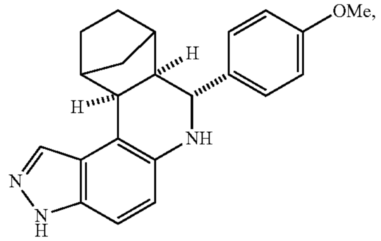
HSDF3
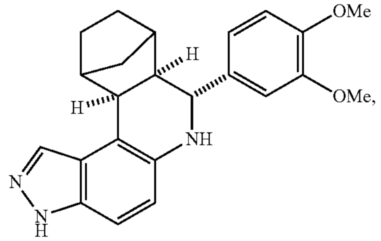
HSDF4
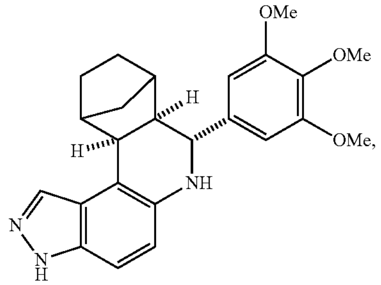
9
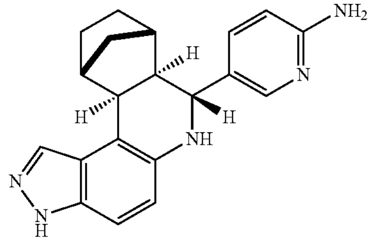
,
10
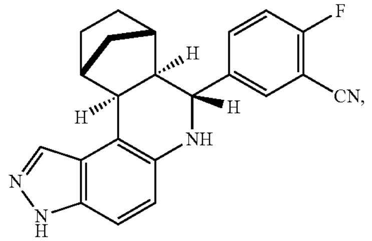

-continued
11
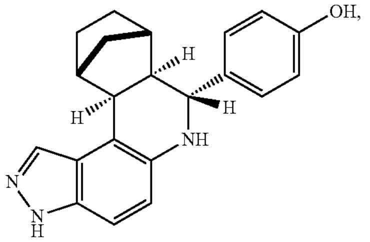
12
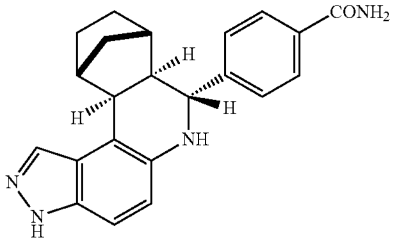
,
13
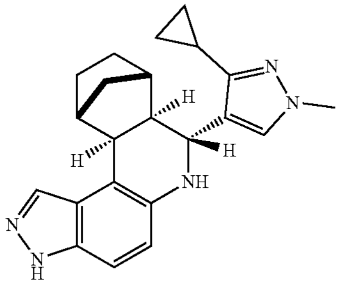
,
14
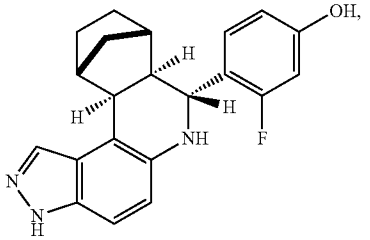
15
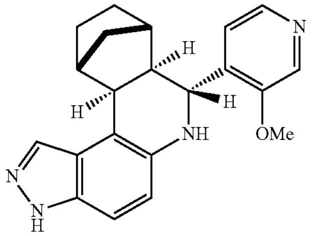
,
HSD1845
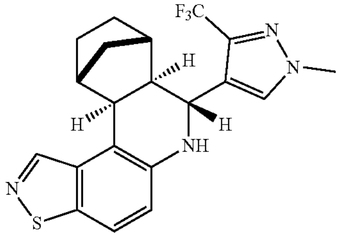
,
-continued
HSD4029
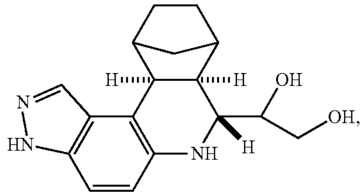
HSD4030
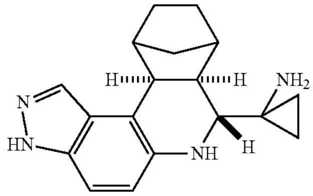
,
HSD4031
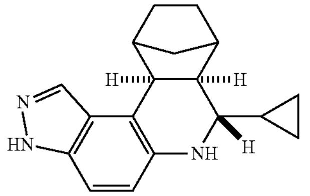
,
HSD4032
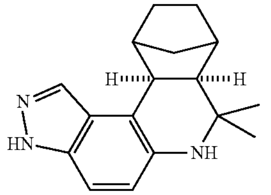
,
HSD1817
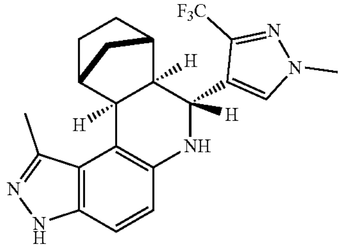
,
HSD4011
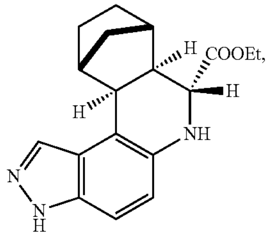
and
HSDF5
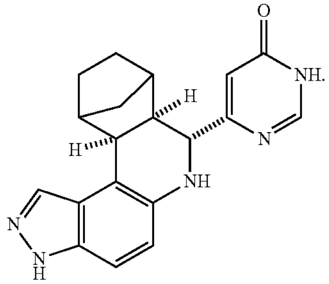

3. A compound selected from the group consisting of
HSD1901b
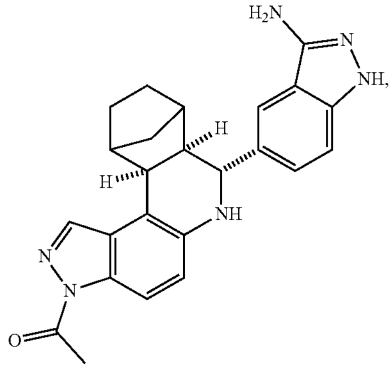
HSD1901c
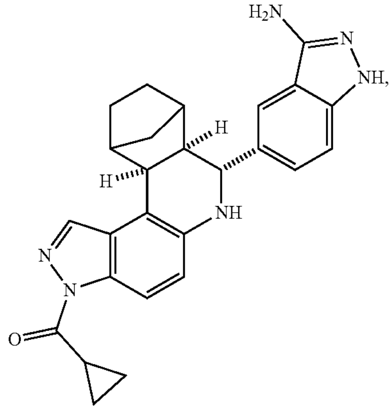
HSD1901d
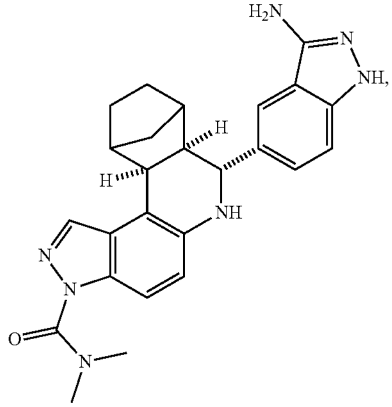
HSD1901e
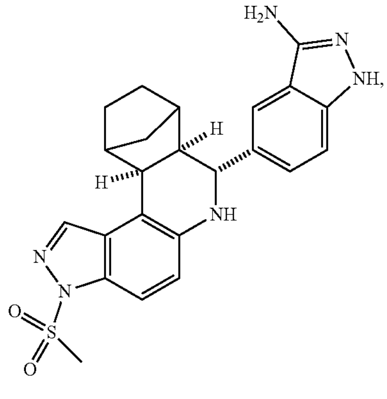
-continued
HSD1901f
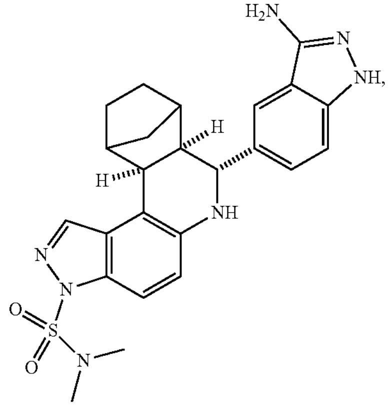
HSD1901g
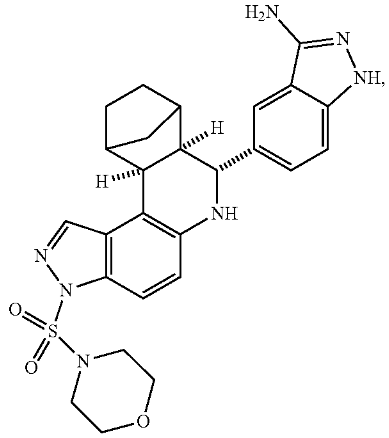
HSD1901h
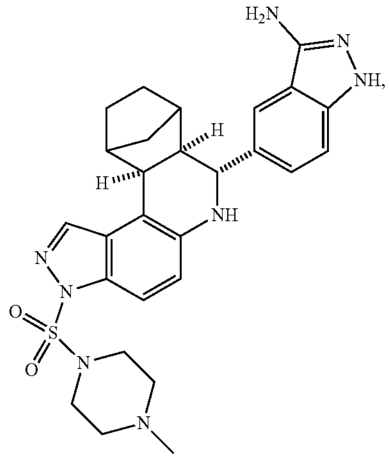
HSD1901i
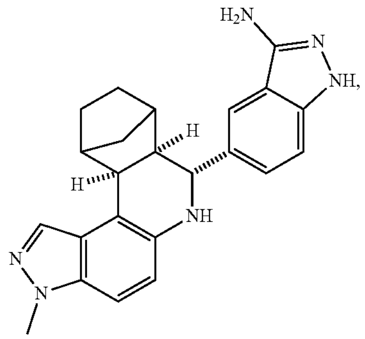

-continued
HSD1901j
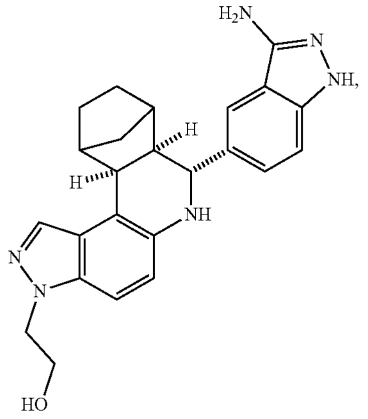
HSD1901k
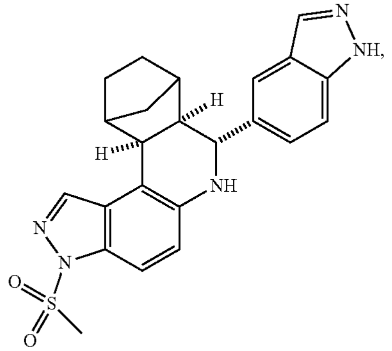
HSD5005b
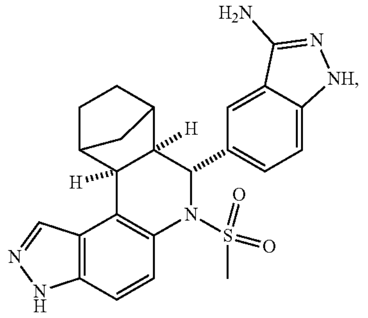
HSD5005c
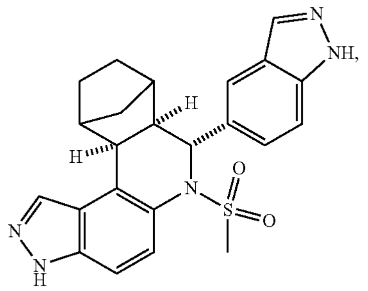
-continued
HSD5005d
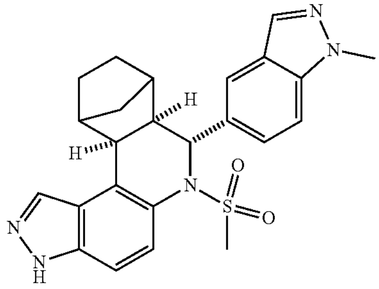
HSD5005e
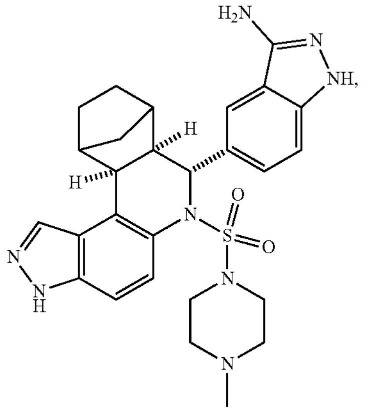
HSD5005f
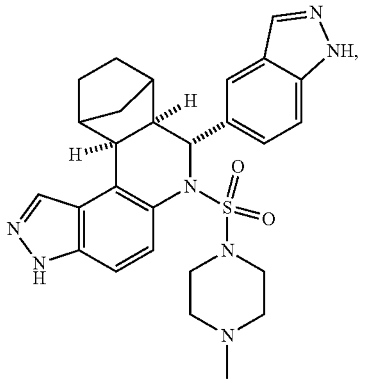
HSD5005g
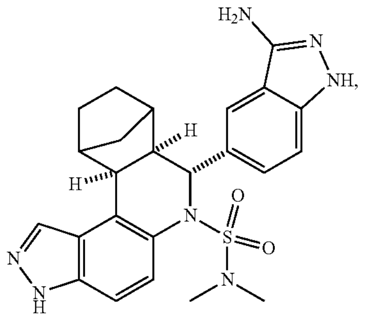

-continued
HSD5005h
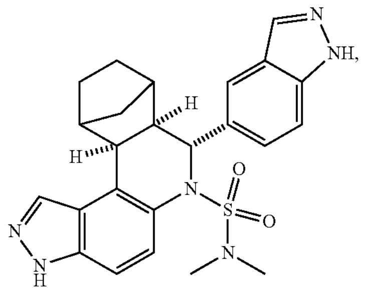
HSD5005i
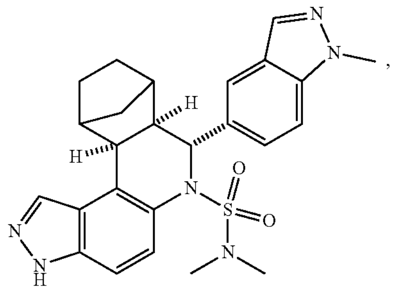
HSD5005j
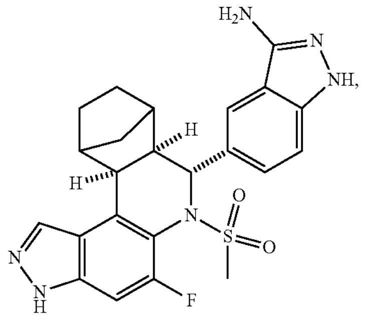
HSD5005k
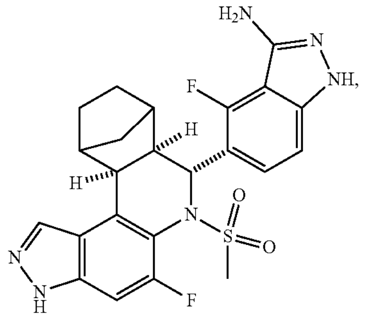
HSD5005l
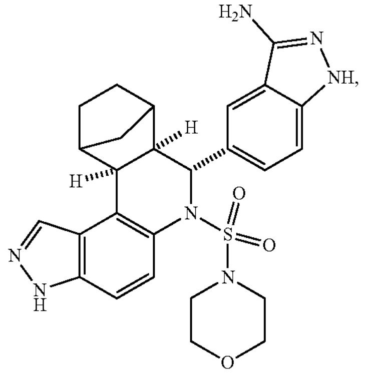
-continued
HSD5005m
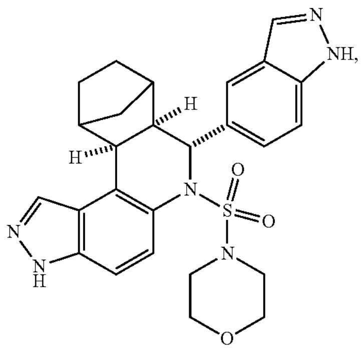
HSD5005n
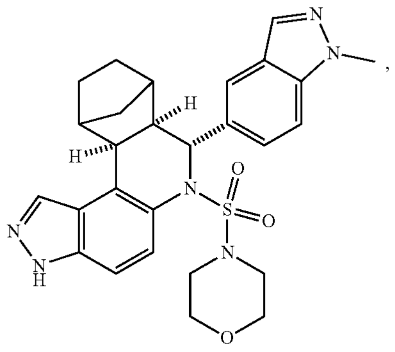
HSD5005o
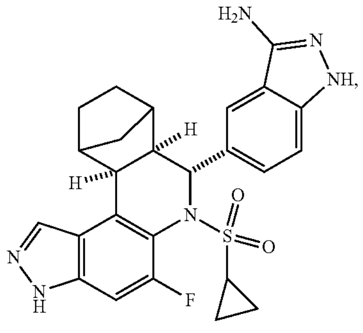
HSD5005p
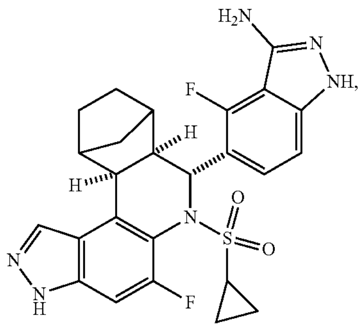

-continued
HSD1832
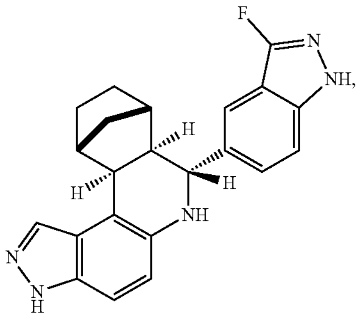
HSD1897
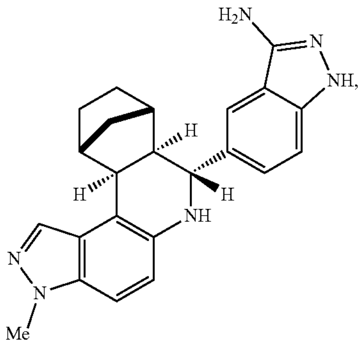
HSD5000
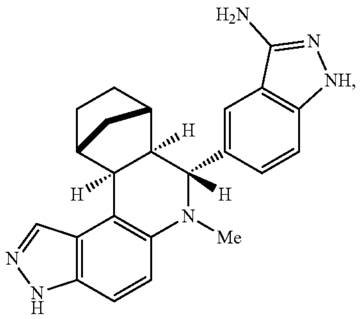
HSD1931
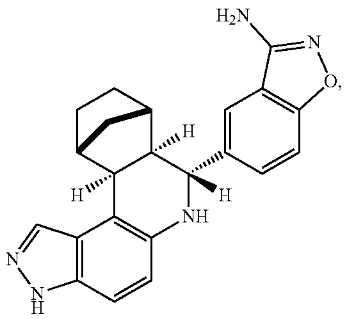
HSD5001
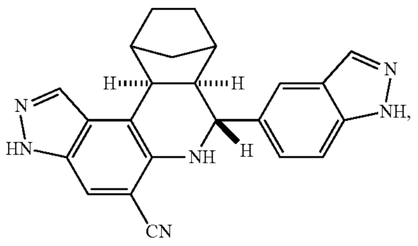
-continued
HSD5002
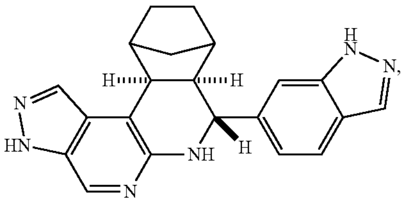
HSD5003
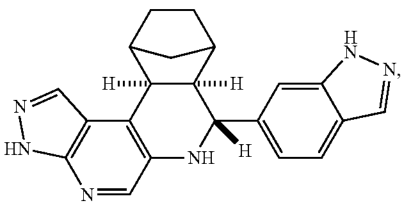
HSD5024
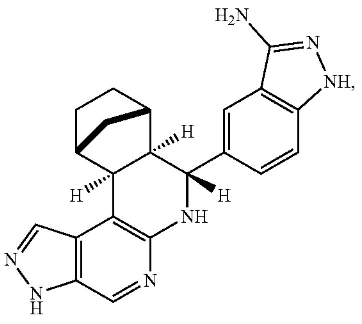
HSD1901
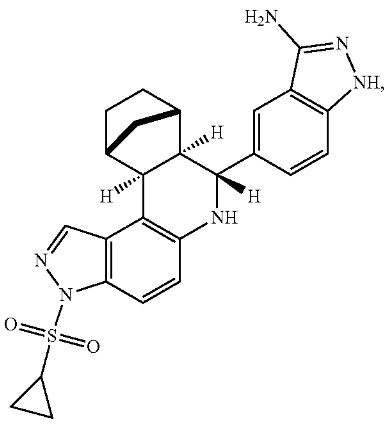
HSD5004
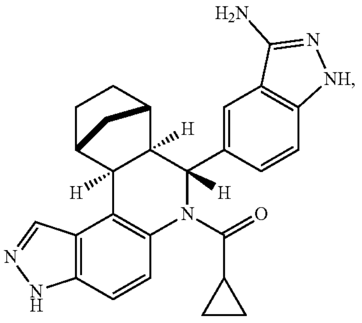

-continued
HSD5005
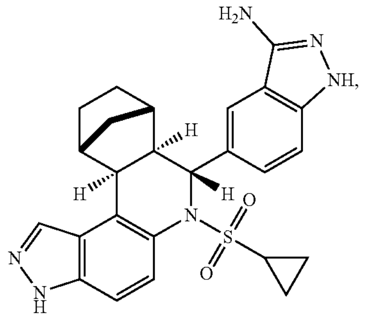
HSD1945
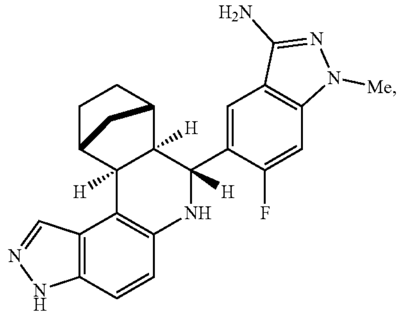
HSD5025
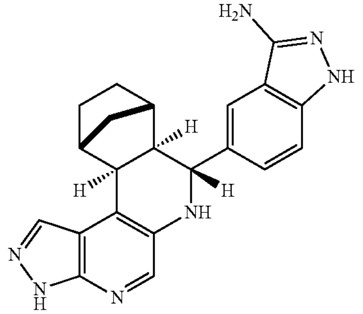
and
HSD5026
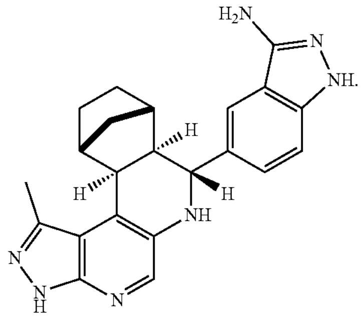
4. A compound selected from the group consisting of
S-12
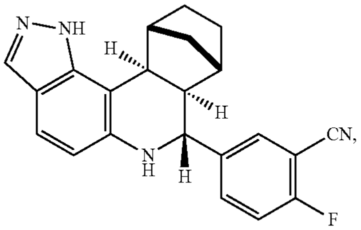
-continued
31
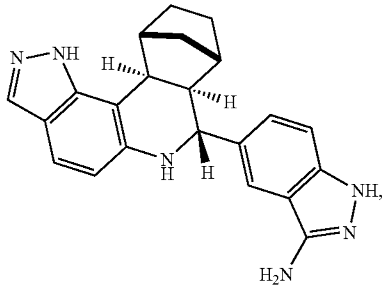
and
HSD4051
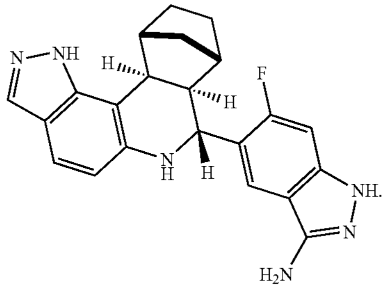
5. A compound selected from the group consisting of
HSD2030
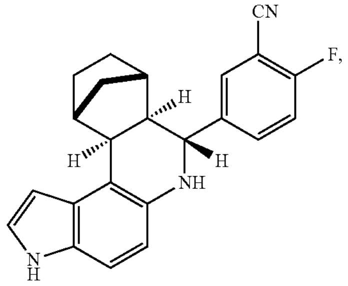
HSD4017
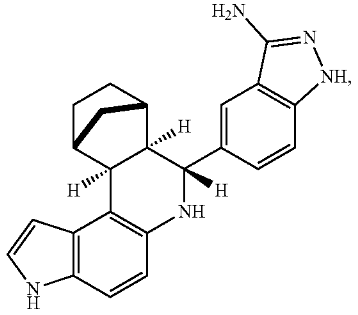
HSD5006
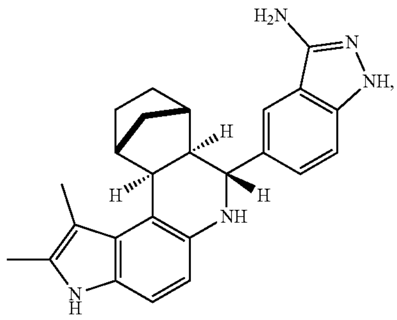

-continued
HSD5007
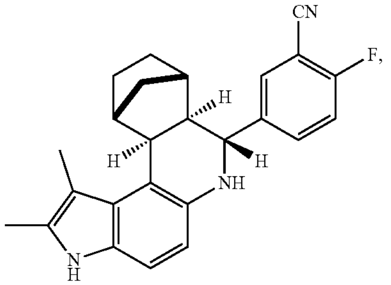
HSD5008
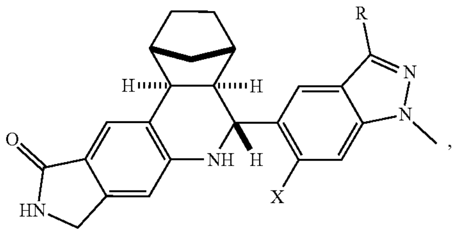
HSD5009
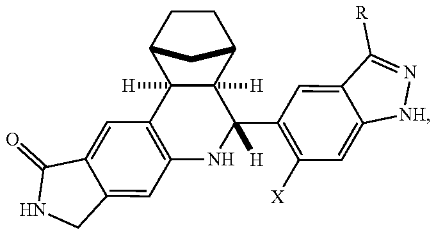
HSD5010
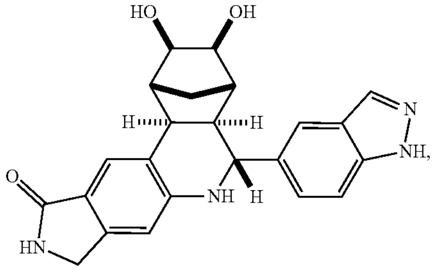
HSD1910
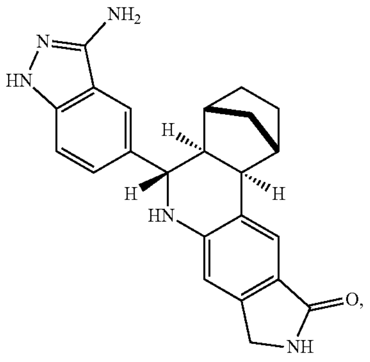
-continued
HSD1911
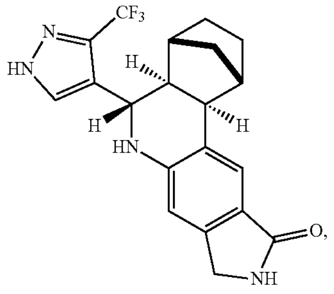
HSD1909
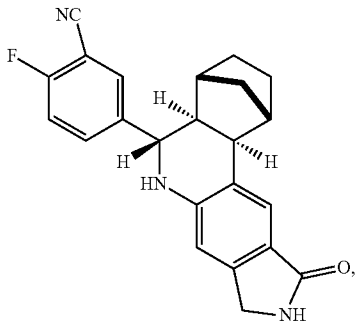
and
HSD1818
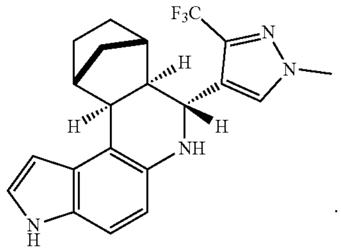
6. A compound selected from the group consisting of
HSD1927
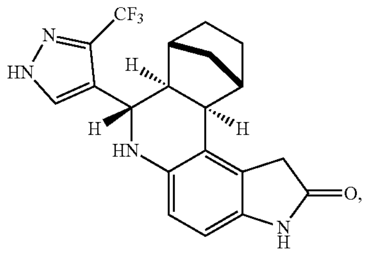
HSD1929
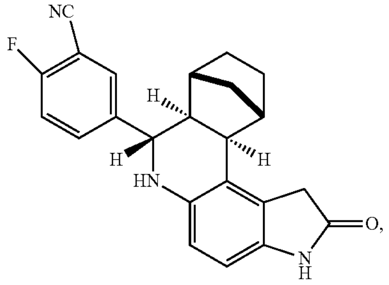

-continued
HSD1930
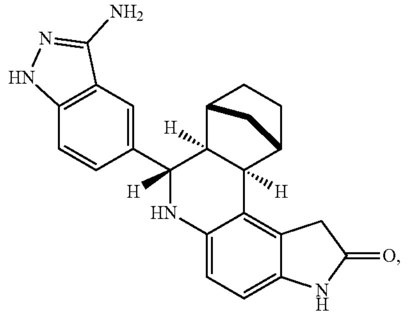
HSD5011
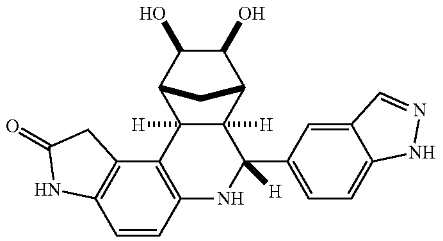
and
HSD5012
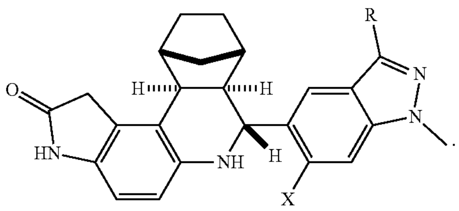
7. A compound selected from the group consisting of
HSD1949
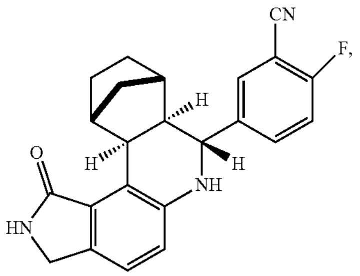
HSD1950
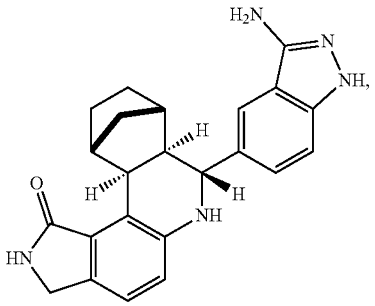
-continued
HSD1943
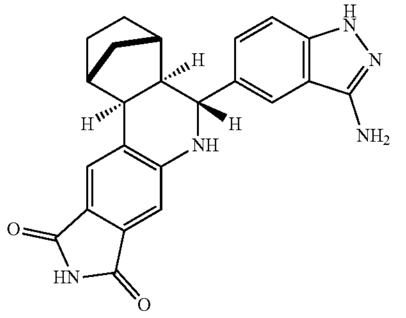
and
HSD1944
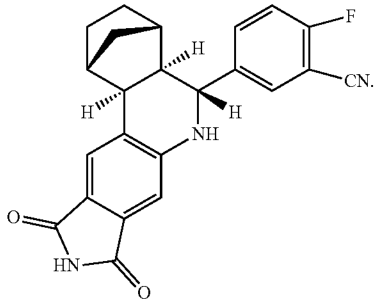
8. A compound selected from the group consisting of
33
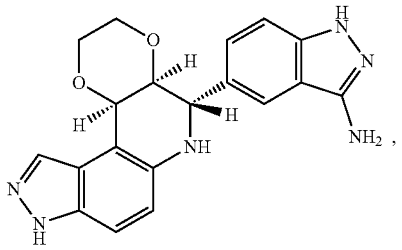
HSD2015
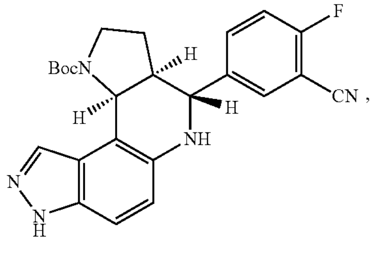
HSD2038
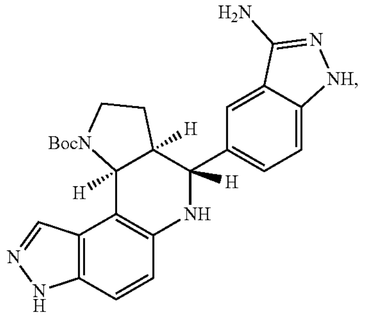

-continued
HSD2039
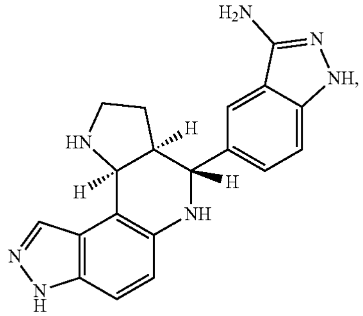
HSD1880
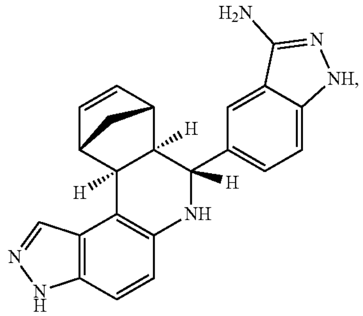
HSD1792
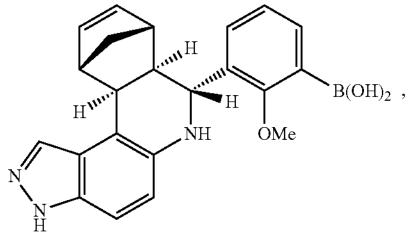
HSD1799
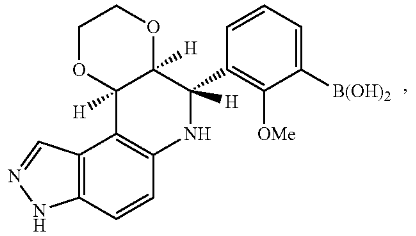
HSD2024
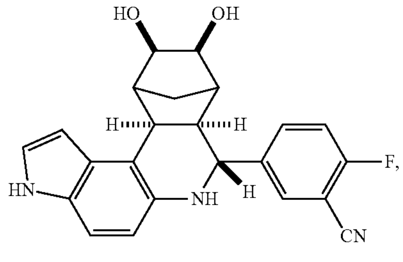
HSD5013
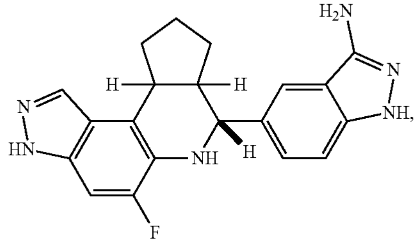
-continued
HSD5014
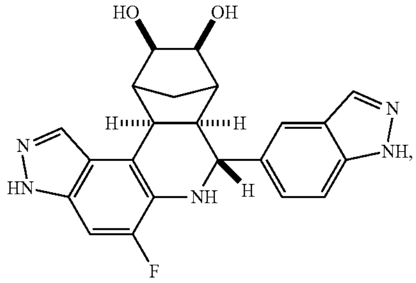
HSD5015
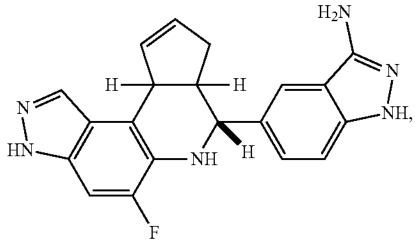
HSD5016
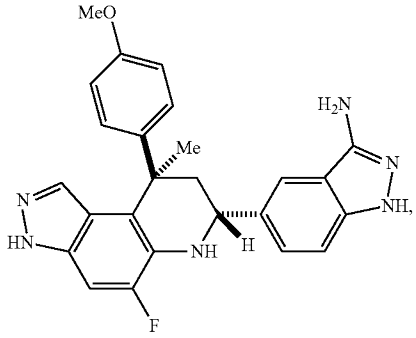
HSD5017
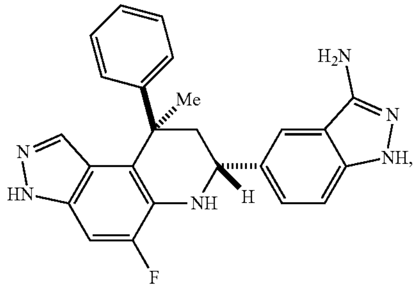
HSD5018
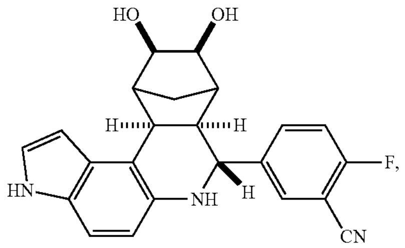

-continued
HSD1831
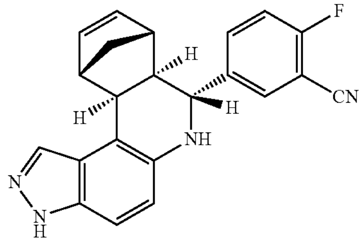 and
HSD5019
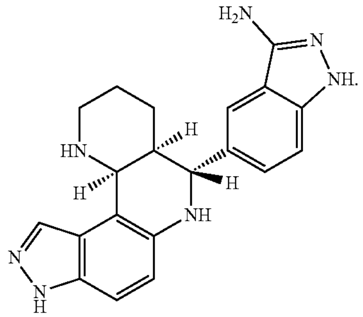
9. A compound selected from the group consisting of
HSDB1
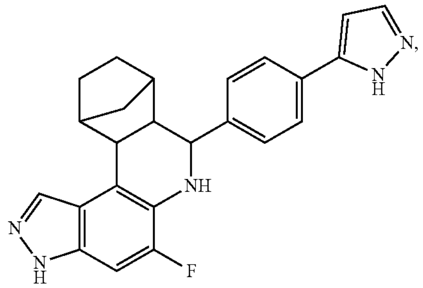
HSDB2
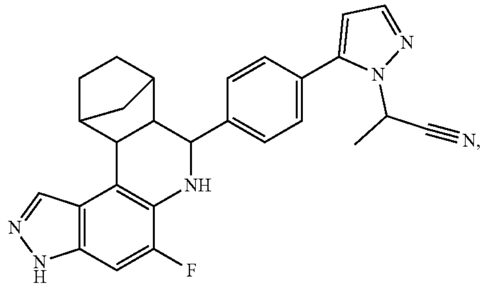
HSDB3
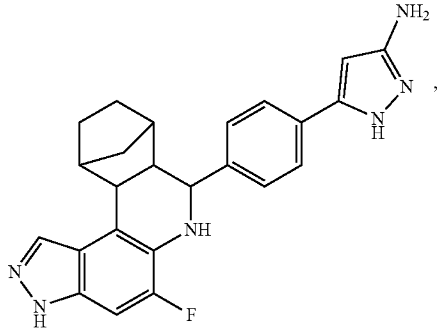
-continued
HSDB4
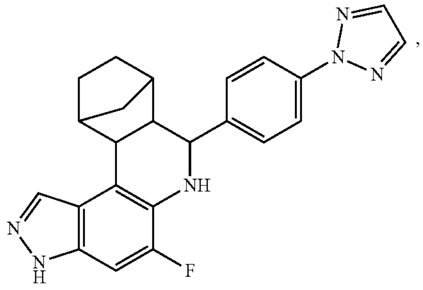
HSDB5
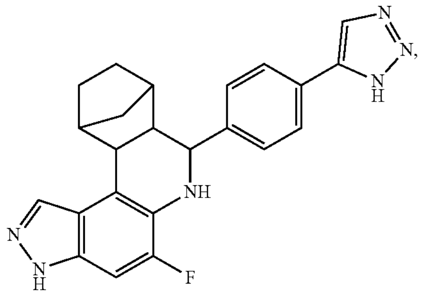
HSDB6
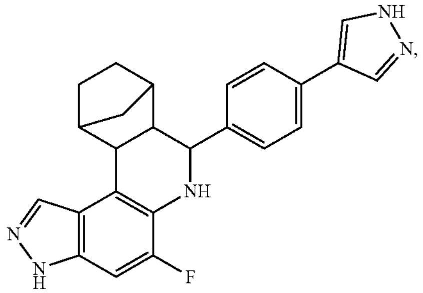
HSDB7
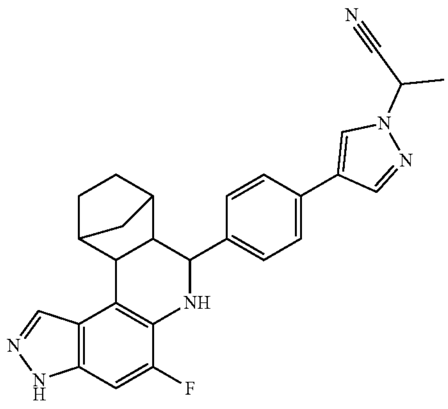 ,
HSDB8
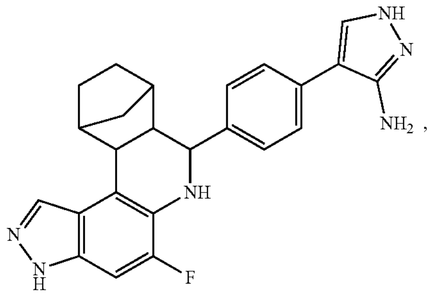

-continued
HSDB9
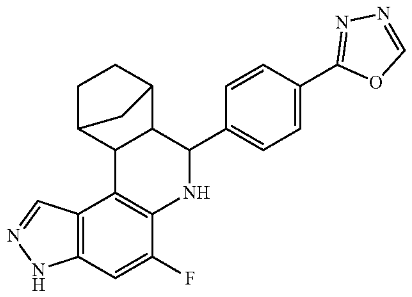
and
HSDB10
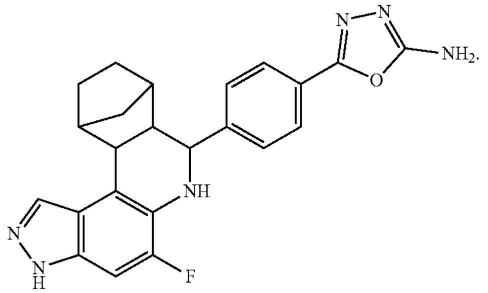
10. A compound selected from the group consisting of
HSDC1
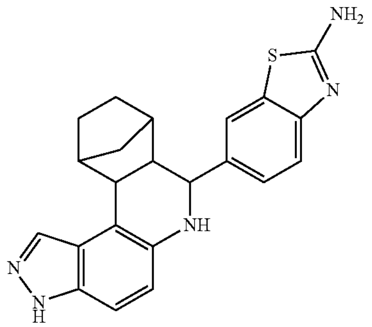
,
HSDC2
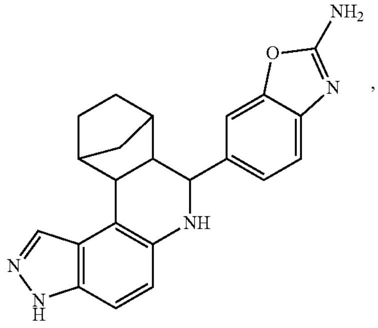
,
-continued
HSDC3
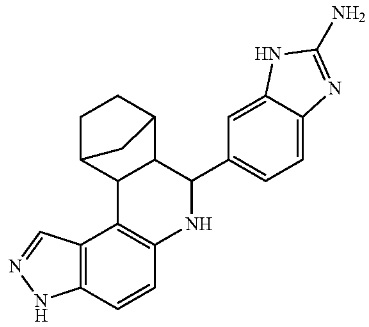
,
HSDC4
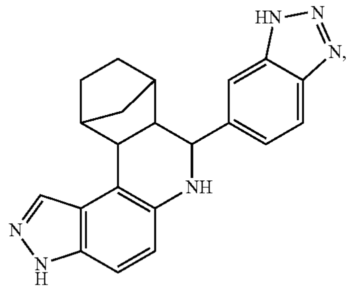
HSDC5
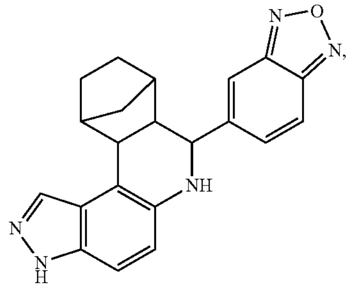
HSDC6
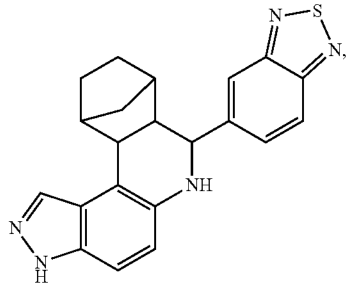
HSDC7
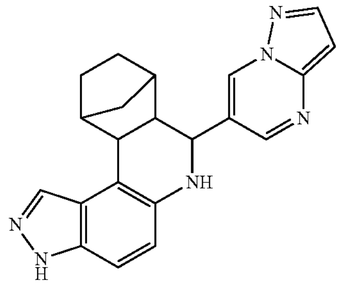
, -continued
HSDC8
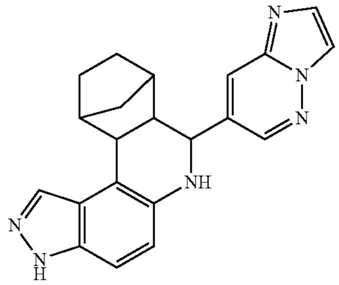
,
HSDC9
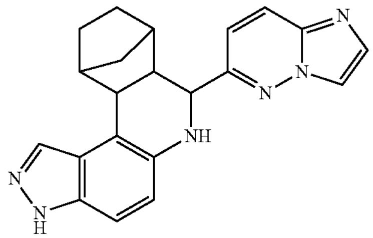
,
HSDC10
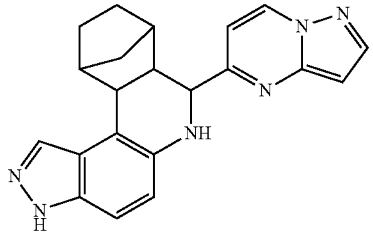
,
HSDC11
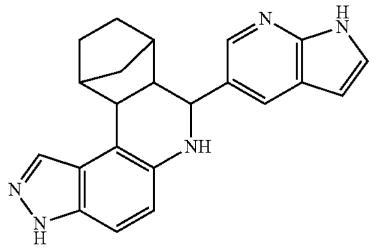
,
HSDC12
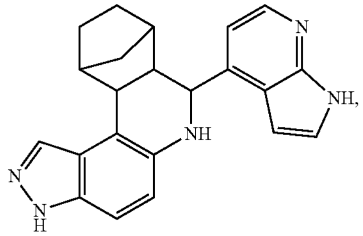
HSDC13
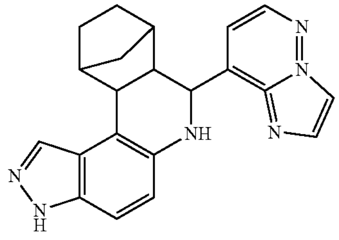
,
-continued
HSDC14
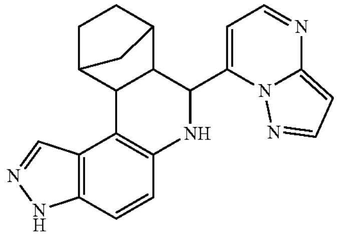
,
HSDC15
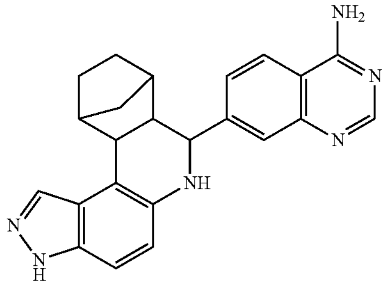
,
HSDC16
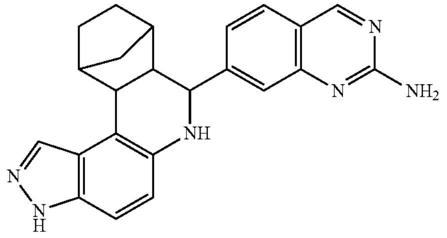
,
HSDC1b
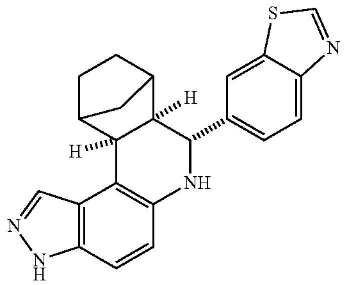
,
HSDC1c
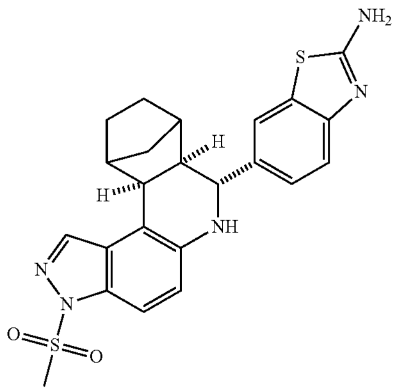
, -continued
HSDC1d
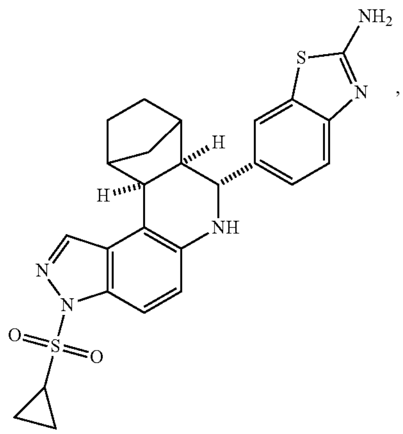
,
HSDC1e
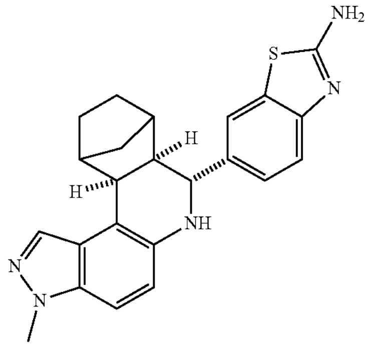
,
HSDC1f
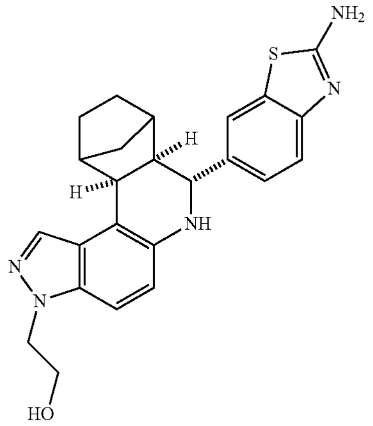
,
HSDC1g
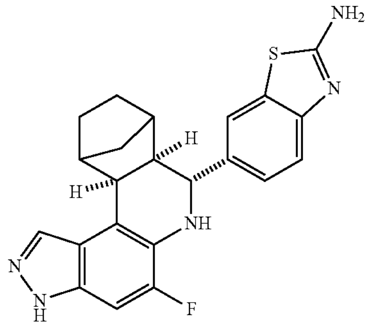
,
-continued
HSDC1h
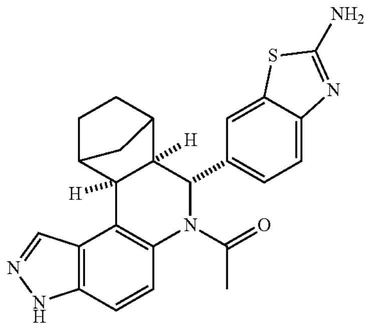
,
HSDC1i
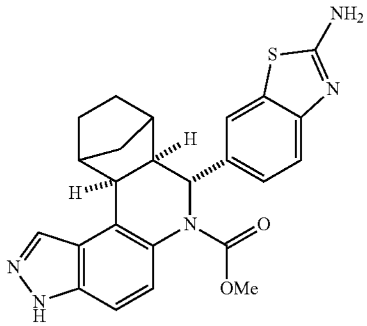
,
HSDC1j
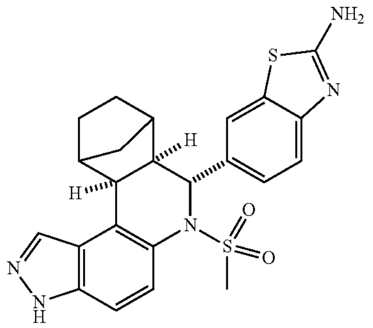
,
HSDC1k
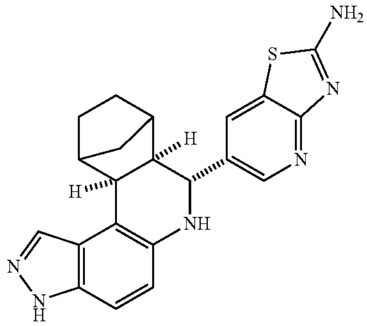
,
HSDC1m
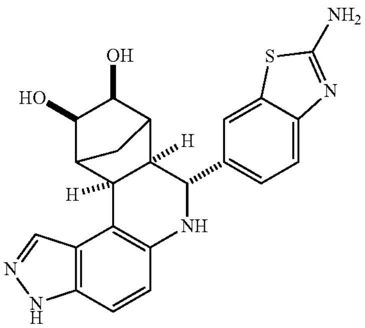
, -continued HSDC1n

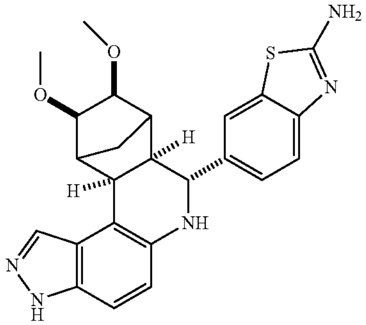

and

HSDC1o

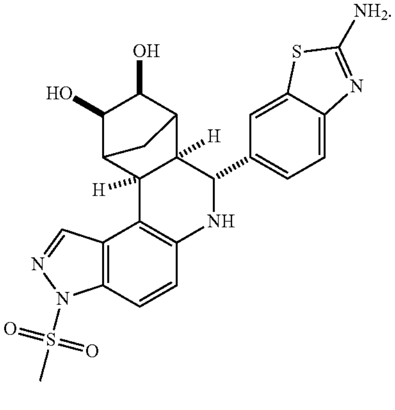

11. A pharmaceutical composition comprising a compound of claim 1, or a pharmaceutically acceptable salt thereof, and a pharmaceutically acceptable carrier, excipient or diluent.

12. A pharmaceutical composition comprising a compound of claim 2 and a pharmaceutically acceptable carrier, excipient or diluent.

13. A pharmaceutical composition comprising a compound of claim 4 and a pharmaceutically acceptable carrier, excipient or diluent.

14. A pharmaceutical composition comprising a compound of claim 5 and a pharmaceutically acceptable carrier, excipient or diluent.

15. A pharmaceutical composition comprising a compound of claim 6 and a pharmaceutically acceptable carrier, excipient or diluent.

16. A pharmaceutical composition comprising a compound of claim 7 and a pharmaceutically acceptable carrier, excipient or diluent.

17. A pharmaceutical composition comprising a compound of claim 8 and a pharmaceutically acceptable carrier, excipient or diluent.

18. A pharmaceutical composition comprising a compound of claim 9 and a pharmaceutically acceptable carrier, excipient or diluent.

19. A pharmaceutical composition comprising a compound of claim 10 and a pharmaceutically acceptable carrier, excipient or diluent.

* * * * *